United States Patent
Cianchetta et al.

(10) Patent No.: US 9,458,132 B2
(45) Date of Patent: *Oct. 4, 2016

(54) THERAPEUTIC COMPOUNDS AND COMPOSITIONS AND THEIR USE AS PKM2 MODULATORS

(71) Applicant: AGIOS PHARMACEUTICALS, INC., Cambridge, MA (US)

(72) Inventors: Giovanni Cianchetta, Waltham, MA (US); Janeta Popovici-Muller, Windham, NH (US); Jeffrey O. Saunders, Lincoln, MA (US); Robert Zahler, Pennington, NJ (US)

(73) Assignee: AGIOS PHARMACEUTICALS, INC, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/441,746

(22) PCT Filed: Nov. 8, 2013

(86) PCT No.: PCT/US2013/069193
§ 371 (c)(1),
(2) Date: May 8, 2015

(87) PCT Pub. No.: WO2014/074848
PCT Pub. Date: May 15, 2014

(65) Prior Publication Data
US 2015/0307473 A1  Oct. 29, 2015

Related U.S. Application Data

(60) Provisional application No. 61/724,266, filed on Nov. 8, 2012.

(51) Int. Cl.
| | | |
|---|---|---|
| *C07D 205/02* | (2006.01) | |
| *C07D 401/12* | (2006.01) | |
| *C07D 401/14* | (2006.01) | |
| *C07D 405/12* | (2006.01) | |
| *C07D 205/04* | (2006.01) | |

(52) U.S. Cl.
CPC .......... *C07D 401/12* (2013.01); *C07D 205/04* (2013.01); *C07D 401/14* (2013.01); *C07D 405/12* (2013.01)

(58) Field of Classification Search
CPC  C07D 205/02; C07D 401/12; C07D 401/14; C07D 405/12
See application file for complete search history.

(56) References Cited

U.S. PATENT DOCUMENTS 9,193,701 B2 * 11/2015 Su ..................... A61K 31/4965

| 2014/0073625 A1* | 3/2014 | Salituro | C07D 215/36 |
| | | | 514/210.18 |
| 2014/0155374 A1* | 6/2014 | Su | A61K 31/397 |
| | | | 514/210.18 |
| 2014/0194402 A1* | 7/2014 | Su | A61K 31/4965 |
| | | | 514/210.2 |

FOREIGN PATENT DOCUMENTS

| JP | H07165708 A | 6/1995 |
| JP | 2008514590 A | 5/2008 |
| WO | 9948490 A1 | 9/1999 |
| WO | 0117956 A1 | 3/2001 |
| WO | 2006033628 A1 | 3/2006 |
| WO | 2010105243 A1 | 9/2010 |
| WO | 2010118063 A2 | 10/2010 |
| WO | 2010124082 A1 | 10/2010 |
| WO | 2011002817 A1 | 1/2011 |
| WO | 2012052102 A1 | 4/2012 |
| WO | 2012083246 * | 6/2012 |
| WO | 2012083246 A1 | 6/2012 |

OTHER PUBLICATIONS

Beutler et al. "Elevated Pyruvate Kinase Activity in Patients with Hemolytic Anemia Due to Red Cell Pyruvate Kinase 'Deficiency'" The American Journal of Medicine (1987) vol. 83, pp. 899-904.

Boxer, et al. "Evaluation of Substituted N,N'-Diarylsulfonamides as Activators of the Tumor Cell Specific M2 Isoform of Pyruvate Kinase" Journal of Medicinal Chemistry (2010) vol. 53, pp. 1048-1055.

European Search Report for European Application No. 11808773.3 dated Apr. 9, 2014.

International Search Report and Written Opinion for International Application No. PCT/US2012/036406 dated Jul. 6, 2012.

International Search Report and Written Opinion for International Application No. PCT/US2013/069193 dated Feb. 26, 2014.

International Search Report dated Apr. 4, 2012 for related Application PCT/US2011/065633.

Walsh et al. "2-oxo-N-aryl-1,2,3,4-tetrahydroquinoline-6-sulfonamides as activators of the tumor cell specific M2 isoform of pyruvate kinase" Bioorg Med Chem Lett. Nov. 1, 2011; 21(21): 6322-6327.

* cited by examiner

*Primary Examiner* — D M Seaman

(57) ABSTRACT

Compositions comprising compounds of general formula (I) that modulate pyruvate kinase are described herein. Also described herein are methods of using the compounds that modulate pyruvate kinase in the treatment of diseases.

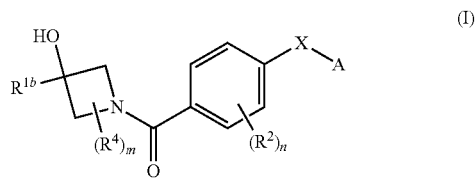

(I)

25 Claims, No Drawings

THERAPEUTIC COMPOUNDS AND COMPOSITIONS AND THEIR USE AS PKM2 MODULATORS

CLAIM OF PRIORITY

This application is a national stage application under 35 U.S.C. §371 of International Application No. PCT/US2013/069193, filed Nov. 8, 2013, published as International Publication No. WO2014/074848 on May 15, 2014 which claims priority from U.S.S.N. 61/724,266, filed Nov. 8, 2012, the contents of each of which is incorporated herein by reference in its entirety.

BACKGROUND OF INVENTION

Pyruvate kinase deficiency (PKD) is one of the most common enzyme defects in erythrocytes in human due to autosomal recessive mutations of the PKLR gene (Zanella, A., et al., *Br J Haematol* 2005, 130 (1), 11-25). It is also the most frequent enzyme mutation in the central glycolytic pathway and only second to glucose-6 phosphate dehydrogenase (G6PD) deficiency (Kedar, P., et al., *Clin Genet* 2009, 75 (2), 157-62) of the hexose monophosphate shunt.

Human erythrocytes are unique in that they anucleate when mature Immature erythrocytes have nuclei but during early erythropoiesis prior to becoming circulating reticulocytes they extrude nuclei as well as other organelles such as mitochondria, endoplasmic reticulum, and golgi aparatus, in order to make room for oxygen-carrying hemoglobin. As a result of lacking mitochondria, mature red blood cells do not utilize any of the oxygen they transport to economically synthesize adenosine triphosphate (ATP) as other normal differentiated cells do. Instead, red blood cells depend entirely on anaerobic glycolysis to cycle nicotinamide adenine dinucleotide ($NAD^+$) and to make ATP, an essential energy source largely used to drive ATPase-dependent $K^+/Na^+$ and $Ca^{2+}$ pumps, in order to maintain cell membrane integrity and pliability as they navigate through blood vessels. In PKD disorder, two major distinctive metabolic abnormalities are ATP depletion and concomitant increase of 2,3-diphosphoglycerate consistent with accumulation of upper glycolytic intermediates. Moreover, one of the consequences of decreased ATP and pyruvate level is lowered lactate level leading to inability to regenerate $NAD^+$ through lactate dehydrogenase for further use in glycolysis. The lack of ATP disturbs the cation gradient across the red cell membrane, causing the loss of potassium and water, which causes cell dehydration, contraction, and crenation, and leads to premature destruction and diminished lifetime of the red blood cells (RBCs). Such defective RBCs are destroyed in the spleen, and excessive hemolysis rate in the spleen leads to the manifestation of hemolytic anemia. The exact mechanism by which PKD sequesters newly matured RBCs in the spleen to effectively shorten overall half-lives of circulating RBCs is not yet clear, but recent studies suggest that metabolic dysregulation affects not only cell survival but also the maturation process resulting in ineffective erythropoiesis (Aizawa, S. et al., *Exp Hematol* 2005, 33 (11), 1292-8).

Pyruvate kinase catalyzes the transfer of a phosphoryl group from phosphoenolpyruvate (PEP) to ADP, yielding one molecule of pyruvate and one molecule of ATP. The enzyme has an absolute requirement for $Mg^{2+}$ and $K^+$ cations to drive catalysis. PK functions as the last critical step in glycolysis because it is an essentially irreversible reaction under physiological conditions. In addition to its role of synthesizing one of the two ATP molecules from the metabolism of glucose to pyruvate, pyruvate kinase is also an important cellular metabolism regulator. It controls the carbon flux in lower-glycolysis to provide key metabolite intermediates to feed biosynthetic processes, such as pentose-phosphate pathway among others, in maintaining healthy cellular metabolism. Because of these critical functions, pyruvate kinase is tightly controlled at both gene expression and enzymatic allostere levels. In mammals, fully activated pyruvate kinase exists as a tetrameric enzyme. Four different isozymes (M1, M2, L and R) are expressed from two separate genes. Erythrocyte-specific isozyme PKR is expressed from the PKLR gene ("L gene") located on chromosome 1q21. This same gene also encodes the PKL isozyme, which is predominately expressed in the liver. PKLR consists of 12 exons with exon 1 is erythroid-specific whereas exon 2 is liver-specific. The two other mammalian isozymes PKM1 and PKM2 are produced from the PKM gene ("M gene") by alternative splicing events controlled by hnRNP proteins. The PKM2 isozyme is expressed in fetal tissues and in adult proliferating cells such as cancer cells. Both PKR and PKM2 are in fact expressed in proerythroblasts. However, upon erythroid differentiation and maturation, PKM2 gradually is decreased in expression and progressively replaced by PKR in mature erythrocytes.

Clinically, hereditary PKR deficiency disorder manifests as non-spherocytic hemolytic anemia. The clinical severity of this disorder range from no observable symptoms in fully-compensated hemolysis to potentially fatal severe anemia requiring chronic transfusions and/or splenectomy at early development or during physiological stress or serious infections. Most affected individuals who are asymptomatic, paradoxically due to enhanced oxygen-transfer capacity, do not require any treatment. However, for some of the most severe cases, while extremely rare population-wise with estimated prevalence of 51 per million (Beutler, E. *Blood* 2000, 95 (11), 3585-8), there is no disease-modifying treatment available for these patients other than palliative care (Tavazzi, D. et al., *Pediatr Ann* 2008, 37 (5), 303-10). These hereditary non-spherocytic haemolytic anemia (HNSHA) patients present a clear unmet medical need.

Heterogenous genetic mutations in PKR lead to dysregulation of its catalytic activity. Since the initial cloning of PKR and report of a single point mutation $Thr^{384}>Met$ associated with a HNSHA patient (Kanno, H. et al., *Proc Natl Acad Sci USA* 1991, 88 (18), 8218-21), there are now nearly 200 different reported mutations associated with this disease reported worldwide (Zanella, A. et al., *Br J Haematol* 2005, 130 (1), 11-25; Kedar, P., et al., *Clin Genet* 2009, 75 (2), 157-62; Fermo, E. et al., *Br J Haematol* 2005, 129 (6), 839-46; Pissard, S. et al., *Br J Haematol* 2006, 133 (6), 683-9). Although these mutations represent wide range genetic lesions that include deletional and transcriptional or translational abnormalities, by far the most common type is missense mutation in the coding region that one way or another affects conserved residues within domains that are structurally important for optimal catalytic function of PKR. The pattern of mutation prevalence seems to be unevenly distributed toward specific ethnic backgrounds. For instance, the most frequent codon substitutions reported for North American and European patients appear to be $Arg^{486}>Trp$ 1 and $Arg^{510}>Gln$, while mutations $Arg^{479}>His$, $Arg^{490}>Trp$ and $Asp^{331}>Gly$ were more frequently found in Asian patients (Kedar, P., et al., *Clin Genet* 2009, 75 (2), 157-62).

Cancer cells rely primarily on glycolysis to generate cellular energy and biochemical intermediates for biosynthesis of lipids and nucleotides, while the majority of "normal" cells in adult tissues utilize aerobic respiration. This fundamental difference in cellular metabolism between cancer cells and normal cells, termed the Warburg Effect, has been exploited for diagnostic purposes, but has not yet been exploited for therapeutic benefit.

Pyruvate kinase (PK) is a metabolic enzyme that converts phosphoenolpyruvate to pyruvate during glycolysis. Four PK isoforms exist in mammals: the L and R isoforms are expressed in liver and red blood cells, the M1 isoform is expressed in most adult tissues, and the M2 isoform is a splice variant of M1 expressed during embryonic development. All tumor cells exclusively express the embryonic M2 isoform. A well-known difference between the M1 and M2 isoforms of PK is that M2 is a low-activity enzyme that relies on allosteric activation by the upstream glycolytic intermediate, fructose-1,6-bisphosphate (FBP), whereas M1 is a constitutively active enzyme.

All tumor cells exclusively express the embryonic M2 isoform of pyruvate kinase, suggesting PKM2 as a potential target for cancer therapy. PKM2 is also expressed in adipose tissue and activated T-cells. Phosphotyrosine peptide binding to PKM2 leads to a dissociation of FBP from PKM2 and conformational changes of PKM2 from an active, tetrameric form to an inactive form. Compounds that bind to PKM2 and lock the enzyme in the active confirmation will lead to the loss of allosteric control of PKM2 needed for shunting biochemical intermediates from glycolysis into biosynthesis of nucleotides and lipids. Thus, the activation of PKM2 can inhibit the growth and proliferation of cancer cells, activated immune cells, and fat cells. Activation of PKM2 may therefore be effective in the treatment of cancer, obesity, diabetes, autoimmune conditions, and proliferation-dependent diseases, e.g., benign prostatic hyperplasia (BPH).

SUMMARY OF INVENTION

Described herein are compounds that activate pyruvate kinase and pharmaceutically acceptable salts, solvates, and hydrates thereof, for example, compounds that activate PKR and/or PKM2.

Also provided are pharmaceutical compositions comprising a compound provided herewith and the use of such compositions in methods of treating diseases and conditions that are related to pyruvate kinase function, e.g., PKR function, and/or PKM2 function (including, e.g., cancer, diabetes, obesity, autoimmune disorders, and benign prostatic hyperplasia (BPH)).

In one embodiment, provided herein is a compound of Formula (I):

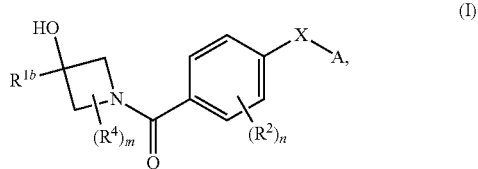

or a pharmaceutically acceptable salt thereof, wherein:

A is aryl or heteroaryl, wherein the aryl or heteroaryl is optionally substituted, and the aryl or heteroaryl is optionally fused to an optionally substituted carbocyclyl or an optionally substituted heterocyclyl;

X is selected from —NH—S(O)$_2$—, —N(alkyl)-S(O)$_2$—, —S(O)$_2$—NH— and —S(O)$_2$—N(alkyl)-;

R$^{1b}$ is C$_{2-8}$ alkyl, cycloalkyl, aryl, heteroaryl, cycloalkylalkyl, aralkyl or heteroaralkyl, wherein each aryl is substituted and each C$_{2-8}$ alkyl, cycloalkyl, cycloalkylalkyl, aralkyl, heteroaryl or heteroaralkyl is optionally substituted;

each R$^2$ is independently selected from halo and haloalkyl;

each R$^4$ is independently selected from alkyl, alkoxy, haloalkyl and hydroxyl;

n is 0, 1 or 2; and m is 0, 1 or 2;

wherein when R$^{1b}$ is unsubstituted benzyl, X is —NH—S(O)$_2$— and A is quinolin-8-yl; then n is 1.

In another embodiment, provided is a method for treating or preventing (e.g., treating) a disease, condition or disorder as described herein comprising administering a compound provided herein, a pharmaceutically acceptable salt, solvate or hydrate thereof, or pharmaceutical composition thereof.

In another embodiment, provided is a method for increasing lifetime of the red blood cells (RBCs) in need thereof comprising contacting blood with an effective amount of (1) a compound disclosed herein or a pharmaceutically acceptable salt, solvate or hydrate thereof; (2) a composition comprising a compound disclosed herein or a salt, solvate or hydrate thereof and a carrier; or (3) a pharmaceutical composition comprising a compound disclosed herein or a pharmaceutically acceptable salt, solvate or hydrate thereof, and a pharmaceutically acceptable carrier.

In another embodiment, provided is a method for regulating 2,3-diphosphoglycerate levels in blood in need thereof comprising contacting blood with an effective amount of (1) a compound disclosed herein or a pharmaceutically acceptable salt, solvate or hydrate thereof; (2) a composition comprising a compound disclosed herein or a salt, solvate or hydrate thereof and a carrier; or (3) a pharmaceutical composition comprising a compound disclosed herein or a pharmaceutically acceptable salt, solvate or hydrate thereof, and a pharmaceutically acceptable carrier.

In another embodiment, provided is a method for treating hereditary non-spherocytic haemolytic anemia comprising administering to a subject in need thereof a therapeutically effective amount of (1) a compound disclosed herein or a pharmaceutically acceptable salt, solvate or hydrate thereof; (2) a pharmaceutical composition comprising a compound disclosed herein or a pharmaceutically acceptable salt, solvate or hydrate thereof, and a pharmaceutically acceptable carrier.

In another embodiment, provided is a method for treating sickle cell anemia comprising administering to a subject in need thereof a therapeutically effective amount of (1) a compound disclosed herein or a pharmaceutically acceptable salt, solvate or hydrate thereof; (2) a pharmaceutical composition comprising a compound disclosed herein or a pharmaceutically acceptable salt, solvate or hydrate thereof, and a pharmaceutically acceptable carrier.

In another embodiment, provided is a method for treating hemolytic anemia (e.g., chronic hemolytic anemia caused by phosphoglycerate kinase deficiency, Blood Cells Mol Dis, 2011; 46(3):206) comprising administering to a subject in need thereof a therapeutically effective amount of (1) a compound disclosed herein or a pharmaceutically acceptable salt, solvate or hydrate thereof; (2) a pharmaceutical composition comprising a compound disclosed herein or a pharmaceutically acceptable salt, solvate or hydrate thereof, and a pharmaceutically acceptable carrier.

In another embodiment, provided is a method for treating diseases or conditions that are associated with increased 2,3-diphosphoglycerate levels (e.g., liver diseases (Am J Gastroenterol, 1987; 82(12):1283) and Parkinson's (J. Neurol, Neurosurg, and Psychiatry 1976, 39:952) comprising administering to a subject in need thereof a therapeutically effective amount of (1) a compound disclosed herein or a pharmaceutically acceptable salt, solvate or hydrate thereof; (2) a pharmaceutical composition comprising a compound disclosed herein or a pharmaceutically acceptable salt, solvate or hydrate thereof, and a pharmaceutically acceptable carrier.

In another embodiment, provided is a method for treating thalassemia (e.g., beta-thalassemia), hereditary spherocytosis, hereditary elliptocytosis, abetalipoproteinemia (or Bassen-Kornzweig syndrome), paroxysmal nocturnal hemoglobinuria, acquired hemolytic anemia (e.g., congenital anemias (e.g., enzymopathies)), or anemia of chronic diseases comprising administering to a subject in need thereof a therapeutically effective amount of (1) a compound disclosed herein or a pharmaceutically acceptable salt, solvate or hydrate thereof; (2) a pharmaceutical composition comprising a compound disclosed herein or a pharmaceutically acceptable salt, solvate or hydrate thereof, and a pharmaceutically acceptable carrier.

In another embodiment, provided is a method for treating diseases or conditions that are associated with increased 2,3-diphosphoglycerate levels (e.g., liver diseases (Am J Gastroenterol, 1987; 82(12):1283) and Parkinson's (J. Neurol, Neurosurg, and Psychiatry 1976, 39:952) comprising administering to a subject in need thereof a therapeutically effective amount of (1) a compound disclosed herein or a pharmaceutically acceptable salt, solvate or hydrate thereof; (2) a pharmaceutical composition comprising a compound disclosed herein or a pharmaceutically acceptable salt, solvate or hydrate thereof, and a pharmaceutically acceptable carrier.

Compounds and compositions described herein are activators of PKR mutants having lower activities compared to the wild type, thus are useful for methods of the present invention. Such mutations in PKR can affect enzyme activity (catalytic efficiency), regulatory properties (modulation by fructose bisphosphate (FBP)/ATP), and/or thermostability of the enzyme. Examples of such mutations are described in Valentini et al, JBC 2002. Some examples of the mutants that are activated by the compounds described herein include G332S, G364D, T384M, G37E, R479H, R479K, R486W, R532W, R510Q, and R490W. Without being bound by theory, compounds described herein affect the activities of PKR mutants by activating FBP non-responsive PKR mutants, restoring thermostability to mutants with decreased stability, or restoring catalytic efficiency to impaired mutants. The activating activity of the present compounds against PKR mutants may be tested following a method described in Examples 2-5. Compounds described herein are also activators of wild type PKR.

In an embodiment, to increase the lifetime of the red blood cells, a compound, composition or pharmaceutical composition described herein is added directly to whole blood or packed cells extracorporeally or be provided to the subject (e.g., the patient) directly (e.g., by i.p., i.v., i.m., oral, inhalation (aerosolized delivery), transdermal, sublingual and other delivery routes). Without being bound by theory, compounds described herein increase the lifetime of the RBCs, thus counteract aging of stored blood, by impacting the rate of release of 2,3-DPG from the blood. A decrease in the level of 2,3-DPG concentration induces a leftward shift of the oxygen-hemoglobin dissociation curve and shifts the allosteric equilibribrium to the R, or oxygenated state, thus producing a therapeutic inhibition of the intracellular polymerization that underlies sickling by increasing oxygen affinity due to the 2,3-DPG depletion, thereby stabilizing the more soluble oxy-hemoglobin. Accordingly, in one embodiment, compounds and pharmaceutical compositions described herein are useful as antisickling agents. In another embodiment, to regulate 2,3-diphosphoglycerate, a compound, composition or pharmaceutical composition described herein is added directly to whole blood or packed cells extracorporeally or be provided to the subject (e.g., the patient) directly (e.g., by i.p., i.v., i.m., oral, inhalation (aerosolized delivery), transdermal, sublingual and other delivery routes).

In another embodiments, provided is a method of increasing the level of PKM2 activity and/or glycolysis in a patient in need thereof. The method comprises the step of administering an effective amount of a compound described herein to the patient in need thereof, thereby increasing the level of PKM2 activity and/or glycolysis in the patient. In some embodiments, a compound or a composition described herein is used to maintain PKM2 in its active conformation or activate pyruvate kinase activity in proliferating cells as a means to divert glucose metabolites into catabolic rather than anabolic processes in the patient.

In another embodiment, provided is a method of inhibiting cell proliferation in a patient in need thereof. The method comprises the step of administering an effective amount of a compound described herein to the patient in need thereof, thereby inhibiting cell proliferation in the patient. In one aspect this method can inhibit growth of a transformed cell, more specifically a cancer cell. In another aspect the method generally inhibits growth of a PKM2-dependent cell that undergoes aerobic glycolysis.

In another embodiment, provided is a method of treating a patient suffering from or susceptible to a disease or disorder associated with reduced PKM2 activity or reduced glycolysis in a patient in need thereof. The method comprises the step of administering an effective amount of a compound described herein to the patient in need thereof, thereby treating, preventing or ameliorating the disease or disorder in the patient. In certain embodiment the compound described herein is provided in a pharmaceutical composition. In certain embodiments, the method includes the step of identifying or selecting a patient who would benefit from activation of PKM2 prior to treatment. Identifying or selecting such a patient can be on the basis of the level of PKM2 activity in a cell of the patient. In one aspect, the selected patient is suffering from or susceptible to unwanted cell growth or proliferation, e.g., cancer, obesity, diabetes, atherosclerosis, restenosis, and autoimmune diseases. In another aspect, the selected patient is suffering from a cancer associated with PKM2 function.

In another embodiment, the compound described herein is administered at a dosage and frequency sufficient to increase lactate production or oxidative phosphorylation.

DETAILED DESCRIPTION

The details of construction and the arrangement of components set forth in the following description or illustrated in the drawings are not meant to be limiting. Embodiments can be practiced or carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

Definitions

The term "halo" or "halogen" refers to any radical of fluorine, chlorine, bromine or iodine.

The term "alkyl" refers to a monovalent hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. In certain aspects, the term "alkyl" refers to a monovalent hydrocarbon chain that may be a straight chain or branched chain, containing 1 to 6 carbon atoms. In other aspects, the term "alkyl" refers to a monovalent hydrocarbon chain that may be a straight chain or branched chain, containing 1 to 4 carbon atoms.

The term "haloalkyl" refers to an alkyl in which one or more hydrogen atoms are replaced by halo, and includes alkyl moieties in which all hydrogens have been replaced by halo (e.g., perfluoroalkyl).

The term "alkenyl" refers to a monovalent straight or branched hydrocarbon chain containing 2-12 carbon atoms and having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent. In certain aspects, the term "alkenyl" refers to a monovalent straight or branched hydrocarbon chain containing 2-6 carbon atoms and having one or more double bonds. In other aspects, the term "alkenyl" refers to a monovalent straight or branched hydrocarbon chain containing 2-4 carbon atoms and having one or more double bonds.

The term "alkoxy" refers to an —O-alkyl radical.

The term "aryl" refers to a monocyclic, bicyclic, or tricyclic aromatic hydrocarbon ring system. Examples of aryl moieties include, but are not limited to, phenyl, naphthyl, and anthracenyl.

The terms "arylalkyl" or "aralkyl" refer to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

The term "carbocyclyl" refers to a non-aromatic, monocyclic, bicyclic, or tricyclic hydrocarbon ring system. Carbocyclyl groups include fully saturated ring systems (e.g., cycloalkyls), and partially saturated ring systems.

The term "cycloalkyl" as employed herein includes saturated cyclic, bicyclic, tricyclic, or polycyclic hydrocarbon groups having 3 to 12 carbons. Any ring atom can be substituted (e.g., by one or more substituents). Examples of cycloalkyl moieties include, but are not limited to, cyclopropyl, cyclohexyl, methylcyclohexyl, adamantyl, and norbornyl.

The term "heteroaryl" refers to a fully aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms selected independently from N, O, or S if monocyclic, bicyclic, or tricyclic, respectively).

The term "heterocyclyl" refers to a nonaromatic, 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). The heteroatom may optionally be the point of attachment of the heterocyclyl substituent. Examples of heterocyclyl include, but are not limited to, tetrahydrofuranyl, tetrahydropyranyl, piperidinyl, morpholino, pyrrolinyl, pyrimidinyl, and pyrrolidinyl.

Bicyclic and tricyclic ring systems containing one or more heteroatoms and both aromatic and non-aromatic rings are considered to be heterocyclyl groups according to the present definition. Such bicyclic or tricyclic ring systems may be alternately characterized as being an aryl or a heteroaryl fused to a carbocyclyl or heterocyclyl, particularly in those instances where the ring bound to the rest of the molecule is required to be aromatic.

The terms "heteroarylalkyl" and "heteroaralkyl", as used herein, refers to an alkyl group substituted with a heteroaryl group.

The term "heterocyclylalkyl", as used herein, refers to an alkyl group substituted with a heterocyclyl group.

All ring systems (i.e., aryl, heteroaryl, carbocyclyl, cycloalkyl, heterocyclyl, etc.) or ring system portions of groups (e.g., the aryl portion of an aralkyl group) are optionally substituted at one or more substitutable carbon atoms with substituents independently selected from: halo, —C≡N, $C_1$-$C_4$ alkyl, =O, $C_3$-$C_7$ cycloalkyl, $C_1$-$C_4$ alkyl, —OH, —O—($C_1$-$C_4$ alkyl)-, —SH, —S—($C_1$-$C_4$ alkyl), —($C_1$-$C_4$ alkyl)-N($R^b$)($R^b$), —N($R^b$)($R^b$), —O—($C_1$-$C_4$ alkyl)-N($R^b$)($R^b$), —($C_1$-$C_4$ alkyl)-O—($C_1$-$C_4$ alkyl)-N($R^b$)($R^b$), —C(O)—N($R^b$)($R^b$), —($C_1$-$C_4$ alkyl)-C(O)—N($R^b$)($R^b$), —O-(heteroaryl), —O-(heterocycle), —O-phenyl, -heteroaryl, -heterocycle, and -phenyl, wherein:

each $R^b$ is independently selected from hydrogen, and —$C_1$-$C_4$ alkyl; or
  two $R^b$ are taken together with the nitrogen atom to which they are bound to form a 4- to 8-membered saturated heterocycle optionally comprising one additional heteroatom selected from N, S, S(=O), S(=O)$_2$, and O,
  any alkyl substituent is optionally further substituted with one or more of —OH, —O—($C_1$-$C_4$ alkyl), halo, —NH$_2$, —NH($C_1$-$C_4$ alkyl), or —N($C_1$-$C_4$ alkyl)$_2$; and
  any carbon atom on a phenyl, cycloalkyl, heteroaryl or heterocycle substituent is optionally further substituted with one or more of —($C_1$-$C_4$ alkyl), —($C_1$-$C_4$ fluoroalkyl), —OH, —O—($C_1$-$C_4$ alkyl), —O—($C_1$-$C_4$ fluoroalkyl), halo, —NH$_2$, —NH($C_1$-$C_4$ alkyl), or —N($C_1$-$C_4$ alkyl)$_2$;

All heterocyclyl ring systems (and any heterocyclyl substituents on any ring system) is optionally substituted on one or more any substitutable nitrogen atom with —$C_1$-$C_4$ alkyl, or fluoro-substituted $C_1$-$C_4$ alkyl.

The term "substituted" refers to the replacement of a hydrogen atom by another group.

The term "oxo" refers to an oxygen atom, which forms a carbonyl when attached to carbon, an N-oxide when attached to nitrogen, and a sulfoxide or sulfone when attached to sulfur.

The term "selective" in association with a PKM2 activator is meant at least 2-fold, 3-fold, 4-fold, 5-fold, 6-fold, or 10-fold greater activation of PKM2 than PKM1.

The term "activator" of pyruvate kinase R as used herein means an agent that (measurably) increases the activity of wild type pyruvate kinase R (wtPKR) or causes wild type pyruvate kinase R (wt PKR) activity to increase to a level that is greater than wt PKR's basal levels of activity or an agent that (measurably) increases the activity of a mutant pyruvate kinase R (mPKR) or causes mutant pyruvate kinase R (mPKR) activity to increase to a level that is greater than that mutant PKR's basal levels of activity, for examples, to a level that is 20%, 40%, 50%, 60%, 70%, 80%, 90% or 100% of the activity of wild type PKR.

The term "activator" of pyruvate kinase M2 as used herein means an agent that (measurably) increases the activity of PKM2 or causes PKM2 activity to increase to a level that is greater than PKM2's basal levels of activity. For example, the activator may mimic the effect caused by a natural ligand (e.g., FBP). The activator effect caused by a compound provided herein may be to the same, or to a greater, or to a lesser extent than the activating effect caused by a natural ligand, but the same type of effect is caused. A compound provided herein can be evaluated to determine if it is an activator by measuring either directly or indirectly the activity of the pyruvate kinase when subjected to said compound. The activity of PKM2 can be measured, for example, by monitoring the concentration of a substrate such as ATP or NADH.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

Compounds

Provided herein is a compound of Formula (I) or a pharmaceutically acceptable salt, solvate or hydrate thereof as described above in the Summary of the Invention, e.g., useful for activating wild type PKR and/or various mutant PKRs such as those mutants described herein, and/or useful for selectively activating PKM2.

In one embodiment, provided herein is a compound of Formula (I):

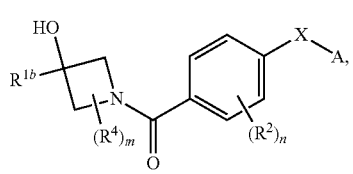
(I)

or a pharmaceutically acceptable salt thereof, wherein:

A is aryl or heteroaryl, wherein the aryl or heteroaryl is optionally substituted, and the aryl or heteroaryl is optionally fused to an optionally substituted carbocyclyl or an optionally substituted heterocyclyl;

X is selected from —NH—S(O)$_2$—, —N(alkyl)-S(O)$_2$—, —S(O)$_2$—NH— and —S(O)$_2$—N(alkyl)-;

$R^{1b}$ is C$_{2-8}$ alkyl, cycloalkyl, aryl, heteroaryl, cycloalkylalkyl, aralkyl or heteroaralkyl, wherein each aryl is substituted and each C$_{2-8}$ alkyl, cycloalkyl, cycloalkylalkyl, aralkyl, heteroaryl or heteroaralkyl is optionally substituted;

each R$^2$ is independently selected from halo and haloalkyl;

each R$^4$ is independently selected from alkyl, alkoxy, haloalkyl and hydroxyl;

n is 0, 1 or 2; and m is 0, 1 or 2;

wherein when $R^{1b}$ is unsubstituted benzyl, X is —NH—S(O)$_2$— and A is quinolin-8-yl; then n is 1.

In one embodiment, provided is a compound of formula (I), wherein m is 0 (i.e., there are no R$^4$ substituents on the azetindinyl ring), the compound having formula (Ia):

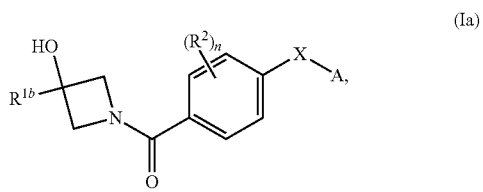
(Ia)

or a pharmaceutically acceptable salt thereof, wherein A, X, $R^{1b}$, R$^2$ and n are as described for formula (I).

In certain aspects of formula (I) or (Ia), A is an optionally substituted monocyclic heteroaryl. In a more specific aspect, A is an optionally substituted pyridyl (e.g., an optionally substituted 3-pyridyl). In an even more specific aspect, A is unsubstituted 3-pyridyl.

In certain aspects of formula (I) or (Ia), A is an optionally substituted bicyclic heteroaryl. In a more specific aspect, A is an optionally substituted quinolin-8-yl (e.g., unsubstituted quinolin-8-yl). In another more specific aspect, A is an optionally substituted quinolin-3-yl (e.g., unsubstituted quinolin-3-yl). In another more specific aspect, A is an optionally substituted isoquinolin-5-yl (e.g., unsubstituted isoquinolin-5-yl). In another more specific aspect, A is an optionally substituted benzo[1,2,5]oxadiazole (e.g., unsubstituted benzo[1,2,5]oxadiazole).

In certain aspects of formula (I) or (Ia), X is —NH—S(O)$_2$— or —N(alkyl)-S(O)$_2$—. In a more specific aspect, X is —NH—S(O)$_2$—. In an even more specific aspect of formula (I), A is an optionally substituted quinolin-8-yl and X is —NH—S(O)$_2$— and the compound has the structure set forth in formula (II) or a pharmaceutically acceptable salt thereof:

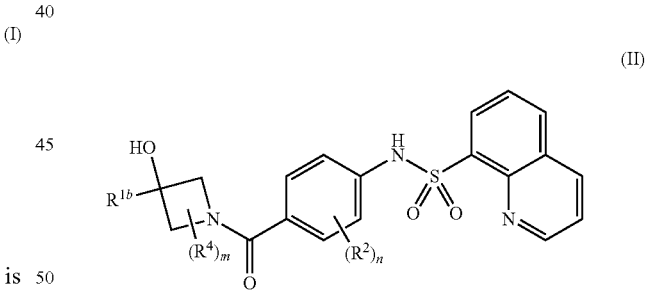
(II)

wherein $R^{1b}$, R$^2$, R$^4$, m and n are as defined for Formula (I).

In an even more specific aspect of formula (Ia), A is an optionally substituted quinolin-8-yl and X is —NH—S(O)$_2$— and the compound has the structure set forth in formula (IIa) or a pharmaceutically acceptable salt thereof:

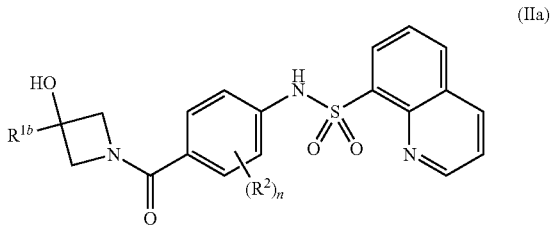
(IIa)

wherein $R^{1b}$, R$^2$, and n are as defined for Formula (Ia).

In certain embodiments of formula (I) or (Ia), A is an optionally substituted monocyclic aryl (e.g., optionally substituted phenyl). In some embodiments, A is 4-chlorophenyl. In some embodiments, A is 3-cyanophenyl. In some embodiments, A is 2-chlorophenyl. In some embodiments, A is 4-cyanophenyl. In some embodiments, A is 2-trifluoromethylphenyl. In some embodiments, A is 4-trifluoromethylphenyl. In some embodiments, A is 3-trifluoromethylphenyl. In some embodiments, A is 3-chlorophenyl. In some embodiments, A is 4-trifluoromethoxyphenyl. In some embodiments, A is 2,3-dichlorophenyl. In some embodiments, A is 2,4-difluorophenyl. In some embodiments, A is 3-trifluoromethoxyphenyl.

In certain embodiments of formula (I) or (Ia), A is phenyl substituted with two substituents on adjacent carbons which form an optionally substituted heterocyclyl or carbocyclyl ring (e.g., resulting in A comprising a bicycle). In some embodiments, A is benzo[3,4]dioxole. In some embodiments, A is 2,3-dihydrobenzo[1,4]dioxine. In some embodiments, A is a moiety of the following formula:

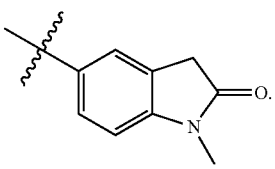 [SMILES: *c1ccc2c(c1)CC(=O)N2C]

In some embodiments A is a moiety of the following formula:

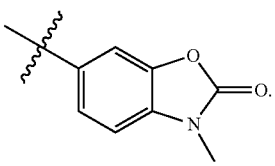 [SMILES: *c1ccc2c(c1)oc(=O)n2C]

In some embodiments of formula (I), (Ia), (II) or (IIa), $R^{1b}$ is optionally substituted aralkyl (e.g., benzyl). In some embodiments of formula (I), (Ia), (II) or (IIa), $R^{1b}$ is optionally substituted aryl (e.g., 2-methylphenyl, 2-fluorophenyl, 2-methoxyphenyl, 2-trifluoromethylphenyl, 3-methoxyphenyl, 3-trifluoromethoxyphenyl, 3-trifluoromethylphenyl, 2-trifluoromethoxyphenyl, 3-chlorophenyl, 2-chlorophenyl, 3-fluorophenyl, 2-ethylphenyl, 4-fluorophenyl or 2-methyl-4-fluorophenyl). In some embodiments of formula (I), (Ia), (II) or (IIa), $R^{1b}$ is optionally substituted heteroaralkyl (e.g., methyl-2-pyridyl, 3-methyl-methyl-2-pyridyl or 3-fluoromethyl-2-pyridyl). In some embodiments of formula (I), (Ia), (II) or (IIa), $R^{1b}$ is optionally substituted heteroaryl (e.g., 2-methoxy-3-pyridyl, 6-methoxy-2-pyridyl, 6-fluoro-2-pyridyl, 6-methyl-2-pyridyl, 2-methyl-3-pyridyl, 6-chloro-2-pyridyl, 6-trifluoromethyl-2-pyridyl, 2-fluoro-3-pyridyl, 2-trifluoromethyl-3-pyridyl or 6-difluoromethyl-2-pyridyl). In some embodiments of formula (I), (Ia), (II) or (IIa), $R^{1b}$ is optionally substituted $C_{2-8}$ alkyl (e.g., ethyl, n-propyl, isopropyl, t-butyl, isobutyl, n-butyl, 2-hydroxyethyl, 1-hydroxyethyl, 3-hydroxypropyl or 2-hydroxypropyl). In some embodiments of formula (I), (Ia), (II) or (IIa), $R^{1b}$ is optionally substituted cycloalkyl (e.g., cyclopropyl). In some embodiments of formula (I), (Ia), (II) or (IIa), $R^{1b}$ is optionally substituted cycloalkylalkyl (e.g., methylcyclopropyl).

In yet another embodiment, the compound is selected from any one of the compounds set forth in Table 1, below:

TABLE 1

Exemplary Compounds of Formula I:

| Compound # | Structure |
|---|---|
| 15 | 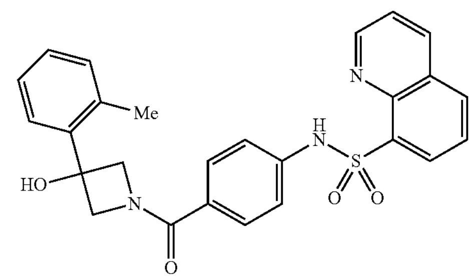 [SMILES: Cc1ccccc1C1(O)CN(C(=O)c2ccc(NS(=O)(=O)c3cccc4cccnc34)cc2)C1] |
| 55 | 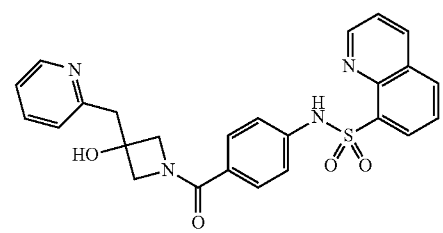 [SMILES: O=C(c1ccc(NS(=O)(=O)c2cccc3cccnc23)cc1)N1CC(O)(Cc2ccccn2)C1] |
| 45 | 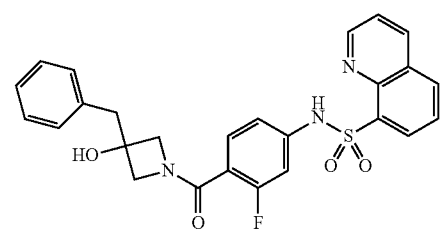 [SMILES: O=C(c1ccc(NS(=O)(=O)c2cccc3cccnc23)cc1F)N1CC(O)(Cc2ccccc2)C1] |
| 46 | 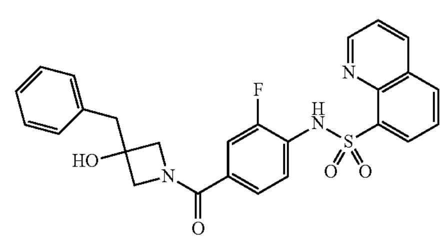 [SMILES: O=C(c1ccc(NS(=O)(=O)c2cccc3cccnc23)c(F)c1)N1CC(O)(Cc2ccccc2)C1] |
| 3 | 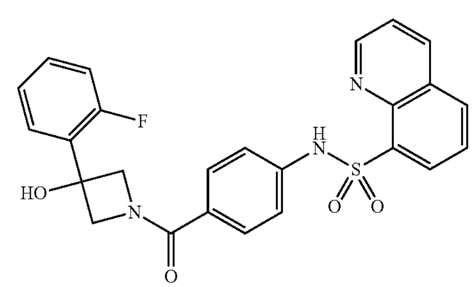 [SMILES: O=C(c1ccc(NS(=O)(=O)c2cccc3cccnc23)cc1)N1CC(O)(c2ccccc2F)C1] |

TABLE 1-continued

Exemplary Compounds of Formula I:

| Compound # | Structure |
|---|---|
| 20 | (structure) |
| 57 | (structure) |
| 58 | (structure) |
| 2 | (structure) |
| 21 | (structure) |
| 22 | (structure) |
| 6 | (structure) |
| 59 | (structure) |
| 49 | (structure) |
| 60 | (structure) |
| 51 | (structure) |
| 61 | (structure) |
| 19 | (structure) |
| 10 | (structure) |

TABLE 1-continued
Exemplary Compounds of Formula I:
| Compound # | Structure |
|---|---|
| 9 | 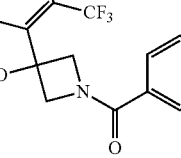 |
| 7 | 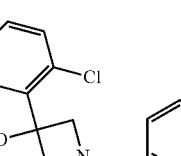 |
| 23 | 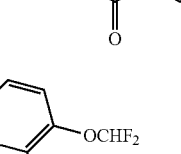 |
| 24 | 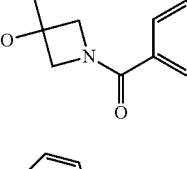 |
| 50 | 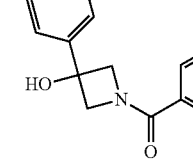 |
| 18 | 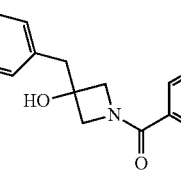 |
| 11 | 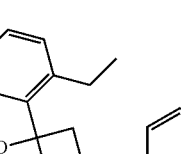 |
| 17 | 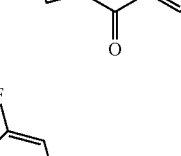 |
| 5 | 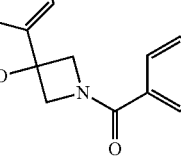 |
| 25 |  |
| 4 | |
| 62 | |
| 13 | |
| 14 | |

TABLE 1-continued
Exemplary Compounds of Formula I:
| Compound # | Structure |
|---|---|
| 56 | 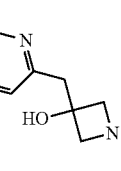 |
| 63 | |
| 64 | |
| 65 | |
| 12 | |
| 34 | |
| 36 | |
| 32 | 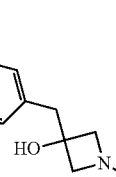 |
| 48 | 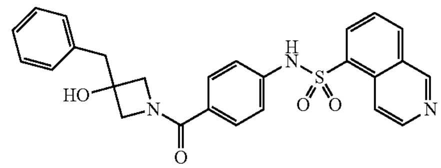 [SMILES: O=C(c1ccc(NS(=O)(=O)c2cccc3cnccc23)cc1)N1CC(O)(Cc2ccccc2)C1] |
| 52 | 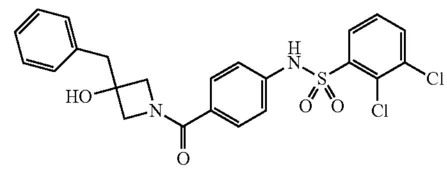 [SMILES: O=C(c1ccc(NS(=O)(=O)c2cccc(Cl)c2Cl)cc1)N1CC(O)(Cc2ccccc2)C1] |
| 66 | 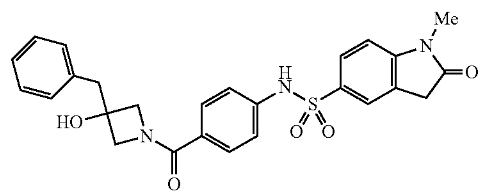 [SMILES: CN1C(=O)Cc2cc(S(=O)(=O)Nc3ccc(C(=O)N4CC(O)(Cc5ccccc5)C4)cc3)ccc21] |
| 54 | 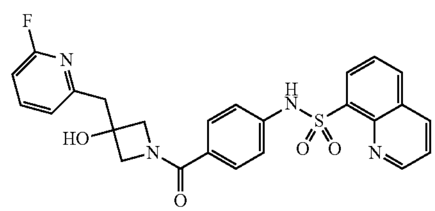 [SMILES: O=C(c1ccc(NS(=O)(=O)c2cccc3cccnc23)cc1)N1CC(O)(Cc2cccc(F)n2)C1] |
| 37 | 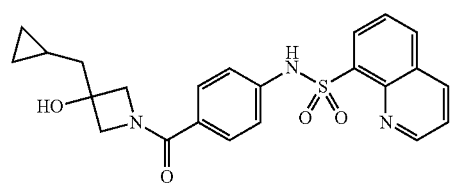 [SMILES: O=C(c1ccc(NS(=O)(=O)c2cccc3cccnc23)cc1)N1CC(O)(CC2CC2)C1] |
| 33 | 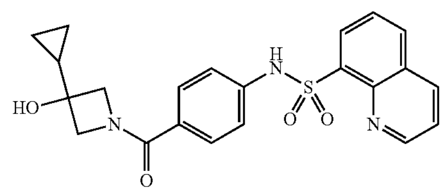 [SMILES: O=C(c1ccc(NS(=O)(=O)c2cccc3cccnc23)cc1)N1CC(O)(C2CC2)C1] |
| 31 | 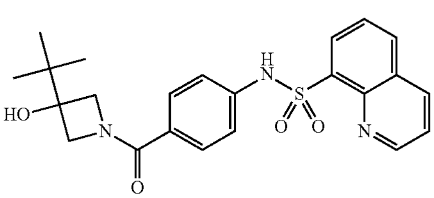 [SMILES: CC(C)(C)C1(O)CN(C(=O)c2ccc(NS(=O)(=O)c3cccc4cccnc34)cc2)C1] |

TABLE 1-continued

Exemplary Compounds of Formula I:

| Compound # | Structure |
|---|---|
| 35 | 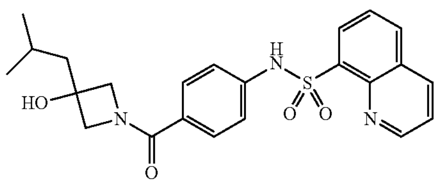 [SMILES: CC(C)CC1(O)CN(C(=O)c2ccc(NS(=O)(=O)c3cccc4cccnc34)cc2)C1] |
| 42 | 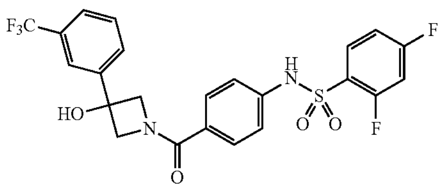 [SMILES: O=C(c1ccc(NS(=O)(=O)c2ccc(F)cc2F)cc1)N1CC(O)(c2cccc(C(F)(F)F)c2)C1] |
| 67 | 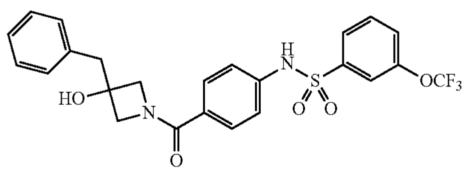 [SMILES: O=C(c1ccc(NS(=O)(=O)c2cccc(OC(F)(F)F)c2)cc1)N1CC(O)(Cc2ccccc2)C1] |
| 68 | 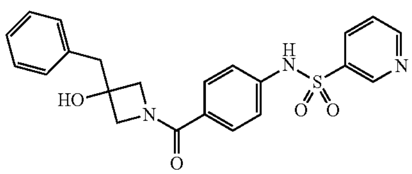 [SMILES: O=C(c1ccc(NS(=O)(=O)c2cccnc2)cc1)N1CC(O)(Cc2ccccc2)C1] |
| 44 | 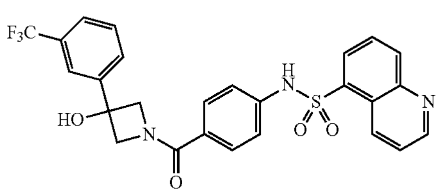 [SMILES: O=C(c1ccc(NS(=O)(=O)c2cccc3ncccc23)cc1)N1CC(O)(c2cccc(C(F)(F)F)c2)C1] |
| 43 | 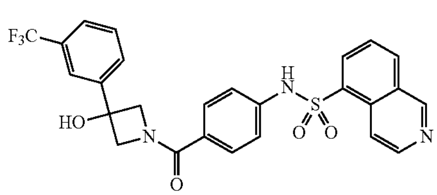 |
| 16 | 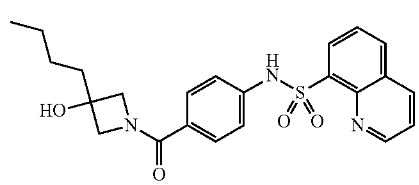 [SMILES: CCCCC1(O)CN(C(=O)c2ccc(NS(=O)(=O)c3cccc4cccnc34)cc2)C1] |
| 53 | 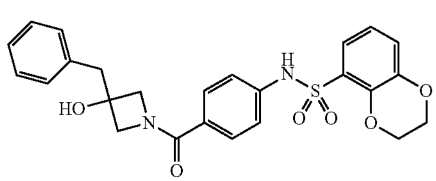 [SMILES: O=C(c1ccc(NS(=O)(=O)c2cccc3c2OCCO3)cc1)N1CC(O)(Cc2ccccc2)C1] |
| 69 | |
| 70 | |
| 38 | |
| 39 | |
| 40 | |
| 41 | |

Compounds described herein are useful as activators of PKR mutants having lower activities compared to the wild type, thus are useful for methods of the present invention. Such mutations in PKR can affect enzyme activity (catalytic efficiency), regulatory properties (modulation by fructose bisphosphate (FBP)/ATP), and/or thermostability of the enzyme. Examples of such mutations are described in Valentini et al, JBC 2002. Some examples of the mutants that are activated by the compounds described herein include G332S, G364D, T384M, G37E, R479H, R479K, R486W, R532W, R510Q, and R490W. Without being bound by theory, compounds described herein affect the activities of PKR mutants by activating FBP non-responsive PKR mutants, restoring thermostability to mutants with decreased stability, or restoring catalytic efficiency to impaired mutants. The activating activity of the present compounds against PKR mutants may be tested following a method described in Example 8. Compounds described herein are also useful as activators of wild type PKR.

In an embodiment, to increase the lifetime of the red blood cells, a compound, composition or pharmaceutical composition described herein is added directly to whole blood or packed cells extracorporeally or be provided to the patient directly (e.g., by i.p., i.v., i.m., oral, inhalation (aerosolized delivery), transdermal, sublingual and other delivery routes). Without being bound by theory, compounds described herein increase the lifetime of the RBCs, thus counteract aging of stored blood, by impacting the rate of release of 2,3-DPG from the blood. A decrease in the level of 2,3-DPG concentration induces a leftward shift of the oxygen-hemoglobin dissociation curve and shifts the allosteric equilibribrium to the R, or oxygenated state, thus producing a therapeutic inhibition of the intracellular polymerization that underlies sickling by increasing oxygen affinity due to the 2,3-DPG depletion, thereby stabilizing the more soluble oxy-hemoglobin. Accordingly, in one embodiment, compounds and pharmaceutical compositions described herein are useful as antisickling agents. In another embodiment, to regulate 2,3-diphosphoglycerate, a compound, composition or pharmaceutical composition described herein is added directly to whole blood or packed cells extracorporeally or be provided to the patient directly (e.g., by i.p., i.v., i.m., oral, inhalation (aerosolized delivery), transdermal, sublingual and other delivery routes).

A compound described herein may be an activator of a PKR, for example, a wild type (wt), mutated PKR (e.g., R510Q, or R532W). Activities of exemplary compounds against wt PKR (in an enzymatic or cell based assay) and mutant PKRs are shown in Table 2 as measured by assays in Examples 2-5 below. As shown in Table 2, AA refers to an AC50 less than 100 nM, BB refers to an AC50 from 101 nM to 1.00 μM, CC refers to an AC50 from than 1.01 μM to 10.00 μM, DD refers to an AC50 greater than 10.01 μM and EE refers to an AC50 that is not available.

TABLE 2

| Compound # | PKR R510Q AC50 (μM) | PKR R532W AC50 (μM) | PKR WT AC50 (μM) | PKR WT Cell Based AC50 (μM) |
|---|---|---|---|---|
| 15 | BB | AA | AA | BB |
| 55 | CC | BB | BB | EE |
| 45 | CC | BB | BB | EE |
| 46 | CC | BB | BB | EE |
| 3 | CC | BB | BB | EE |
| 20 | BB | BB | BB | BB |
| 57 | EE | EE | EE | EE |
| 58 | EE | EE | EE | EE |
| 2 | BB | AA | AA | BB |
| 21 | CC | EE | CC | EE |
| 22 | CC | BB | BB | EE |
| 6 | BB | BB | BB | EE |
| 59 | DD | EE | EE | EE |
| 49 | DD | CC | CC | EE |
| 60 | EE | EE | EE | EE |
| 51 | DD | DD | DD | EE |
| 61 | BB | AA | AA | AA |
| 19 | BB | AA | BB | BB |
| 10 | BB | AA | AA | BB |
| 9 | AA | AA | AA | AA |
| 7 | BB | AA | BB | BB |
| 23 | DD | EE | CC | EE |
| 24 | CC | EE | BB | EE |
| 50 | EE | DD | EE | EE |
| 18 | CC | BB | BB | EE |

TABLE 2-continued

| Compound # | PKR R510Q AC50 (μM) | PKR R532W AC50 (μM) | PKR WT AC50 (μM) | PKR WT Cell Based AC50 (μM) |
|---|---|---|---|---|
| 11 | BB | AA | AA | BB |
| 17 | BB | EE | AA | BB |
| 5 | BB | AA | AA | BB |
| 25 | CC | EE | BB | EE |
| 4 | CC | BB | BB | AA |
| 62 | EE | EE | EE | EE |
| 13 | BB | EE | AA | AA |
| 14 | CC | BB | BB | EE |
| 56 | DD | BB | CC | EE |
| 63 | EE | EE | EE | EE |
| 64 | EE | EE | EE | EE |
| 65 | EE | DD | DD | EE |
| 12 | BB | AA | AA | BB |
| 34 | DD | CC | CC | EE |
| 36 | DD | CC | BB | EE |
| 32 | DD | CC | CC | EE |
| 48 | EE | DD | DD | EE |
| 52 | DD | CC | CC | EE |
| 66 | EE | DD | DD | EE |
| 54 | CC | BB | BB | EE |
| 37 | DD | BB | BB | EE |
| 33 | DD | CC | CC | EE |
| 31 | DD | CC | CC | EE |
| 35 | CC | BB | BB | EE |
| 42 | DD | DD | DD | EE |
| 67 | EE | EE | EE | EE |
| 68 | EE | EE | EE | EE |
| 44 | CC | CC | CC | EE |
| 43 | DD | CC | CC | EE |
| 16 | BB | BB | AA | BB |
| 53 | AA | AA | AA | AA |
| 69 | DD | DD | DD | EE |
| 70 | DD | DD | DD | EE |
| 38 | DD | DD | CC | EE |
| 39 | DD | DD | DD | EE |
| 40 | DD | CC | CC | EE |
| 41 | DD | CC | CC | EE |

The compounds described herein can be made using a variety of synthetic techniques, general and specific examples of which are set forth in Example section.

As can be appreciated by the skilled artisan, methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds provided herein may contain one or more asymmetric centers and thus occur as racemates and racemic mixtures, single enantiomers, individual diastereomers and diastereomeric mixtures. All such isomeric forms of these compounds are expressly included within the scope. Unless otherwise indicated when a compound is named or depicted by a structure without specifying the stereochemistry and has one or more chiral centers, it is understood to represent all possible stereoisomers of the compound. The compounds provided herewith may also contain linkages (e.g., carbon-carbon bonds) or substituents that can restrict bond rotation, e.g., restriction resulting from the presence of a ring or double bond. Accordingly, all cis/trans and E/Z isomers are expressly included.

The compounds provided herein (e.g., of Formula I) may also comprise one or more isotopic substitutions. For example, H may be in any isotopic form, including $^1$H, $^2$H (D or deuterium), and $^3$H (T or tritium); C may be in any isotopic form, including $^{12}$C, $^{13}$C, and $^{14}$C; O may be in any isotopic form, including $^{16}$O and $^{18}$O; and the like. The compounds provided herein may also be represented in multiple tautomeric forms, in such instances, expressly includes all tautomeric forms of the compounds described herein, even though only a single tautomeric form may be represented (e.g., alkylation of a ring system may result in alkylation at multiple sites; all such reaction products are expressly included). All such isomeric forms of such compounds are expressly included. All crystal forms of the compounds described herein are expressly included.

The compounds provided herein include the compounds themselves, as well as their salts and their prodrugs, if applicable. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion. Examples of prodrugs include esters and other pharmaceutically acceptable derivatives, which, upon administration to a subject, are capable of providing active compounds.

The compounds provided herein may be modified by appending appropriate functionalities to enhance selected biological properties, e.g., targeting to a particular tissue. Such modifications are known in the art and include those which increase biological penetration into a given biological compartment (e.g., blood, lymphatic system, central nervous system), increase oral availability, increase solubility to allow administration by injection, alter metabolism and alter rate of excretion.

In an alternate embodiment, the compounds described herein may be used as platforms or scaffolds that may be utilized in combinatorial chemistry techniques for preparation of derivatives and/or chemical libraries of compounds. Such derivatives and libraries of compounds have biological activity and are useful for identifying and designing compounds possessing a particular activity. Combinatorial techniques suitable for utilizing the compounds described herein are known in the art as exemplified by Obrecht, D. and Villalgrodo, J. M., *Solid-Supported Combinatorial and Parallel Synthesis of Small-Molecular-Weight Compound Libraries*, Pergamon-Elsevier Science Limited (1998), and include those such as the "split and pool" or "parallel" synthesis techniques, solid-phase and solution-phase techniques, and encoding techniques (see, for example, Czarnik, A. W., *Curr. Opin. Chem. Bio.*, (1997) 1, 60. Thus, one embodiment relates to a method of using the compounds described herein for generating derivatives or chemical libraries comprising: 1) providing a body comprising a plurality of wells; 2) providing one or more compounds identified by methods described herein in each well; 3) providing an additional one or more chemicals in each well; 4) isolating the resulting one or more products from each well. An alternate embodiment relates to a method of using the compounds described herein for generating derivatives or chemical libraries comprising: 1) providing one or more compounds described herein attached to a solid support; 2) treating the one or more compounds identified by methods described herein attached to a solid support with one or more additional chemicals; 3) isolating the resulting one or more products from the solid support. In the methods described above, "tags" or identifier or labeling moieties may be attached to and/or detached from the compounds described herein or their derivatives, to facilitate tracking, identification or isolation of the desired products or their intermediates. Such moieties are known in the art. The chemicals used in the aforementioned methods may include, for example, solvents, reagents, catalysts, protecting group and deprotecting group reagents and the like. Examples of such chemicals are those that appear in the various synthetic and protecting group chemistry texts and treatises referenced herein.

Methods of Evaluating Compounds

The compounds described herein can be evaluated for ability to modulate PKM2 (e.g., activate PKM2) by methods known in the art. In some embodiments, compounds described herein are evaluated for ability to modulate PKM2 (e.g., activate PKM2) in serine deficient conditions. In some embodiments, exemplary methods include contacting the compound with a cell-based assay which allows assessment of the ability to modulate (e.g., activate) PKM2. E.g., the candidate compound can be contacted with a cell and measuring the consumption of oxygen or production of lactate. A change in cellular phosphoenolpyruvate, a change in glycerol-phosphate, a change in ribose or deoxyribose, a change in lipid synthesis, or a change in glucose conversion to lipid or nucleic acids or amino acids or protein can also be used to evaluate a compound for its ability to modulate PKM2 (e.g., activate PKM2). The evaluation could also include measuring a change in pyruvate or a determination of an alteration in mitochondrial membrane potential, e.g., as measured by fluorescent potentiometric dyes.

PKM1 and PKM2 for use in the screening/testing method may be produced by any method known in the art for expression of recombinant proteins. For example, nucleic acids that encode the desired polypeptide may be introduced into various cell types or cell-free systems for expression. Eukaryotic (e.g., COS, HEK293T, CHO, and NIH cell lines) and prokaryotic (e.g., *E. coli*) expression systems may be generated in which a PKM sequence is introduced into a plasmid or other vector, which is then used to transform living cells. Constructs in which the PKM cDNA contains the entire open reading frame, or biologically active fragment thereof, are inserted in the correct orientation into an expression plasmid and may be used for protein expression. Prokaryotic and eukaryotic expression systems allow for the expression and recovery of fusion proteins in which the PKM protein is covalently linked to a tag molecule on either the amino terminal or carboxy terminal side, which facilitates identification and/or purification. Examples of tags that can be used include hexahistidine, HA, FLAG, and c-myc epitope tags. An enzymatic or chemical cleavage site can be engineered between the PKM protein and the tag molecule so that the tag can be removed following purification.

The activity of the PKM enzyme measured in the screening/testing assay may be measured by, e.g., monitoring the concentration of a substrate (e.g., ATP or NADH) present in the reaction mixture. Pyruvate, produced by the enzymatic activity of pyruvate kinase, is converted into lactate by lactate dehydrogenase, which requires the consumption of NADH (NADH→NAD+). Thus, the activity of PKM2 can be indirectly measured by monitoring the consumption of NADH through, e.g., fluorescence assays. Additionally, the activity of the PKM2 enzyme can be directly monitored by measuring the production of ATP, as ATP is produced when phosphoenolpyruvate is converted to pyruvate. Methods for monitoring the amount of substrate in a reaction mixture include, e.g., absorbance, fluorescence, Raman scattering, phosphorescence, luminescence, luciferase assays, and radioactivity.

The screening procedure requires the presence of specific components in the reaction mixture. Components utilized in the assay include, e.g., a nucleoside diphosphate (e.g., ADP), phosphoenolpyruvate, NADH, lactate dehydrogenase, FBP, a reducing agent (e.g., dithiothreitol), a detergent (e.g., Brij 35), glycerol, and a solvent (e.g., DMSO). Exemplary reaction conditions are found in Table 1.

TABLE 1

| Component of Reaction Condition | Amount in Activation Assay |
| --- | --- |
| ADP | 0.1-5.0 mM |
| Phosphoenolpyruvate | 0.1-5.0 mM |
| NADH | 10-1000 μM |
| Lactate dehydrogenase | 0.1-10 units |
| Fructose-1,6-bisphosphate | 0 |
| DTT | 0.1-50 mM |
| Brij 35 | 0.01-1% |
| Glycerol | 0.1-10% |
| Pyruvate Kinase M2 (used for screen) | 1-100 pg |
| DMSO | 1-10% |

Compounds useful as PKM2 activators are those that demonstrate specificity and activation of PKM2 enzyme in the absence of FBP to a level greater than that of 10, 15, 20, 25, 30, 35, 40, 45, 50, 55, 60, 65, 70, 75, 80, 85, 90, 95, 99, or 100% in the presence of FBP. Furthermore, compounds can be evaluated in the presence or absence of a phosphotyrosine peptide. Phosphotyrosine peptide binding to PKM2 leads to a dissociation of FBP from PKM2 and conformational changes of PKM2 from an active, tetrameric form to an inactive form. Compounds that bind to PKM2 and lock the enzyme in the active confirmation even in the presence of a phosphotyrosine peptide will lead to the loss of allosteric control of PKM2 needed for shunting the biochemical intermediates from glycolysis into biosynthesis of other intermediates. This, in turn, will lead to inhibition of growth of cancer cells, activated immune cells and fat cells.

Methods of Treatment

In one embodiment, provided is a method for treating or preventing a disease, condition or disorder as described herein (e.g., treating) comprising administering a compound, a pharmaceutically acceptable salt of a compound or pharmaceutical composition comprising a compound described herein (e.g., a compound of formula (I), (II), or in FIG. 1).

The compounds and compositions described herein can be administered to cells in culture, e.g., in vitro or ex vivo, or to a subject, e.g., in vivo, to treat, prevent, and/or diagnose a variety of disorders, including those described herein below.

As used herein, the term "treat" or "treatment" is defined as the application or administration of a compound, alone or in combination with, a second therapeutic agent to a subject, e.g., a patient, or application or administration of the compound to an isolated tissue or cell, e.g., cell line, from a subject, e.g., a patient, who has a disorder (e.g., a disorder as described herein), a symptom of a disorder, with the purpose to cure, heal, alleviate, relieve, alter, remedy, ameliorate, improve or affect the disorder, or one or more symptoms of the disorder.

As used herein, an amount of a compound effective to treat a disorder, or a "therapeutically effective amount" refers to an amount of the compound which is effective, upon single or multiple dose administration to a subject, in treating a cell, or in curing, alleviating, relieving or improving a subject with a disorder beyond that expected in the absence of such treatment.

As used herein, the term "prevent" is defined as the application or administration of a compound, alone or in combination with, a second therapeutic agent to a subject, e.g., a patient, or application or administration of the compound to an isolated tissue or cell, e.g., cell line, from a subject, e.g., a patient, who has a predisposition toward a disorder, with the purpose to prevent the occurrence of at least one symptom of the disorder or to delay onset of at least one symptom of the disorder).

As used herein, an amount of a compound effective to prevent a disorder, or a "a prophylactically effective amount" of the compound refers to an amount effective, upon single- or multiple-dose administration to the subject, in preventing or delaying the occurrence of the onset or recurrence of a disorder or a symptom of the disorder.

As used herein, the term "subject" is intended to include human and non-human animals. Exemplary human subjects include a human patient having a disorder, e.g., a disorder described herein or a normal subject. The term "non-human animals" includes all vertebrates, e.g., non-mammals (such as chickens, amphibians, reptiles) and mammals, such as non-human primates, domesticated and/or agriculturally useful animals, e.g., sheep, dog, cat, cow, pig, etc.

Blood Related Conditions

A compound or composition described herein can be used to treat a blood related condition. In one embodiment, provided is a method for increasing lifetime of the red blood cells (RBCs) in need thereof comprising contacting blood with an effective amount of (1) a compound disclosed herein or a pharmaceutically acceptable salt, solvate or hydrate thereof; (2) a composition comprising a compound disclosed herein or a salt, solvate or hydrate thereof and a carrier; or (3) a pharmaceutical composition comprising a compound disclosed herein or a pharmaceutically acceptable salt, solvate or hydrate thereof, and a pharmaceutically acceptable carrier.

In another embodiment, provided is a method for regulating 2,3-diphosphoglycerate levels in blood in need thereof comprising contacting blood with an effective amount of (1) a compound disclosed herein or a pharmaceutically acceptable salt, solvate or hydrate thereof; (2) a composition comprising a compound disclosed herein or a salt, solvate or hydrate thereof and a carrier; or (3) a pharmaceutical composition comprising a compound disclosed herein or a pharmaceutically acceptable salt, solvate or hydrate thereof, and a pharmaceutically acceptable carrier.

In another embodiment, provided is a method for treating hereditary non-spherocytic haemolytic anemia comprising administering to a subject in need thereof a therapeutically effective amount of (1) a compound disclosed herein or a pharmaceutically acceptable salt, solvate or hydrate thereof; (2) a pharmaceutical composition comprising a compound disclosed herein or a pharmaceutically acceptable salt, solvate or hydrate thereof, and a pharmaceutically acceptable carrier.

In another embodiment, provided is a method for treating sickle cell anemia comprising administering to a subject in need thereof a therapeutically effective amount of (1) a compound disclosed herein or a pharmaceutically acceptable salt, solvate or hydrate thereof; (2) a pharmaceutical composition comprising a compound disclosed herein or a pharmaceutically acceptable salt, solvate or hydrate thereof, and a pharmaceutically acceptable carrier.

In another embodiment, provided is a method for treating hemolytic anemia (e.g., chronic hemolytic anemia caused by phosphoglycerate kinase deficiency, Blood Cells Mol Dis, 2011; 46(3):206) comprising administering to a subject in need thereof a therapeutically effective amount of (1) a compound disclosed herein or a pharmaceutically acceptable salt, solvate or hydrate thereof; (2) a pharmaceutical composition comprising a compound disclosed herein or a pharmaceutically acceptable salt, solvate or hydrate thereof, and a pharmaceutically acceptable carrier.

In another embodiment, provided is a method for treating diseases or conditions that are associated with increased 2,3-diphosphoglycerate levels (e.g., liver diseases (Am J Gastroenterol, 1987; 82(12):1283) and Parkinson's (J. Neurol, Neurosurg, and Psychiatry 1976, 39:952) comprising administering to a subject in need thereof a therapeutically effective amount of (1) a compound disclosed herein or a pharmaceutically acceptable salt, solvate or hydrate thereof; (2) a pharmaceutical composition comprising a compound disclosed herein or a pharmaceutically acceptable salt, solvate or hydrate thereof, and a pharmaceutically acceptable carrier.

In another embodiment, provided is a method for treating thalassemia (e.g., beta-thalassemia), hereditary spherocytosis, hereditary elliptocytosis, abetalipoproteinemia (or Bassen-Kornzweig syndrome), paroxysmal nocturnal hemoglobinuria, acquired hemolytic anemia (e.g., congenital anemias (e.g., enzymopathies)), or anemia of chronic diseases comprising administering to a subject in need thereof a therapeutically effective amount of (1) a compound disclosed herein or a pharmaceutically acceptable salt, solvate or hydrate thereof; (2) a pharmaceutical composition comprising a compound disclosed herein or a pharmaceutically acceptable salt, solvate or hydrate thereof, and a pharmaceutically acceptable carrier.

In another embodiment, provided is a method for treating diseases or conditions that are associated with increased 2,3-diphosphoglycerate levels (e.g., liver diseases (Am J Gastroenterol, 1987; 82(12):1283) and Parkinson's (J. Neurol, Neurosurg, and Psychiatry 1976, 39:952) comprising administering to a subject in need thereof a therapeutically effective amount of (1) a compound disclosed herein or a pharmaceutically acceptable salt, solvate or hydrate thereof; (2) a pharmaceutical composition comprising a compound disclosed herein or a pharmaceutically acceptable salt, solvate or hydrate thereof, and a pharmaceutically acceptable carrier.

Compounds and compositions described herein are activators of PKR mutants having lower activities compared to the wild type, thus are useful for methods of the present invention. Such mutations in PKR can affect enzyme activity (catalytic efficiency), regulatory properties (modulation by fructose bisphosphate (FBP)/ATP), and/or thermostability of the enzyme. Examples of such mutations are described in Valentini et al, JBC 2002. Some examples of the mutants that are activated by the compounds described herein include G332S, G364D, T384M, G37E, R479H, R479K, R486W, R532W, R510Q, and R490W. Without being bound by theory, compounds described herein affect the activities of PKR mutants by activating FBP non-responsive PKR mutants, restoring thermostability to mutants with decreased stability, or restoring catalytic efficiency to impaired mutants. The activating activity of the present compounds against PKR mutants may be tested following a method described in Examples 2-5. Compounds described herein are also activators of wild type PKR.

In an embodiment, to increase the lifetime of the red blood cells, a compound, composition or pharmaceutical composition described herein is added directly to whole blood or packed cells extracorporeally or be provided to the subject (e.g., the patient) directly (e.g., by i.p., i.v., i.m., oral, inhalation (aerosolized delivery), transdermal, sublingual and other delivery routes). Without being bound by theory, compounds described herein increase the lifetime of the RBCs, thus counteract aging of stored blood, by impacting the rate of release of 2,3-DPG from the blood. A decrease in the level of 2,3-DPG concentration induces a leftward shift of the oxygen-hemoglobin dissociation curve and shifts the allosteric equilibribrium to the R, or oxygenated state, thus producing a therapeutic inhibition of the intracellular polymerization that underlies sickling by increasing oxygen affinity due to the 2,3-DPG depletion, thereby stabilizing the more soluble oxy-hemoglobin. Accordingly, in one embodiment, compounds and pharmaceutical compositions described herein are useful as antisickling agents.

Neoplastic Disorders

A compound or composition described herein can be used to treat a neoplastic disorder. A "neoplastic disorder" is a disease or disorder characterized by cells that have the capacity for autonomous growth or replication, e.g., an abnormal state or condition characterized by proliferative cell growth. Exemplary neoplastic disorders include: carcinoma, sarcoma, metastatic disorders (e.g., tumors arising from prostate, colon, lung, breast and liver origin), hematopoietic neoplastic disorders, e.g., leukemias, metastatic tumors. Prevalent cancers include: breast, prostate, colon, lung, liver, and pancreatic cancers. Treatment with the compound may be in an amount effective to ameliorate at least one symptom of the neoplastic disorder, e.g., reduced cell proliferation, reduced tumor mass, etc.

The disclosed methods are useful in the prevention and treatment of cancer, including for example, solid tumors, soft tissue tumors, and metastases thereof. The disclosed methods are also useful in treating non-solid cancers. Exemplary solid tumors include malignancies (e.g., sarcomas, adenocarcinomas, and carcinomas) of the various organ systems, such as those of lung, breast, lymphoid, gastrointestinal (e.g., colon), and genitourinary (e.g., renal, urothelial, or testicular tumors) tracts, pharynx, prostate, and ovary. Exemplary adenocarcinomas include colorectal cancers, renal-cell carcinoma, liver cancer, non-small cell carcinoma of the lung, and cancer of the small intestine.

Without being bound by theory, applicants believe that altered PKM2 levels characterize a subset of all types of cancers, without regard to their cellular nature or location in the body. Thus, the compounds and methods disclosed herein are useful to treat any type of cancer that is characterized by altered PKM2 levels.

Cancer Combination Therapies

In some embodiments, a compound described herein is administered together with one or more additional cancer treatments. Exemplary cancer treatments include, for example: chemotherapy, targeted therapies such as antibody therapies, immunotherapy, and hormonal therapy. Examples of each of these treatments are provided below.

Chemotherapy

In some embodiments, a compound described herein is administered with one or more chemotherapies. Chemotherapy is the treatment of cancer with drugs that can destroy cancer cells. "Chemotherapy" usually refers to cytotoxic drugs which affect rapidly dividing cells in general, in contrast with targeted therapy. Chemotherapy drugs interfere with cell division in various possible ways, e.g., with the duplication of DNA or the separation of newly formed chromosomes. Most forms of chemotherapy target all rapidly dividing cells and are not specific for cancer cells, although some degree of specificity may come from the inability of many cancer cells to repair DNA damage, while normal cells generally can.

Examples of chemotherapeutic agents used in cancer therapy include, for example, antimetabolites (e.g., folic acid, purine, and pyrimidine derivatives) and alkylating agents (e.g., nitrogen mustards, nitrosoureas, platinum, alkyl sulfonates, hydrazines, triazenes, aziridines, spindle poison, cytotoxic agents, toposimerase inhibitors and others). Exemplary agents include Aclarubicin, Actinomycin, Alitretinon, Altretamine, Aminopterin, Aminolevulinic acid, Amrubicin, Amsacrine, Anagrelide, Arsenic trioxide, Asparaginase, Atrasentan, Belotecan, Bexarotene, endamustine, Bleomycin, Bortezomib, Busulfan, Camptothecin, Capecitabine, Carboplatin, Carboquone, Carmofur, Carmustine, Celecoxib, Chlorambucil, Chlormethine, Cisplatin, Cladribine, Clofarabine, Crisantaspase, Cyclophosphamide, Cytarabine, Dacarbazine, Dactinomycin, Daunorubicin, Decitabine, Demecolcine, Docetaxel, Doxorubicin, Efaproxiral, Elesclomol, Elsamitrucin, Enocitabine, Epirubicin, Estramustine, Etoglucid, Etoposide, Floxuridine, Fludarabine, Fluorouracil (5FU), Fotemustine, Gemcitabine, Gliadel implants, Hydroxycarbamide, Hydroxyurea, Idarubicin, Ifosfamide, Irinotecan, Irofulven, Ixabepilone, Larotaxel, Leucovorin, Liposomal doxorubicin, Liposomal daunorubicin, Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nedaplatin, Nimustine, Oblimersen, Omacetaxine, Ortataxel, Oxaliplatin, Paclitaxel, Pegaspargase, Pemetrexed, Pentostatin, Pirarubicin, Pixantrone, Plicamycin, Porfimer sodium, Prednimustine, Procarbazine, Raltitrexed, Ranimustine, Rubitecan, Sapacitabine, Semustine, Sitimagene ceradenovec, Satraplatin, Streptozocin, Talaporfin, Tegafur-uracil, Temoporfin, Temozolomide, Teniposide, Tesetaxel, Testolactone, Tetranitrate, Thiotepa, Tiazofurin, Tioguanine, Tipifarnib, Topotecan, Trabectedin, Triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein.

Because some drugs work better together than alone, two or more drugs are often given at the same time. Often, two or more chemotherapy agents are used as combination chemotherapy. In some embodiments, the chemotherapy agents (including combination chemotherapy) can be used in combination with a compound described herein.

Targeted Therapy

In some embodiments, a compound described herein is administered with one or more targeted therapies. Targeted therapy constitutes the use of agents specific for the deregulated proteins of cancer cells. Small molecule targeted therapy drugs are generally inhibitors of enzymatic domains on mutated, overexpressed, or otherwise critical proteins within the cancer cell. Prominent examples are the tyrosine kinase inhibitors such as Axitinib, Bosutinib, Cediranib, dasatinib, erlotinib, imatinib, gefitinib, lapatinib, Lestaurtinib, Nilotinib, Semaxanib, Sorafenib, Sunitinib, and Vandetanib, and also cyclin-dependent kinase inhibitors such as Alvocidib and Seliciclib. Monoclonal antibody therapy is another strategy in which the therapeutic agent is an antibody which specifically binds to a protein on the surface of the cancer cells. Examples include the anti-HER2/neu antibody trastuzumab (HERCEPTIN®) typically used in breast cancer, and the anti-CD20 antibody rituximab and Tositumomab typically used in a variety of B-cell malignancies. Other exemplary anbibodies include Cetuximab, Panitumumab, Trastuzumab, Alemtuzumab, Bevacizumab, Edrecolomab, and Gemtuzumab. Exemplary fusion proteins include Aflibercept and Denileukin diftitox. In some embodiments, the targeted therapy can be used in combination with a compound described herein.

Targeted therapy can also involve small peptides as "homing devices" which can bind to cell surface receptors or affected extracellular matrix surrounding the tumor. Radionuclides which are attached to these peptides (e.g., RGDs) eventually kill the cancer cell if the nuclide decays in the vicinity of the cell. An example of such therapy includes BEXXAR®.

Immunotherapy

In some embodiments, a compound described herein is administered with one or more immunotherapies. Cancer immunotherapy refers to a diverse set of therapeutic strategies designed to induce the patient's own immune system to fight the tumor. Contemporary methods for generating an immune response against tumors include intravesicular BCG immunotherapy for superficial bladder cancer, and use of interferons and other cytokines to induce an immune response in renal cell carcinoma and melanoma patients.

Allogeneic hematopoietic stem cell transplantation can be considered a form of immunotherapy, since the donor's immune cells will often attack the tumor in a graft-versus-tumor effect. In some embodiments, the immunotherapy agents can be used in combination with a compound described herein.

Hormonal Therapy

In some embodiments, a compound described herein is administered with one or more hormonal therapies. The growth of some cancers can be inhibited by providing or blocking certain hormones. Common examples of hormone-sensitive tumors include certain types of breast and prostate cancers. Removing or blocking estrogen or testosterone is often an important additional treatment. In certain cancers, administration of hormone agonists, such as progestogens may be therapeutically beneficial. In some embodiments, the hormonal therapy agents can be used in combination with a compound described herein.

Obesity and Fat Disorders

A compound or composition described herein can be used to treat or prevent obesity, e.g., in a human subject, e.g., a child or adult subject. "Obesity" refers to a condition in which a subject has a body mass index of greater than or equal to 30. Many compounds described herein can be used to treat or prevent an over-weight condition. "Over-weight" refers to a condition in which a subject has a body mass index of greater or equal to 25.0. The body mass index (BMI) and other definitions are according to the "NIH Clinical Guidelines on the Identification and Evaluation, and Treatment of Overweight and Obesity in Adults" (1998). Treatment with the compound may be in an amount effective to alter the weight of the subject, e.g., by at least 2, 5, 7, 10, 12, 15, 20, 25, 30, 25, 40, 45, 50, or 55%. Treatment with a compound may be in an amount effective to reduce the body mass index of the subject, e.g., to less than 30, 28, 27, 25, 22, 20, or 18. The compounds can be used to treat or prevent aberrant or inappropriate weight gain, metabolic rate, or fat deposition, e.g., anorexia, bulimia, obesity, diabetes, or hyperlipidemia (e.g., elevated triglycerides and/or elevated cholesterol), as well as disorders of fat or lipid metabolism.

A compound or composition described herein can be administered to treat obesity associated with Prader-Willi Syndrome (PWS). PWS is a genetic disorder associated with obesity (e.g., morbid obesity).

A compound or composition described herein can be used to reduce body fat, prevent increased body fat, reduce cholesterol (e.g., total cholesterol and/or ratios of total cholesterol to HDL cholesterol), and/or reduce appetite in individuals having PWS associated obesity, and/or reduce comorbidities such as diabetes, cardiovascular disease, and stroke.

Compositions and Routes of Administration

The compositions delineated herein include the compounds delineated herein (e.g., a compound described herein), as well as additional therapeutic agents if present, in amounts effective for achieving a modulation of disease or disease symptoms, including those described herein.

The term "pharmaceutically acceptable carrier or adjuvant" refers to a carrier or adjuvant that may be administered to a patient, together with a compound provided herewith, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions provided herewith include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions provided herewith may be administered orally, parenterally, by inhalation spray, topically, rectally, nasally, buccally, vaginally or via an implanted reservoir, preferably by oral administration or administration by injection. The pharmaceutical compositions provided herewith may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions provided herewith may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions provided herewith may also be administered in the form of suppositories for rectal administration. These compositions can be prepared by mixing a compound provided herewith with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions provided herewith is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds provided herewith include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions provided herewith may also be topically applied to the lower intestinal tract by rectal suppository formulation or in a suitable enema formulation. Topically-transdermal patches are also included.

The pharmaceutical compositions provided herewith may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions provided herewith comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds provided herewith. Alternatively, those agents may be part of a single dosage form, mixed together with the compounds provided herewith in a single composition.

The compounds described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions provided herewith will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination provided herewith may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Patient Selection and Monitoring

The compounds described herein can modulate PKM2. Accordingly, a patient and/or subject can be selected for treatment using a compound described herein by first evaluating the patient and/or subject to determine whether the subject is in need of modulation of PKM2, and if the subject is determined to be in need of modulation of PKM2, then administering to the subject a compound described herein.

A subject can be evaluated as being in need of modulation of PKM2 using methods known in the art, e.g., by measuring the presence and/or activity of PKM2 in the patient. In some embodiments, the activity and/or level of PKM2 is evaluated in the cancer.

A patient receiving a compound described herein can be monitored, for example, for improvement in the condition and/or adverse effects. Improvement of a patient's condition can be evaluated, for example, by monitoring the growth, absence of growth, or regression of the cancer (e.g., a tumor). In some embodiments, the patient is evaluated using a radiological assay or evaluation of hemolytic parameters.

The compounds described herein can activate mutant PKRs. Accordingly, a patient and/or subject can be selected for treatment using a compound described herein by first evaluating the patient and/or subject to determine whether the subject carries a mutation in PKR (for examples, one of the mutations as described herein), and if the subject is determined to be carrying a mutation in PKR thus is in need of activation of the activity of the mutant PKR, then optionally administering to the subject a compound described herein. A subject can be evaluated as carrying a mutation in PKR using methods known in the art.

EXAMPLES

In the following examples, the reagents (chemicals) were purchased from commercial sources (such as Alfa, Acros, Sigma Aldrich, TCI and Shanghai Chemical Reagent Company), and used without further purification. Flash chromatography was performed on an Ez Purifier III using column with silica gel particles of 200-300 mesh. Analytical and preparative thin layer chromatography (TLC) plates were HSGF 254 (0.15-0.2 mm thickness, Shanghai Anbang Company, China). Nuclear magnetic resonance (NMR) spectra were obtained on a Brucker AMX-400 NMR (Brucker, Switzerland). Chemical shifts were reported in parts per million (ppm, δ) downfield from tetramethylsilane. Mass spectra were given with electrospray ionization (ESI) from a Waters LCT TOF Mass Spectrometer (Waters, USA). HPLC chromatographs were record on an Agilent 1200 Liquid Chromatography (Agilent, USA, column: Ultimate 4.6 mm×50 mm, 5 μm, mobile phase A: 0.1% formic acid in water; mobile phase B: acetonitrile). Microwave reactions were run on an Initiator 2.5 Microwave Synthesizer (Biotage, Sweden).

ABBREVIATIONS LIST

General
anhy. anhydrous
aq. aqueous
Min minute(s)
hr Hour (s)
mL milliliter
mmol millimole(s)
mol mole(s)
s.m. starting material
MS mass spectrometry
NMR nuclear magnetic resonance
r.t. (rt) room temperature
TLC thin layer chromatography HPLC high-performance liquid chromatography
Spectrum
Hz hertz
δ chemical shift
J coupling constant
s singlet
d doublet
t triplet
q quartet
m multiplet
br broad
qd quartet of doublets
dquin doublet of quintets
dd doublet of doublets
dt doublet of triplets
Solvents and Reagents
$CHCl_3$ chloroform
DCM dichloromethane
DMF dimethylformamide
$Et_2O$ diethyl ether
EtOH ethyl alcohol
EtOAc ethyl acetate
MeOH methyl alcohol
MeCN acetonitrile
PE petroleum ether
THF tetrahydrofuran
AcOH acetic acid
HCl hydrochloric acid
$H_2SO_4$ sulfuric acid
$NH_4Cl$ ammonium chloride
KOH potassium hydroxide
NaOH sodium hydroxide
$K_2CO_3$ potassium carbonate
$Na_2CO_3$ sodium carbonate
TFA trifluoroacetic acid
$Na_2SO_4$ sodium sulfate
$NaBH_4$ sodium borohydride
$NaHCO_3$ sodium bicarbonate
LiHMDS lithium hexamethyldisilylamide
NaHMDS sodium hexamethyldisilylamide
LAH lithium aluminum hydride
$NaBH_4$ sodium borohydride
LDA lithium diisopropylamide
$Et_3N$ triethylamine
Py pyridine
DMAP 4-(dimethylamino)pyridine
DIPEA N,N-diisopropylethylamine
$NH_4OH$ ammonium hydroxide
EDCI 1-ethyl-3-(3-dimethylaminopropyl)carbodiimide
HOBt 1-hydroxybenzotriazole
HBTU 2-(1H-Benzotriazole-1-yl)-1,1,3,3-tetramethyluronium hexafluorophosphate
HATU O-(7-azabenzotriazol-1-yl)-N,N,N',N'-tetramethyluronium
Xphos 2-Dicyclohexylphosphino-2',4',6'-triisopropylbiphenyl
BINAP 2,2'-bis(diphenylphosphanyl)-1,1'-binaphthyl Example 1

PKM2 Assay

Procedure:
PKM2 stock enzyme solution was diluted in Reaction Buffer
2 μL of compound was added into each well first, and then 180 μL of the Reaction Mix was added.
Reaction mixture with compound (without ADP) were incubated for 30 minutes at 4° C.
Plates were re-equilibrated to room temperature prior to adding 20 μL ADP to initiate the reaction.
Reaction progress was measured as changes in absorbance at 340 nm wavelength at room temperature (25° C.)
Reaction Mix: PKM2 (50 ng/well), ADP (0.7 mM), PEP (0.15 mM), NADH (180 μM), LDH (2 units) in Reaction Buffer
Reaction Buffer: 100 mM KCl, 50 mM Tris pH 7.5, 5 mM MgCl2, 1 mM DTT, 0.03% BSA.

Example 2

PKR Mutant Assay

Procedure
PKR or PKR mutant enzyme solution was diluted in assay buffer.
2 μL of test compound was added into wells first, and then 180 μL reaction mix was added.
Reactions mixture with test compound was assembled except for ADP, and plates were stored for 60 minutes at room temperature.
20 uL ADP was added to start reaction at room temperature and reaction progress was measured as changes in absorbance at 340 nm wavelength at room temperature.
Test Compound Preparation:
Test compound stock was made at 100x concentration in 100% DMSO (10 mM)
1 to 3 dilutions were made for 11 points (i.e. 50 μl of first concentration added to 100 μl 100% DMSO to yield 3.33 mM, 50 μl of this added to 100 μl DMSO to yield 1.11 mM, and so forth)
1 to 100 dilution into assay (2 μl in 200 μl) yielded starting concentration of 100 μM, decreasing 3 fold for 11 points
Assay Buffer: 100 mM KCl, 50 mM Tris 7.5, 5 mM $MgCl_2$, 1 mM DTT, 0.03% BSA
Reaction Mixture: PKR mutant enzyme: 80-400 ng/well; ADP: 0.22-1.65 mM; PEP: 0.1-0.5 mM; NADH:180 uM; LDH: 0.5 units (Sigma#59023); DTT: 1 mM; BSA: 0.03%.

Example 3

PKR WT Single Point Percent Activation Assay

A compound described herein was diluted with DMSO and tested at 1 μM concentration. The enzyme was diluted in 1× Buffer: (100 mM KCl, 50 mM Tris 7.5, 5 mM $MgCl_2$, 1 mM DTT, 0.03% BSA). 2 μL of compound solution was first added into wells, and then 180 μL of enzyme solution was added. Assays were assembled except for ADP, and plates were stored for 60 minutes at RT. 20 μL ADP was added to start the assay and assay output was evaluated using OD340 at SpectraMax. The assay was run at room temperature.
Final concentration: PKR wt (100 ng/well), Tris pH 7.5 (50 mM), KCl (100 mM), $MgCl_2$ (5 mM), ADP (0.48 mM), PEP (0.15 mM), NADH (180 μM), LDH (0.5 units, Sigma 59023), DTT (1 mM) and BSA (0.03%).

Example 4

PKR R510Q Single Point Percent Activation Assay

A compound described herein was diluted with DMSO and tested at 1 μM concentration. The enzyme was diluted in 1× Buffer: (100 mM KCl, 50 mM Tris 7.5, 5 mM MgCl$_2$, 1 mM DTT, 0.03% BSA). 2 μL of compound solution was first added into wells, and then 180 μL of enzyme solution was added. Assays were assembled except for ADP, and plates were stored for 60 minutes at RT. 20 μL ADP was added to start the assay and assay output was evaluated using OD340 at SpectraMax. The assay was run at room temperature.

Final concentration: PKR R510Q (40 ng/well), Tris pH 7.5 (50 mM), KCl (100 mM), MgCl$_2$ (5 mM), ADP (0.2 mM), PEP (0.11 mM), NADH (180 μM), LDH (0.5 units, Sigma 59023), DTT (1 mM) and BSA (0.03%).

Example 5

PKR R532W Single Point Percent Activation Assay

A compound described herein was diluted with DMSO and tested at 1 μM concentration. The enzyme was diluted in 1× Buffer: (100 mM KCl, 50 mM Tris 7.5, 5 mM MgCl$_2$, 1 mM DTT, 0.03% BSA). 2 μL of compound solution was first added into wells, and then 180 μL of enzyme solution was added. Assays were assembled except for ADP, and plates were stored for 60 minutes at RT. 20 μL ADP was added to start the assay and assay output was evaluated using OD340 at SpectraMax. The assay was run at room temperature.

Final concentration: PKR R532W (100 ng/well), Tris pH 7.5 (50 mM), KCl (100 mM), MgCl$_2$ (5 mM), ADP (0.36 mM), PEP (0.1 mM), NADH (180 μM), LDH (0.5 units, Sigma 59023), DTT (1 mM) and BSA (0.03%).

Example 6

Scheme 1: Preparation of Intermediate 1

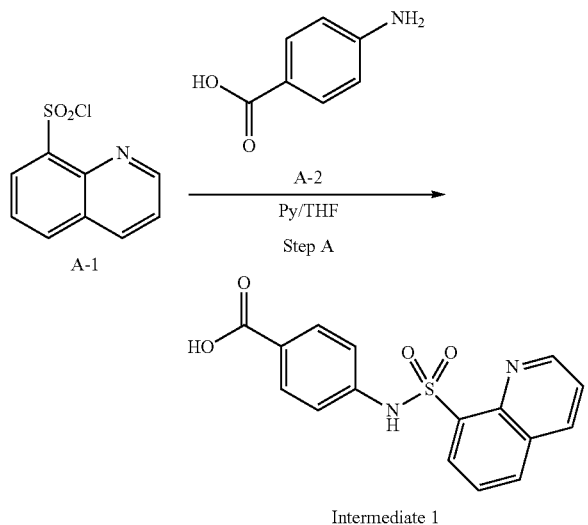

Step A: 4-(quinoline-8-sulfonamido)benzoic acid (1)

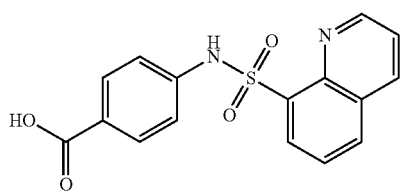

To a solution of 4-aminobenzoic acid (10 g, 73 mmol) in 100 mL of anhydrous THF was added pyridine (1.15 g, 146 mmol), quinoline-8-sulfonyl chloride (20 g, 88 mmol) at 0° C. The resulting mixture was stirred at 70° C. overnight. After filtration, the residue was washed with EtOH and 14 g of title compound was obtained as pure product.

$^1$H NMR (DMSO-d$_6$) δ: 10.71 (s, 1H), 9.12 (dd, J=4.2, 1.7 Hz, 1H), 8.47 (dd, J=7.5, 1.3 Hz, 1H), 8.51 (dd, J=8.3, 1.9 Hz, 1H), 8.29 (dd, J=8.2, 1.2 Hz, 1H), 7.62-7.79 (m, 4H), 7.14-7.22 (m, 2H). LC-MS: m/z 329.3 (M+H)$^+$.

Example 7

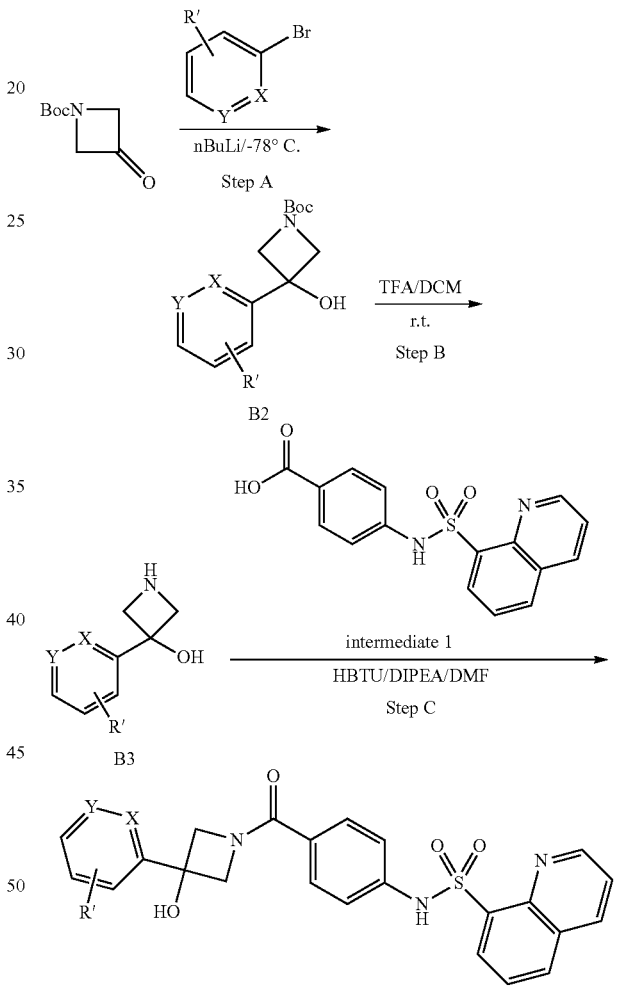

Scheme 2. General Procedure 1

Step A

To a solution of the corresponding Aryl Bromide (1.0 eq.) in super dried THF was added a solution of n-BuLi in THF (1.05 eq.) dropwise at −78° C. After the addition was complete, the mixture was stirred at −78° C. for about 0.5 hour. Then a solution of Boc-3-azetidine in THF was added dropwise via a syringe at −78° C. After the addition, the resulting mixture was stirred at −78° C. under N$_2$ for 2 h and then allowed to warm to r.t. The reaction mixture was then quenched by sat. NH₄Cl aq., and the residue mixture was extracted with EtOAc (50 mL, 30 mL). The combined organic phase was washed with brine, dried over anhydrous Na₂SO₄ and concentrated in vacuo. The residue was purified by column chromatography (PE/EtOAc) which afforded the desired compound B2.

Step B

To a solution of compound B2 (1 eq.) in DCM, was added TFA (10 eq.). The reaction mixture was stirred at room temperature for about 2 hours, when LCMS detected no s.m. The reaction mixture was concentrated to afford the desired product 3 as the TFA salt.

Step C

To a round-bottomed flask was added compound B3 (1 eq.), DMF (5 mL), DIPEA (3.0 eq.), HBTU (1.2 eq.), and intermediate 1 (1 eq.) sequentially. The reaction mixture was stirred at room temperature overnight or until TLC showed that the s.m. was consumed. The mixture was diluted with brine, extracted with ethyl acetate. The organic layer was dried with anhydrous Na₂SO₄, filtered, and the filtrate was concentrated. The desired product was purified by silica gel chromatography.

The following compounds were prepared via Example 7.

N-(4-(3-hydroxy-3-(2-methoxyphenyl)azetidine-1-carbonyl)phenyl)quinoline-8-sulfonamide (2)

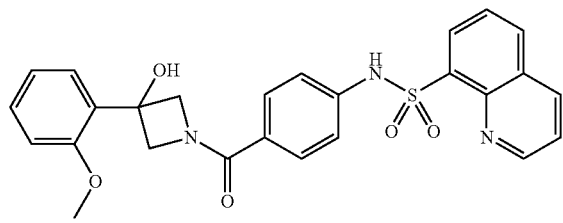 [SMILES: COc1ccccc1C1(O)CN(C(=O)c2ccc(NS(=O)(=O)c3cccc4cccnc34)cc2)C1]

¹H NMR (CHLOROFORM-d) δ: 9.21 (dd, J=4.4, 1.7 Hz, 1H), 8.87 (s, 1H), 8.42 (d, J=7.3 Hz, 1H), 8.38 (d, J=8.4 Hz, 1H), 8.08 (dd, J=8.2, 1.2 Hz, 1H), 7.69 (dd, J=8.4, 4.4 Hz, 1H), 7.67-7.62 (m, 1H), 7.46-7.40 (m, 2H), 7.37-7.30 (m, 1H), 7.25 (dd, J=7.6, 1.6 Hz, 1H), 7.16-7.09 (m, 2H), 6.99 (td, J=7.5, 0.9 Hz, 1H), 6.94 (d, J=8.2 Hz, 1H), 4.58 (s, 2H), 4.39 (s, 2H), 3.89 (s, 3H), 3.34 (s, 1H). LC-MS: m/z 490.5 (M+H)⁺

N-(4-(3-(2-fluorophenyl)-3-hydroxyazetidine-1-carbonyl)phenyl)quinoline-8-sulfonamide (3)

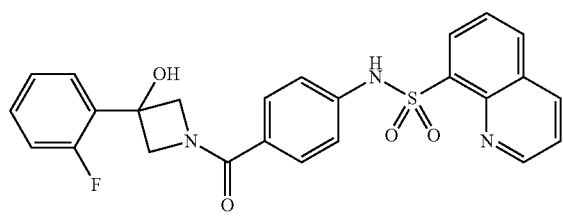 [SMILES: O=C(c1ccc(NS(=O)(=O)c2cccc3cccnc23)cc1)N1CC(O)(c2ccccc2F)C1]

¹H NMR (CHLOROFORM-d) δ: 9.17 (dd, J=4.3, 1.7 Hz, 1H), 8.58 (s, 1H), 8.39 (dd, J=7.3, 1.4 Hz, 1H), 8.32 (dd, J=8.4, 1.7 Hz, 1H), 8.06 (dd, J=8.2, 1.4 Hz, 1H), 7.65 (dd, J=7.5, 3.5 Hz, 1H), 7.63-7.59 (m, 1H), 7.47-7.41 (m, 2H), 7.39-7.33 (m, 2H), 7.21-7.16 (m, 1H), 7.15-7.07 (m, 3H), 4.66 (dd, J=20.6, 11.3 Hz, 2H), 4.42 (dd, J=38.7, 10.2 Hz, 2H), 2.60 (s, 1H). LC-MS: m/z 478.5 (M+H)⁺.

N-(4-(3-(3-fluorophenyl)-3-hydroxyazetidine-1-carbonyl)phenyl)quinoline-8-sulfonamide (4)

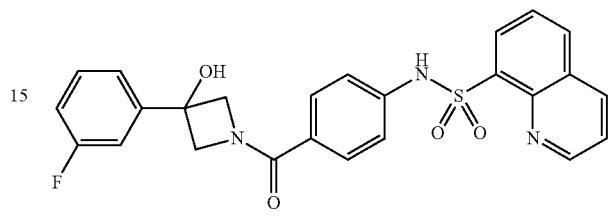

¹H NMR (CHLOROFORM-d) δ: 9.17 (dd, J=4.3, 1.7 Hz, 1H), 8.60 (s, 1H), 8.39 (dd, J=7.3, 1.4 Hz, 1H), 8.32 (dd, J=8.3, 1.7 Hz, 1H), 8.06 (d, J=6.9 Hz, 1H), 7.69-7.58 (m, 2H), 7.45 (d, J=8.6 Hz, 2H), 7.38 (td, J=8.0, 5.8 Hz, 1H), 7.27-7.23 (m, 1H), 7.22-7.17 (m, 1H), 7.11 (d, J=8.6 Hz, 2H), 7.07-7.01 (m, 1H), 4.45 (s, 4H), 2.53 (s, 1H). LC-MS: m/z 478.5 (M+H)⁺.

N-(4-(3-(2-chlorophenyl)-3-hydroxyazetidine-1-carbonyl)phenyl)quinoline-8-sulfonamide (5)

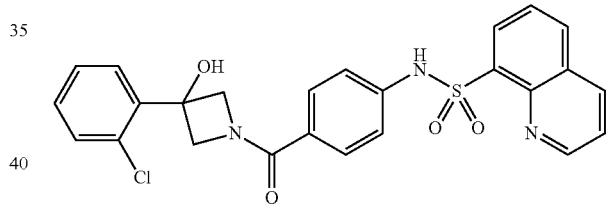

¹H NMR (CHLOROFORM-d) δ: 10.58 (s, 1H), 9.12 (dd, J=4.2, 1.8 Hz, 1H), 8.51 (dd, J=8.4, 1.7 Hz, 1H), 8.44 (dd, J=7.4, 1.4 Hz, 1H), 8.29 (dd, J=8.3, 1.2 Hz, 1H), 7.77-7.68 (m, 2H), 7.50-7.44 (m, 1H), 7.44-7.38 (m, 3H), 7.35-7.28 (m, 2H), 7.14 (d, J=8.7 Hz, 2H), 6.30 (s, 1H), 4.75 (d, J=9.4 Hz, 1H), 4.50 (d, J=11.1 Hz, 1H), 4.29 (d, J=9.2 Hz, 1H), 4.13 (d, J=11.0 Hz, 1H). LC-MS: m/z 494.6 (M+H)⁺.

N-(4-(3-hydroxy-3-(2-(trifluoromethyl)phenyl)azetidine-1-carbonyl)phenyl)quinoline-8-sulfonamide (6)

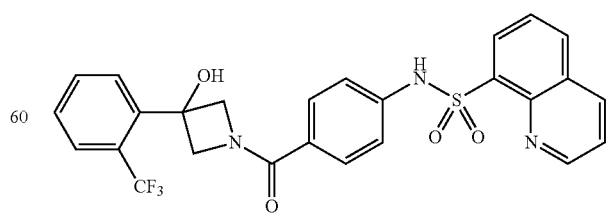

¹H NMR (CHLOROFORM-d) δ: 9.17 (dd, J=4.3, 1.6 Hz, 1H), 8.39 (dd, J=7.3, 1.5 Hz, 1H), 8.31 (dd, J=8.2, 1.8 Hz, 1H), 8.06 (dd, J=8.4, 1.3 Hz, 1H), 7.73 (d, J=7.6 Hz, 1H), 7.56-7.67 (m, 3H), 7.50 (s, 1H), 7.36-7.45 (m, 3H), 7.08-7.13 (m, 2H), 4.71 (br. s., 2H), 4.46 (br. s., 2H). LC-MS: m/z 528.5 (M+H)⁺.

N-(4-(3-hydroxy-3-(2-(trifluoromethoxy)phenyl)azetidine-1-carbonyl)phenyl)quinoline-8-sulfonamide (7)

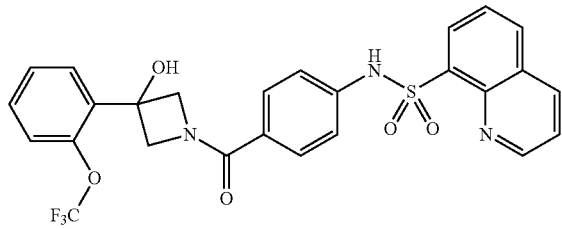 [SMILES: O=C(c1ccc(NS(=O)(=O)c2cccc3cccnc23)cc1)N1CC(O)(c2ccccc2OC(F)(F)F)C1]

¹H NMR (DMSO-d₆) δ: 10.59 (s, 1H), 9.13 (dd, J=4.3, 1.6 Hz, 1H), 8.52 (dd, J=8.4, 1.6 Hz, 1H), 8.45 (dd, J=7.3, 1.2 Hz, 1H), 8.29 (dd, J=8.2, 1.2 Hz, 1H), 7.69-7.78 (m, 2H), 7.53 (dd, J=7.9, 1.8 Hz, 1H), 7.39-7.48 (m, 3H), 7.29-7.37 (m, 2H), 7.12-7.19 (m, 2H), 6.40 (s, 1H), 4.66 (d, J=9.1 Hz, 1H), 4.39 (d, J=10.9 Hz, 1H), 4.25 (d, J=9.7 Hz, 1H), 4.11 (d, J=10.6 Hz, 1H). LC-MS: m/z 544.5 (M+H)⁺.

N-(4-(3-hydroxy-3-(2-methoxyphenyl)azetidine-1-carbonyl)phenyl)quinoline-8-sulfonamide (8)

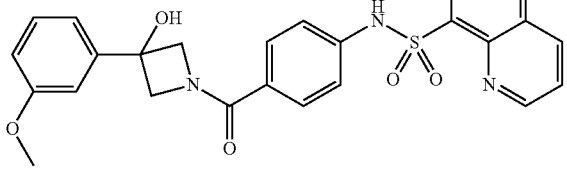

¹H NMR (CHLOROFORM-d) δ: 9.12 (d, J=2.8 Hz, 1H), 8.33 (d, J=7.3 Hz, 1H), 8.26 (d, J=7.8 Hz, 1H), 8.00 (d, J=8.0 Hz, 1H), 7.49-7.63 (m, 2H), 7.26-7.37 (m, 2H), 7.20 (t, J=7.9 Hz, 1H), 7.03 (d, J=8.3 Hz, 2H), 6.90-6.99 (m, 2H), 6.77 (d, J=6.8 Hz, 1H), 4.54-4.79 (m, 1H), 4.35 (br. s., 3H), 4.23-4.31 (m, 1H), 3.73 (s, 3H). LC-MS: m/z 490.5 (M+H)⁺.

N-(4-(3-hydroxy-3-(3-(trifluoromethyl)phenyl)azetidine-1-carbonyl)phenyl)quinoline-8-sulfonamide (9)

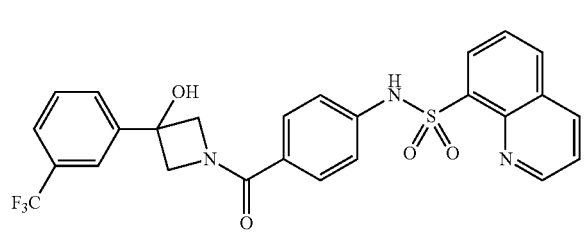 [SMILES: O=C(c1ccc(NS(=O)(=O)c2cccc3cccnc23)cc1)N1CC(O)(c2cccc(C(F)(F)F)c2)C1]

¹H NMR (DMSO-d₆) δ: 10.59 (br. s., 1H), 9.13 (dd, J=4.1, 1.8 Hz, 1H), 8.52 (dd, J=8.5, 1.8 Hz, 1H), 8.45 (dd, J=7.3, 1.5 Hz, 1H), 8.30 (dd, J=8.2, 1.2 Hz, 1H), 7.79-7.84 (m, 2H), 7.69-7.78 (m, 2H), 7.59-7.69 (m, 2H), 7.46-7.52 (m, J=8.8 Hz, 2H), 7.12-7.19 (m, J=8.8 Hz, 2H), 6.61 (s, 1H), 4.56 (d, J=8.5 Hz, 1H), 4.29 (d, J=8.5 Hz, 1H), 4.18 (br. s., 2H). LC-MS: m/z 544.5 (M+H)⁺.

N-(4-(3-hydroxy-3-(3-(trifluoromethoxy)phenyl)azetidine-1-carbonyl)phenyl)quinoline-8-sulfonamide (10)

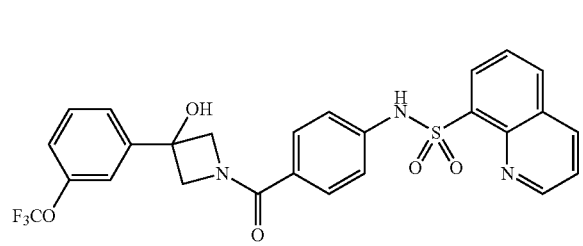 [SMILES: O=C(c1ccc(NS(=O)(=O)c2cccc3cccnc23)cc1)N1CC(O)(c2cccc(OC(F)(F)F)c2)C1]

¹H NMR (CHLOROFORM-d) δ: 9.15 (dd, J=4.4, 1.5 Hz, 1H), 8.36 (dd, J=7.3, 1.2 Hz, 1H), 8.29 (dd, J=8.4, 1.3 Hz, 1H), 8.03 (dd, J=8.2, 1.2 Hz, 1H), 7.54-7.66 (m, 2H), 7.31-7.40 (m, 5H), 7.12 (d, J=7.0 Hz, 1H), 7.06 (d, J=8.5 Hz, 2H), 4.36 (br. s., 4H). LC-MS: m/z 544.6 (M+H)⁺.

N-(4-(3-(3-chlorophenyl)-3-hydroxyazetidine-1-carbonyl)phenyl)quinoline-8-sulfonamide (11)

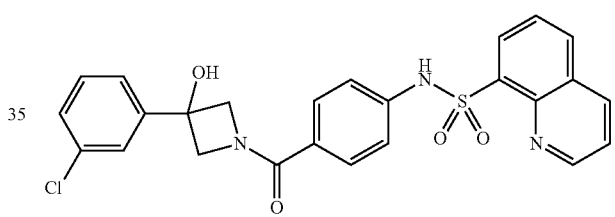

¹H NMR (DMSO-d₆) δ: 10.61 (s, 1H), 9.13 (dd, J=4.4, 1.8 Hz, 1H), 8.52 (dd, J=8.4, 1.6 Hz, 1H), 8.45 (dd, J=7.5, 1.3 Hz, 1H), 8.29 (dd, J=8.2, 1.2 Hz, 1H), 7.69-7.78 (m, 2H), 7.43-7.54 (m, 4H), 7.40 (t, J=7.8 Hz, 1H), 7.32-7.37 (m, 1H), 7.15 (d, J=8.8 Hz, 2H), 6.50 (s, 1H), 4.51 (d, J=8.5 Hz, 1H), 4.25 (d, J=8.5 Hz, 1H), 4.09-4.17 (m, 2H). LC-MS: m/z 494.5 (M+H)⁺.

N-(4-(3-(4-fluoro-2-methylphenyl)-3-hydroxyazetidine-1-carbonyl)phenyl)quinoline-8-sulfonamide (12)

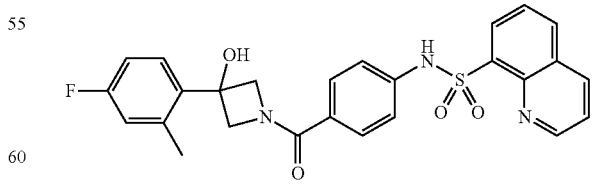

¹H NMR (DMSO-d₆) δ: 10.60 (br. s., 1H), 9.13 (dd, J=4.3, 1.6 Hz, 1H), 8.51 (dd, J=8.5, 1.8 Hz, 1H), 8.45 (dd, J=7.3, 1.5 Hz, 1H), 8.29 (dd, J=8.2, 1.5 Hz, 1H), 7.67-7.78 (m, 2H), 7.41-7.47 (m, J=8.5 Hz, 2H), 7.30 (dd, J=8.5, 6.2 Hz, 1H), 7.11-7.18 (m, J=8.8 Hz, 2H), 7.03 (dd, J=10.0, 2.6

Hz, 1H), 6.90-7.00 (m, 1H), 6.14 (s, 1H), 4.73 (d, J=9.1 Hz, 1H), 4.45 (d, J=10.6 Hz, 1H), 4.27 (d, J=9.4 Hz, 1H), 4.09-4.16 (m, 1H), 2.22-2.30 (m, 3H), LC-MS: m/z 492.6 (M+H)⁺.

N-(4-(3-(2-ethylphenyl)-3-hydroxyazetidine-1-carbonyl)phenyl)quinoline-8-sulfonamide (13)

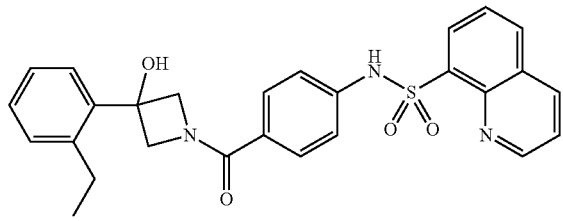 [SMILES: CCc1ccccc1C1(O)CN(C(=O)c2ccc(NS(=O)(=O)c3cccc4cccnc34)cc2)C1]

¹H NMR (DMSO-d6) δ: 10.59 (br. s., 1H), 9.13 (dd, J=4.1, 1.8 Hz, 1H), 8.52 (d, J=7.3 Hz, 1H), 8.45 (d, J=6.5 Hz, 1H), 8.29 (d, J=7.9 Hz, 1H), 7.68-7.78 (m, 2H), 7.44 (d, J=8.5 Hz, 2H), 7.22-7.29 (m, 3H), 7.15 (d, J=8.8 Hz, 3H), 6.15 (s, 1H), 4.72 (d, J=9.1 Hz, 1H), 4.45 (d, J=10.3 Hz, 1H), 4.30 (d, J=9.4 Hz, 1H), 4.15 (d, J=10.0 Hz, 1H), 2.52-2.57 (m, 3H), 1.16 (t, J=7.5 Hz, 3H). LC-MS: m/z 488.5 (M+H)⁺.

N-(4-(3-(4-fluorophenyl)-3-hydroxyazetidine-1-carbonyl)phenyl)quinoline-8-sulfonamide (14)

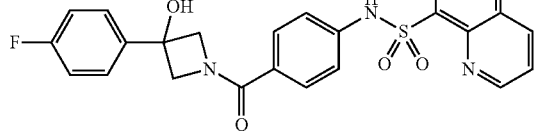

¹H NMR (DMSO-d₆) δ: 10.60 (s, 1H), 9.13 (dd, J=4.1, 1.8 Hz, 1H), 8.51 (dd, J=8.5, 1.8 Hz, 1H), 8.45 (dd, J=7.3, 1.2 Hz, 1H), 8.29 (dd, J=8.2, 1.2 Hz, 1H), 7.68-7.78 (m, 2H), 7.42-7.55 (m, 4H), 7.13-7.20 (m, 4H), 6.41 (s, 1H), 4.47 (d, J=8.8 Hz, 1H), 4.27 (d, J=8.5 Hz, 1H), 4.15 (br. s., 2H). LC-MS: m/z 478.6 (M+H)⁺.

N-(4-(3-hydroxy-3-(o-tolyl)azetidine-1-carbonyl)phenyl)quinoline-8-sulfonamide (15)

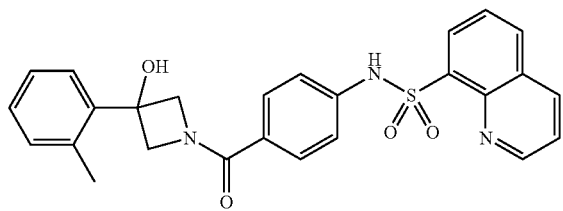 [SMILES: Cc1ccccc1C1(O)CN(C(=O)c2ccc(NS(=O)(=O)c3cccc4cccnc34)cc2)C1]

¹H NMR (CHLOROFORM-d) δ: 9.16 (s, 1H), 8.5-8.6 (m, 1H), 8.2-8.4 (m, 2H), 8.05-8.1 (m, 1H), 7.6 (m, 2H), 7.4 (m, 2H), 7.0-7.2 (m, 6H), 4.7 (m, 2H), 4.4 (m, 2H), 4.38-4.48 (m, 2H), 2.3 (s, 3H). LC-MS: m/z 474.5 (M+H)⁺.

N-(4-(3-butyl-3-hydroxyazetidine-1-carbonyl)phenyl)quinoline-8-sulfonamide (16)

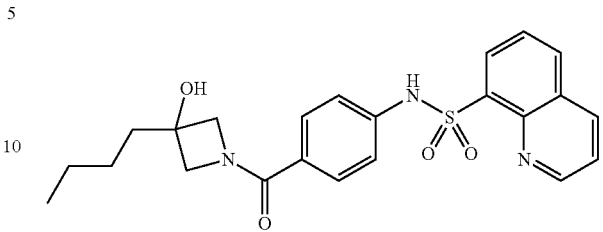

¹H NMR (DMSO-d6) δ: 10.56 (s, 1H), 9.13 (dd, J=4.3, 1.6 Hz, 1H), 8.52 (dd, J=8.5, 1.5 Hz, 1H), 8.44 (d, J=7.3 Hz, 1H), 8.29 (d, J=7.9 Hz, 1H), 7.69-7.78 (m, 2H), 7.37-7.42 (m, J=8.5 Hz, 2H), 7.11-7.15 (m, J=8.5 Hz, 2H), 5.51 (s, 1H), 4.03 (d, J=8.8 Hz, 1H), 3.92 (d, J=8.8 Hz, 1H), 3.79-3.85 (m, 1H), 3.73 (br. s., 1H), 1.54 (d, J=7.3 Hz, 2H), 1.22-1.28 (m, 4H), 0.82-0.87 (m, 3H). LC-MS: m/z 440.6 (M+H)⁺.

N-(4-(3-hydroxy-3-(2-(trifluoromethyl)pyridin-3-yl)azetidine-1-carbonyl)phenyl)quinoline-8-sulfonamide (17)

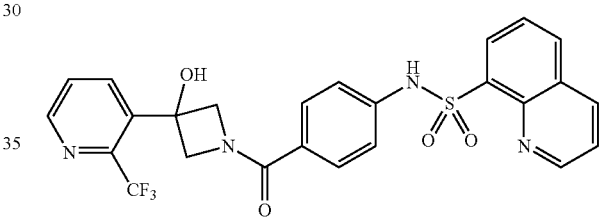

¹H NMR (DMSO-d₆) δ: 10.61 (br. s., 1H), 9.13 (dd, J=4.3, 1.6 Hz, 1H), 8.68 (d, J=4.1 Hz, 1H), 8.52 (dd, J=8.4, 1.6 Hz, 1H), 8.46 (dd, J=7.3, 1.5 Hz, 1H), 8.30 (dd, J=8.2, 1.2 Hz, 1H), 8.09 (d, J=7.9 Hz, 1H), 7.65-7.79 (m, 3H), 7.41-7.47 (m, J=8.8 Hz, 2H), 7.13-7.19 (m, J=8.8 Hz, 2H), 6.59 (s, 1H), 4.79 (d, J=8.8 Hz, 1H), 4.53 (d, J=10.9 Hz, 1H), 4.28 (d, J=8.2 Hz, 1H), 4.11-4.19 (m, 1H). LC-MS: m/z 529.6 (M+H)±.

N-(4-(3-(2-fluoropyridin-3-yl)-3-hydroxyazetidine-1-carbonyl)phenyl)quinoline-8-sulfonamide (18)

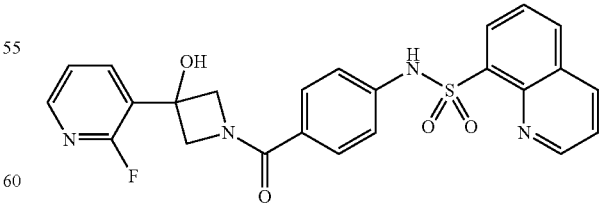

¹H NMR (DMSO-d₆) δ: 10.61 (br. s., 1H), 9.13 (dd, J=4.4, 1.8 Hz, 1H), 8.43-8.53 (m, 2H), 8.27 (d, J=8.2 Hz, 1H), 8.16 (d, J=4.7 Hz, 1H), 8.02 (ddd, J=10.1, 7.8, 1.8 Hz, 1H), 7.67-7.78 (m, 2H), 7.43-7.50 (m, J=8.2 Hz, 2H), 7.30-7.38 (m, 1H), 7.14-7.23 (m, J=7.9 Hz, 2H), 6.64 (s, 1H), 4.66 (d, J=9.1 Hz, 1H), 4.42 (d, J=10.6 Hz, 1H), 4.31 (d, J=9.4 Hz, 1H), 4.14 (d, J=5.0 Hz, 1H). LC-MS: m/z 479.5 (M+H)⁺.

N-(4-(3-hydroxy-3-(2-methylpyridin-3-yl)azetidine-1-carbonyl)phenyl)quinoline-8-sulfonamide (19)

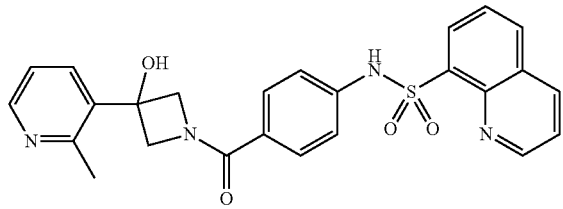 [SMILES: Cc1ncccc1C1(O)CN(C(=O)c2ccc(NS(=O)(=O)c3cccc4cccnc34)cc2)C1]

¹H NMR (DMSO-d₆) δ: 10.62 (s, 1H), 9.13 (dd, J=4.4, 1.8 Hz, 1H), 8.52 (dd, J=8.5, 1.8 Hz, 1H), 8.44-8.50 (m, 2H), 8.30 (dd, J=8.4, 1.3 Hz, 1H), 7.96 (br. s., 1H), 7.69-7.79 (m, 2H), 7.37-7.49 (m, 3H), 7.15 (d, J=8.8 Hz, 2H), 6.47 (br. s., 1H), 4.80 (d, J=8.8 Hz, 1H), 4.53 (d, J=10.6 Hz, 1H), 4.33 (d, J=9.1 Hz, 1H), 4.16 (d, J=9.7 Hz, 1H). LC-MS: m/z 528.5 (M+H)⁺.

N-(4-(3-hydroxy-3-(2-methoxypyridin-3-yl)azetidine-1-carbonyl)phenyl)quinoline-8-sulfonamide (20)

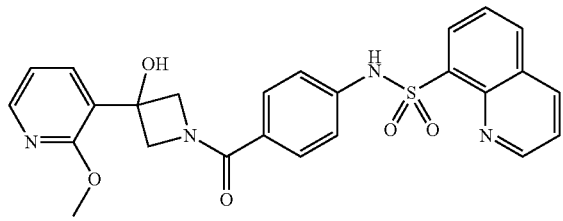 [SMILES: COc1ncccc1C1(O)CN(C(=O)c2ccc(NS(=O)(=O)c3cccc4cccnc34)cc2)C1]

¹H NMR (CHLOROFORM-d) δ: 9.17 (dd, J=4.3, 1.7 Hz, 1H), 8.58 (s, 1H), 8.39 (dd, J=7.3, 1.3 Hz, 1H), 8.32 (dd, J=8.4, 1.7 Hz, 1H), 8.15 (dd, J=5.0, 1.8 Hz, 1H), 8.06 (dd, J=8.2, 1.4 Hz, 1H), 7.67-7.63 (m, 1H), 7.63-7.61 (m, 1H), 7.56 (dd, J=7.4, 1.9 Hz, 1H), 7.43 (d, J=8.7 Hz, 2H), 7.10 (d, J=8.7 Hz, 2H), 6.94 (dd, J=7.4, 5.0 Hz, 1H), 4.62 (d, J=10.3 Hz, 1H), 4.46 (dd, J=18.3, 11.4 Hz, 2H), 4.31 (d, J=10.9 Hz, 1H), 4.01 (s, 3H), 3.37 (s, 1H). LC-MS: m/z 491.5 (M+H)⁺.

N-(4-(3-hydroxy-3-(3-methoxypyridin-2-yl)azetidine-1-carbonyl)phenyl)quinoline-8-sulfonamide (21)

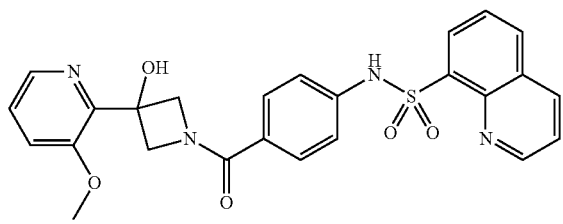 [SMILES: COc1cccnc1C1(O)CN(C(=O)c2ccc(NS(=O)(=O)c3cccc4cccnc34)cc2)C1]

¹H NMR (CHLOROFORM-d) δ: 9.17 (dd, J=4.3, 1.6 Hz, 1H), 8.57 (s, 1H), 8.39 (dd, J=7.3, 1.2 Hz, 1H), 8.32 (dd, J=8.4, 1.6 Hz, 1H), 8.14 (dd, J=4.6, 0.7 Hz, 1H), 8.06 (dd, J=8.2, 1.2 Hz, 1H), 7.65 (dd, J=7.2, 3.1 Hz, 1H), 7.63-7.58 (m, 1H), 7.48 (d, J=8.6 Hz, 2H), 7.33-7.29 (m, 1H), 7.26 (d, J=8.3 Hz, 1H), 7.11 (d, J=8.6 Hz, 2H), 6.28 (s, 1H), 4.71 (d, J=10.5 Hz, 1H), 4.62 (d, J=9.0 Hz, 1H), 4.43 (d, J=9.3 Hz, 1H), 4.26 (d, J=10.5 Hz, 1H), 3.83 (s, 3H). LC-MS: m/z 491.4 (M+H)⁺.

N-(4-(3-(3-fluoropyridin-2-yl)-3-hydroxyazetidine-1-carbonyl)phenyl)quinoline-8-sulfonamide (22)

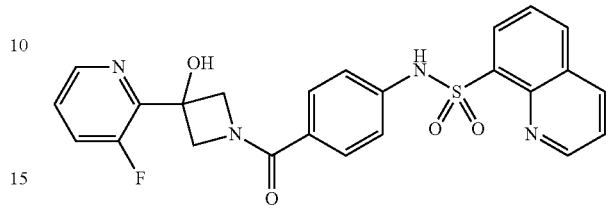

¹H NMR (CHLOROFORM-d) δ: 9.18 (dd, J=4.3, 1.7 Hz, 1H), 8.63 (s, 1H), 8.49 (d, J=2.5 Hz, 1H), 8.47 (d, J=4.3 Hz, 1H), 8.39 (dd, J=7.3, 1.3 Hz, 1H), 8.32 (dd, J=8.4, 1.7 Hz, 1H), 8.07 (dd, J=8.2, 1.3 Hz, 1H), 7.65 (dd, J=7.7, 3.6 Hz, 1H), 7.64-7.59 (m, 1H), 7.46-7.42 (m, 2H), 7.42-7.39 (m, 1H), 7.12 (d, J=8.7 Hz, 2H), 4.64 (d, J=10.3 Hz, 2H), 4.40 (d, J=30.4 Hz, 2H), 2.98 (s, 1H). LC-MS: m/z 479.1 (M+H)⁺.

N-(4-(3-(3-chloropyridin-2-yl)-3-hydroxyazetidine-1-carbonyl)phenyl)quinoline-8-sulfonamide (23)

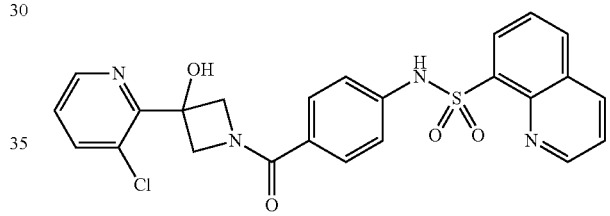

¹H NMR (CHLOROFORM-d) δ: 9.24 (dd, J=4.4, 1.7 Hz, 1H), 9.01 (s, 1H), 8.48 (dd, J=4.7, 1.4 Hz, 1H), 8.45 (dd, J=7.3, 1.3 Hz, 1H), 8.41 (dd, J=8.4, 1.6 Hz, 1H), 8.10 (dd, J=8.1, 1.2 Hz, 1H), 7.81 (dd, J=8.0, 1.4 Hz, 1H), 7.71 (dd, J=8.3, 4.3 Hz, 1H), 7.69-7.63 (m, 1H), 7.47 (d, J=8.7 Hz, 2H), 7.33 (dd, J=8.0, 4.7 Hz, 1H), 7.16 (d, J=8.6 Hz, 2H), 4.89 (d, J=10.5 Hz, 2H), 4.50-4.29 (m, 2H). LC-MS: m/z 495.5 (M+H)⁺.

N-(4-(3-hydroxy-3-(3-(trifluoromethyl)pyridin-2-yl)azetidine-1-carbonyl)phenyl)quinoline-8-sulfonamide (24)

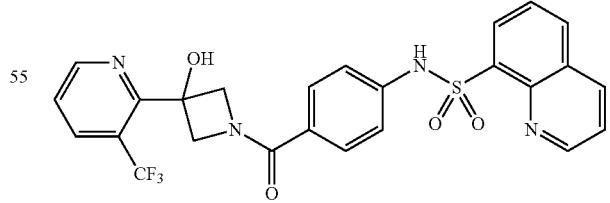

¹H NMR (CHLOROFORM-d) δ: 9.18 (dd, J=4.3, 1.7 Hz, 1H), 8.73 (d, J=3.7 Hz, 1H), 8.58 (s, 1H), 8.39 (dd, J=7.3, 1.3 Hz, 1H), 8.32 (dd, J=8.4, 1.7 Hz, 1H), 8.13-8.01 (m, 2H), 7.68-7.59 (m, 2H), 7.50-7.34 (m, 3H), 7.15-7.06 (m, 2H), 5.06 (d, J=9.2 Hz, 1H), 4.85 (d, J=11.2 Hz, 1H), 4.35 (dd, J=15.0, 3.1 Hz, 2H), 3.14 (s, 1H). LC-MS: m/z 529.6 (M+H)⁺.

47

N-(4-(3-(3-(difluoromethoxy)pyridin-2-yl)-3-hydroxyazetidine-1-carbonyl)phenyl)quinoline-8-sulfonamide (25)

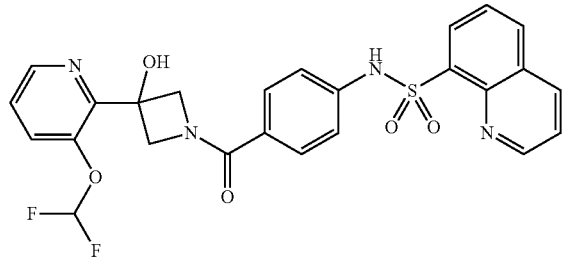 [SMILES: O=C(c1ccc(NS(=O)(=O)c2cccc3cccnc23)cc1)N1CC(O)(c2ncccc2OC(F)F)C1]

$^1$H NMR (CHLOROFORM-d) δ: 9.17 (dd, J=4.3, 1.7 Hz, 1H), 8.58 (s, 1H), 8.43-8.35 (m, 2H), 8.31 (dd, J=8.4, 1.7 Hz, 1H), 8.06 (dd, J=8.2, 1.3 Hz, 1H), 7.63 (dt, J=15.4, 6.2 Hz, 3H), 7.44 (d, J=8.7 Hz, 2H), 7.37 (dd, J=8.3, 4.7 Hz, 1H), 7.10 (d, J=8.7 Hz, 2H), 6.59 (t, J=71.8 Hz, 1H), 6.02 (s, 1H), 4.65 (dd, J=22.1, 10.2 Hz, 2H), 4.47 (d, J=9.4 Hz, 1H), 4.34 (d, J=10.8 Hz, 1H). LC-MS: m/z 527.6 (M+H)$^+$.

The following compounds were prepared via step A of Example 7.

tert-butyl 3-hydroxy-3-(2-methoxyphenyl)azetidine-1-carboxylate (26)

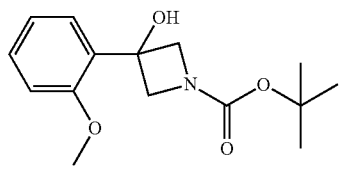 [SMILES: COc1ccccc1C1(O)CN(C(=O)OC(C)(C)C)C1]

$^1$H NMR (CHLOROFORM-d) δ: 7.37-7.29 (m, 2H), 7.02 (td, J=7.5, 1.0 Hz, 1H), 6.96 (d, J=8.2 Hz, 1H), 4.16 (dd, J=9.5, 1.0 Hz, 2H), 3.92 (s, 3H), 3.52 (d, J=5.5 Hz, 1H), 3.37 (s, 1H), 1.47 (s, 9H). LC-MS: m/z 280.3 (M+H)$^+$.

tert-butyl 3-(2-fluorophenyl)-3-hydroxyazetidine-1-carboxylate (27)

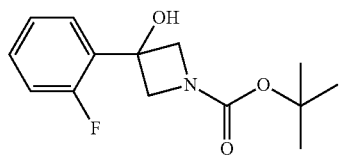

$^1$H NMR (CHLOROFORM-d) δ: 7.40 (td, J=7.7, 1.7 Hz, 1H), 7.35 (ddd, J=7.2, 4.7, 2.0 Hz, 1H), 7.19 (td, J=7.6, 1.1 Hz, 1H), 7.13 (ddd, J=11.1, 8.2, 1.0 Hz, 1H), 4.46 (d, J=9.5 Hz, 2H), 4.19 (d, J=9.6 Hz, 2H), 3.83 (dd, J=21.5, 9.3 Hz, 1H), 2.77 (d, J=1.3 Hz, 1H), 1.64 (s, 1H), 1.46 (d, J=5.4 Hz, 9H). LC-MS: m/z 168.3 (M+H)$^+$

48 tert-butyl 3-hydroxy-3-(3-methoxypyridin-2-yl)azetidine-1-carboxylate (28)

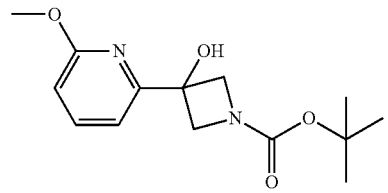 [SMILES: COc1cccc(C2(O)CN(C(=O)OC(C)(C)C)C2)n1]

$^1$H NMR (CHLOROFORM-d) δ: 8.16 (dd, J=3.4, 2.6 Hz, 1H), 7.33-7.30 (m, 2H), 4.52 (d, J=6.6 Hz, 2H), 4.12 (d, J=8.7 Hz, 2H), 3.95 (s, 3H), 1.51 (s, 9H). LC-MS: m/z 281.4 (M+H)$^+$.

tert-butyl 3-(3-fluorophenyl)-3-hydroxyazetidine-1-carboxylate (29)

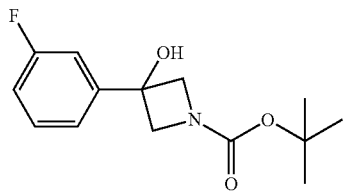 [SMILES: CC(C)(C)OC(=O)N1CC(O)(c2cccc(F)c2)C1]

$^1$H NMR (CHLOROFORM-d) δ: 7.38 (td, J=7.9, 5.8 Hz, 1H), 7.33-7.29 (m, 1H), 7.28-7.22 (m, 1H), 7.02 (tdd, J=8.4, 2.5, 1.0 Hz, 1H), 4.25-4.15 (m, 4H), 3.48 (s, 1H), 1.47 (s, 9H). LC-MS: m/z 268.3 (M+H)$^+$.

tert-butyl 3-(2-chlorophenyl)-3-hydroxyazetidine-1-carboxylate (30)

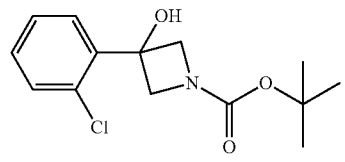 [SMILES: CC(C)(C)OC(=O)N1CC(O)(c2ccccc2Cl)C1]

$^1$H NMR (CHLOROFORM-d) δ: 7.45-7.42 (m, 1H), 7.40-7.36 (m, 1H), 7.32 (ddd, J=5.0, 2.8, 1.4 Hz, 2H), 4.52 (d, J=9.7 Hz, 2H), 4.24 (d, J=9.8 Hz, 2H), 3.07 (s, 1H), 1.47 (s, 9H). LC-MS: m/z 284.5 (M+H)$^+$.

Example 8

Scheme 3. General Procedure 2

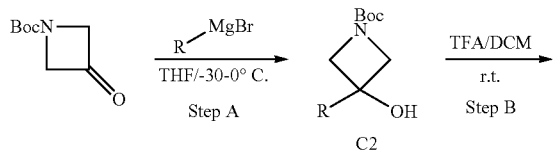

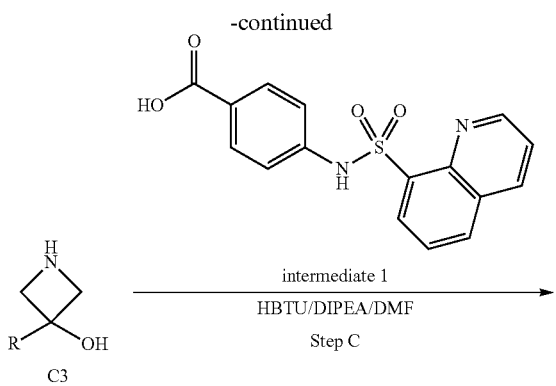

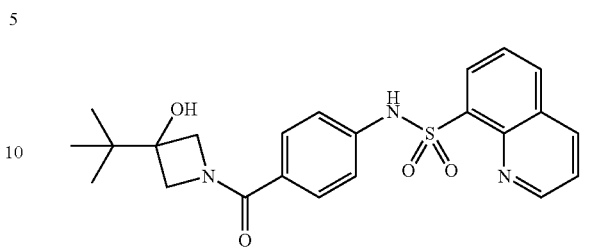

N-(4-(3-(tert-butyl)-3-hydroxyazetidine-1-carbonyl)phenyl)quinoline-8-sulfonamide (31)

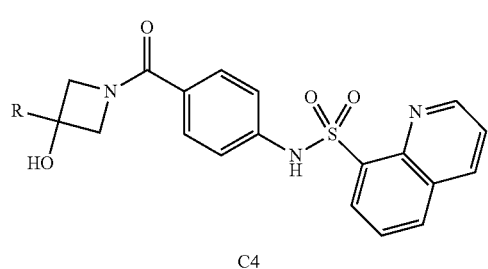

¹H NMR (CHLOROFORM-d) δ: 9.17 (dd, J=4.3, 1.7 Hz, 1H), 8.58 (s, 1H), 8.39 (dd, J=7.3, 1.4 Hz, 1H), 8.32 (dd, J=8.4, 1.7 Hz, 1H), 8.06 (dd, J=8.3, 1.3 Hz, 1H), 7.68-7.57 (m, 2H), 7.46-7.36 (m, 2H), 7.14-7.05 (m, 2H), 4.25 (dd, J=20.5, 10.0 Hz, 2H), 3.95 (d, J=9.0 Hz, 1H), 3.85-3.75 (m, 1H), 0.95 (s, 9H). LC-MS: m/z 466.6 (M+H)⁺.

N-(4-(3-hydroxy-3-isopropylazetidine-1-carbonyl)phenyl)quinoline-8-sulfonamide (32)

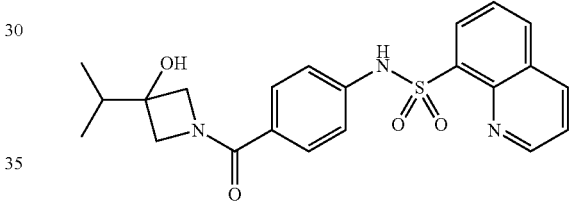

Step A

To a solution of Boc-3-azetidine 1 (1 eq.) in THF was added dropwise the corresponding RMgBr solution in THF (4 eq.) via a syringe at −30° C. After the addition, the resulting mixture was stirred at −30° C. under N₂ for 2 h, then allowed to warm to r.t. The reaction mixture was quenched by sat. NH₄Cl aq., and the resulting mixture was extracted with EtOAc (50 mL, 30 mL). The combined organic phase was washed with brine, dried over anhydrous Na₂SO₄ and concentrated in vacuo. The residue was purified by column chromatography (PE/EtOAc) to afford compound C2.

¹H NMR (CHLOROFORM-d) δ: 9.25 (s, 1H), 9.13 (s, 1H), 8.50-8.39 (m, 2H), 8.11 (d, J=7.8 Hz, 1H), 7.69 (dd, J=18.7, 10.9 Hz, 2H), 7.42 (d, J=8.4 Hz, 2H), 7.15 (d, J=8.5 Hz, 2H), 4.11 (d, J=9.9 Hz, 2H), 3.98 (d, J=8.9 Hz, 2H), 3.79-3.75 (m, 1H), 1.96-1.90 (m, 1H), 0.93 (d, J=6.8 Hz, 6H). LC-MS: m/z 426.5 (M+H)⁺.

Step B

To a solution of compound C2 (1 eq.) in DCM, was added TFA (10 eq.), the reaction mixture was held stirred at room temperature for about 2 hours, when LCMS detected no s.m. The reaction mixture was concentrated to afford the desired product C3 as the TFA salt. The crude product was used for the next step directly without further purification.

N-(4-(3-cyclopropyl-3-hydroxyazetidine-1-carbonyl)phenyl)quinoline-8-sulfonamide (33)

Step C

To a round-bottomed flask was added compound C3 (1 eq.), DMF (5 mL), DIPEA (3.0 eq.), HBTU (1.2 eq.), and intermediate 1 (1 eq.) sequentially. The reaction mixture was stirred at room temperature overnight or until TLC showed that the s.m. was consumed. The mixture was diluted with brine, extracted with ethyl acetate, the organic layer was dried with anhydrous Na₂SO₄, filtered, and the filtrate was concentrated. The desired product was purified by silica gel chromatography.

The following compounds were prepared via Example 8.

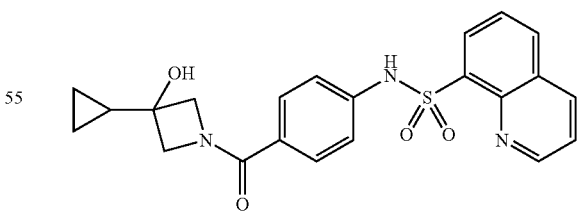

¹H NMR (CHLOROFORM-d) δ: 9.23-9.17 (m, 1H), 8.76 (s, 1H), 8.41 (dd, J=7.3, 1.3 Hz, 1H), 8.35 (d, J=7.0 Hz, 1H), 8.08 (dd, J=8.2, 1.3 Hz, 1H), 7.70-7.60 (m, 2H), 7.40 (d, J=8.6 Hz, 2H), 7.11 (d, J=8.6 Hz, 2H), 3.97 (d, J=8.4 Hz, 4H), 1.21 (ddd, J=10.4, 6.7, 4.2 Hz, 1H), 0.58 (d, J=8.1 Hz, 2H), 0.36 (d, J=5.2 Hz, 2H). LC-MS: m/z 424.5 (M+H)⁺.

N-(4-(3-ethyl-3-hydroxyazetidine-1-carbonyl)phenyl)quinoline-8-sulfonamide (34)

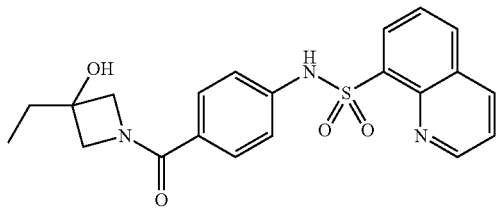 [SMILES: CCC1(O)CN(C(=O)c2ccc(NS(=O)(=O)c3cccc4cccnc34)cc2)C1]

¹H NMR (CHLOROFORM-d) δ: 9.17 (dd, J=4.2, 1.6 Hz, 1H), 8.59 (s, 1H), 8.38 (dd, J=7.3, 1.2 Hz, 1H), 8.31 (dd, J=8.4, 1.5 Hz, 1H), 8.06 (d, J=7.2 Hz, 1H), 7.69-7.55 (m, 2H), 7.40 (d, J=8.6 Hz, 2H), 7.09 (d, J=8.6 Hz, 2H), 4.07 (s, 3H), 3.98 (s, 1H), 2.15 (s, 1H), 1.76 (q, J=7.4 Hz, 2H), 0.95 (t, J=7.4 Hz, 3H). LC-MS: m/z 412.5 (M+H)⁺.

N-(4-(3-hydroxy-3-isobutylazetidine-1-carbonyl)phenyl)quinoline-8-sulfonamide (35)

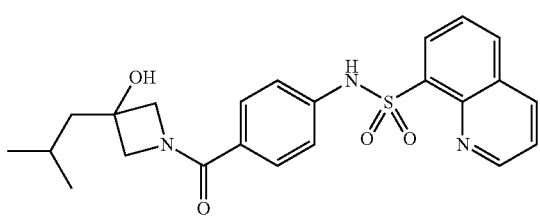 [SMILES: CC(C)CC1(O)CN(C(=O)c2ccc(NS(=O)(=O)c3cccc4cccnc34)cc2)C1]

¹H NMR (DMSO-d₆) δ: 10.56 (s, 1H), 9.12 (dd, J=4.2, 1.8 Hz, 1H), 8.52 (dd, J=8.4, 1.7 Hz, 1H), 8.44 (dd, J=7.4, 1.4 Hz, 1H), 8.29 (dd, J=8.3, 1.3 Hz, 1H), 7.81-7.66 (m, 2H), 7.39 (d, J=8.8 Hz, 2H), 7.13 (d, J=8.7 Hz, 2H), 5.52 (s, 1H), 4.07 (d, J=8.8 Hz, 1H), 3.94 (d, J=8.8 Hz, 1H), 3.84 (d, J=10.0 Hz, 1H), 3.76 (d, J=9.8 Hz, 1H), 1.80 (dt, J=13.5, 6.7 Hz, 1H), 1.51 (d, J=6.9 Hz, 2H), 0.85 (dd, J=13.2, 6.6 Hz, 6H). LC-MS: m/z 440.5 (M+H)⁺.

N-(4-(3-hydroxy-3-propylazetidine-1-carbonyl)phenyl)quinoline-8-sulfonamide (36)

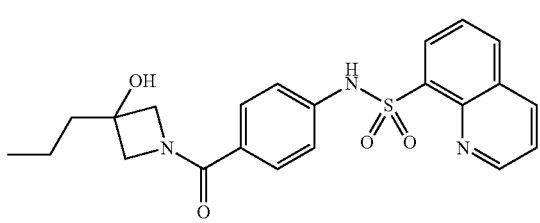 [SMILES: CCCC1(O)CN(C(=O)c2ccc(NS(=O)(=O)c3cccc4cccnc34)cc2)C1]

¹H NMR (CHLOROFORM-d) δ: 9.17 (dd, J=4.3, 1.7 Hz, 1H), 8.59 (s, 1H), 8.38 (dd, J=7.3, 1.3 Hz, 1H), 8.31 (dd, J=8.4, 1.6 Hz, 1H), 8.06 (dd, J=8.2, 1.3 Hz, 1H), 7.69-7.57 (m, 2H), 7.40 (d, J=8.6 Hz, 2H), 7.09 (d, J=8.6 Hz, 2H), 4.03 (d, J=40.8 Hz, 4H), 2.08 (s, 1H), 1.71 (dd, J=10.3, 6.1 Hz, 2H), 1.44-1.36 (m, 2H), 0.96 (t, J=7.3 Hz, 3H). LC-MS: m/z 426.5 (M+H)⁺.

Example 9

Scheme 4. Preparation of Compound 37

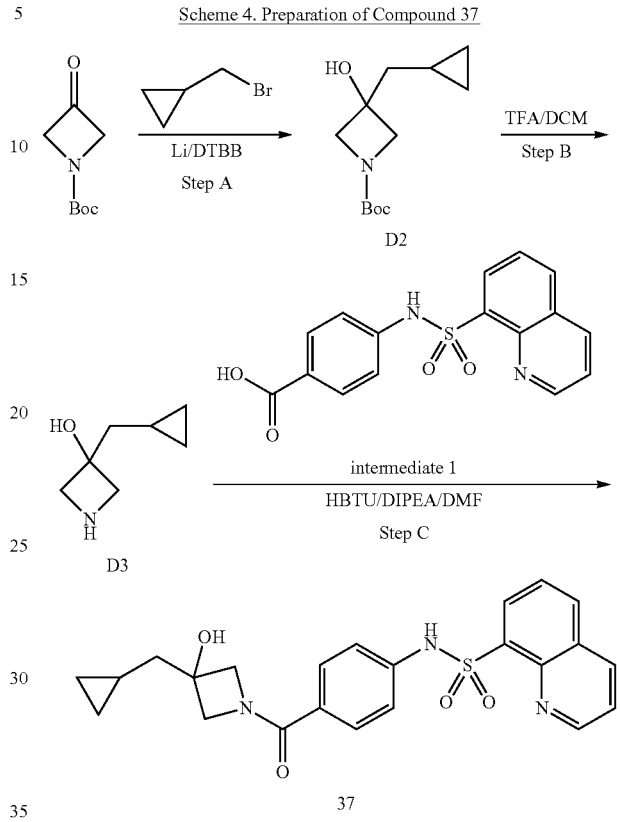

Step A: tert-butyl 3-(cyclopropylmethyl)-3-hydroxyazetidine-1-carboxylate (D2)

To a suspension of 4,4'-di-tButyl-biphenyl (DTBB) (30.33 mg, 0.114 mmol) and Li (56.7 mg, 8.09 mmol) in 50 mL of anhydrous THF was added dropwise a solution of (bromomethyl)cyclopropane (307.9 mg, 2.28 mmol) and tert-butyl 3-oxoazetidine-1-carboxylate (500 mg, 2.5 mmol) in anhydrous THF (5 mL) at −78° C. under N₂. The resulting mixture was stirred at −78° C. under N₂ for 8 h. The reaction mixture was quenched by sat. NH₄Cl aq. at −78° C. The resulting mixture was extracted with EtOAc (50 mL×2). The combined organic phase was washed with brine, dried over anhy. Na₂SO₄ and concentrated in vacuo. Column chromatography (15% PE/EtOAc) afforded 262.5 mg of title compound as a colorless liquid. ¹H NMR (CHLOROFORM-d) δ: 3.89 (dd, J=24.2, 9.0 Hz, 4H), 2.84 (s, 1H), 1.69 (d, J=6.7 Hz, 2H), 1.45 (s, 9H), 0.80-0.70 (m, 1H), 0.59-0.49 (m, 2H), 0.20-0.12 (m, 2H).

Step B: N-(4-(3-(cyclopropylmethyl)-3-hydroxyazetidine-1-carbonyl)phenyl)quinoline-8-sulfonamide (D3)

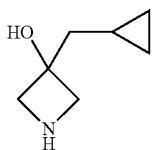

To a solution of compound D2 (1 eq.) in DCM, was added TFA (10 eq.), the reaction mixture was stirred at room temperature for about 2 hours, when LCMS detected no s.m. The reaction mixture was concentrated to afford the desired product D3 as the TFA salt. The crude product was used for the next step directly without further purification. LC-MS: m/z 128.2 (M+H)$^+$ N-(4-(3-(cyclopropylmethyl)-3-hydroxyazetidine-1-carbonyl)phenyl)quinoline-8-sulfonamide (37)

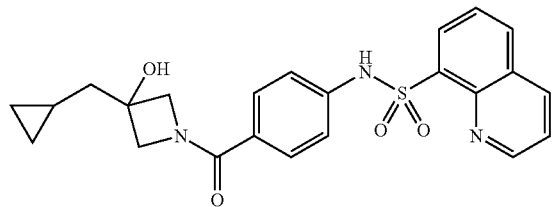 [SMILES: O=C(c1ccc(NS(=O)(=O)c2cccc3cccnc23)cc1)N1CC(O)(CC2CC2)C1]

To a round-bottomed flask was added 3-(cyclopropylmethyl)azetidin-3-ol (compound D3) (1 eq.), DMF (5 mL), DIPEA (3.0 eq.), HBTU (1.2 eq.), and intermediate 1 (1 eq.) sequentially. The reaction mixture was stirred at room temperature overnight or until TLC showed that the s.m. was consumed. The mixture was diluted with brine and extracted with ethyl acetate. The organic layer was dried with anhydrous Na$_2$SO$_4$, filtered, and the filtrate was concentrated. The desired product was purified by silica gel chromatography.
$^1$H NMR (CHLOROFORM-d) δ: 9.67 (s, 1H), 9.32 (d, J=4.0 Hz, 1H), 8.54 (t, J=6.6 Hz, 2H), 8.16 (d, J=7.6 Hz, 1H), 7.81 (dd, J=8.3, 4.9 Hz, 1H), 7.74 (t, J=7.8 Hz, 1H), 7.42 (d, J=8.6 Hz, 2H), 7.21 (d, J=8.3 Hz, 2H), 4.12 (dd, J=22.9, 10.1 Hz, 4H), 1.69 (d, J=6.7 Hz, 2H), 0.79-0.64 (m, 1H), 0.55 (q, J=5.4 Hz, 2H), 0.23-0.10 (m, 2H). LC-MS: m/z 438.6 (M+H)$^+$.

Example 10

Scheme 5. General Procedure 3

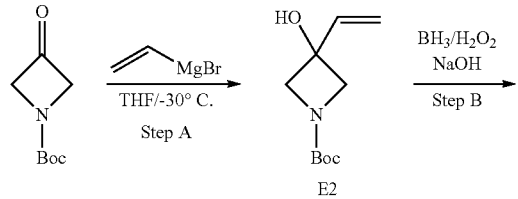

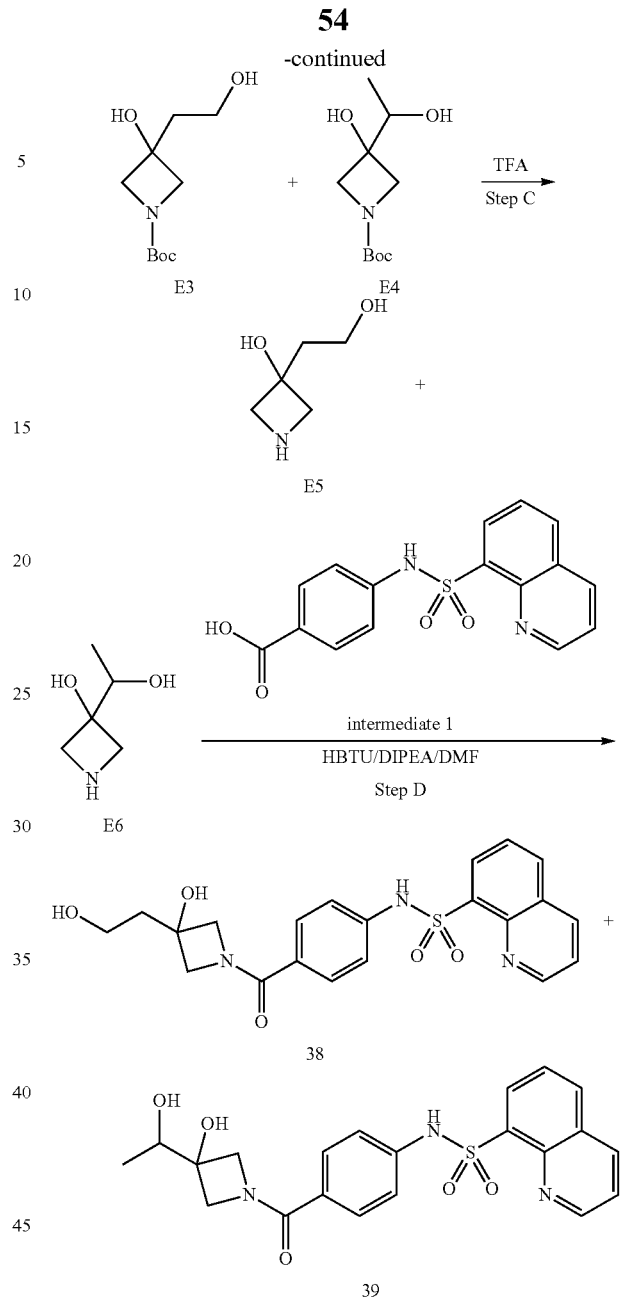

Step A: tert-butyl 3-hydroxy-3-vinylazetidine-1-carboxylate (E2)

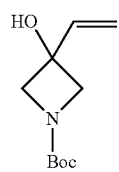

To a solution of Boc-3-azetidine (1 eq.) in THF was added dropwise vinylmagnesium bromide solution in THF (4 eq.) via a syringe at −30° C. After the addition, the resulting mixture was stirred at −30° C. under N$_2$ for 2 h, and then allowed to warm to r.t. The reaction mixture was quenched by sat. NH₄Cl aq., and the resulting mixture was extracted with EtOAc (50 mL, 30 mL). The combined organic phase was washed with brine, dried over anhydrous Na₂SO₄ and concentrated in vacuo. The residue was purified by column chromatography (PE/EtOAc) to afford compound E2. LC-MS: m/z 200.2 (M+H)⁺.

Step B: tert-butyl 3-hydroxy-3-(2-hydroxyethyl) azetidine-1-carboxylate and tert-butyl 3-hydroxy-3-(1-hydroxyethyl)azetidine-1-carboxylate (E3) & (E4)

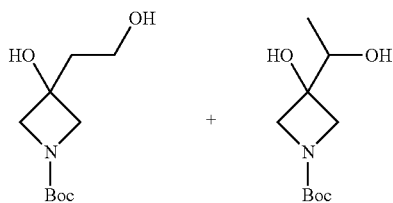

To a solution of compound E2 (1 eq.) in THF, was added a solution of BH₃ in THF (10 eq.) at 0° C., the reaction mixture was stirred at room temperature overnight. Then aqueous NaOH (20 eq.) was added slowly, followed by H₂O₂ (2 eq.), and the mixture was stirred for another 3 hrs, when LCMS detected no s.m. The reaction mixture was filtered, and the filtrate was concentrated to afford crude product. The crude product was purified by silica gel chromatography to obtain a mixture of compound E3 and E4. Compounds E3 and E4 were not separated but used together for the next step. LC-MS: m/z 218.3 (M+H)⁺.

Step C: 3-(2-hydroxyethyl)azetidin-3-ol and 3-(1-hydroxyethyl)azetidin-3-ol (E5) & (E6)

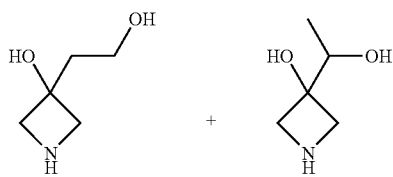

To a solution of compound E3 and E4 (1 eq.) in DCM, was added TFA (10 eq.), the reaction mixture was stirred at room temperature for about 2 hours, when LCMS detected no s.m. The reaction mixture was concentrated to afford the desired mixture of products E5 and E6 as TFA salts, which was used for the next step directly without further purification. LC-MS: m/z 118.3 (M+H)⁺.

Step D

To a round-bottomed flask was added the mixture of compound 5 and 6 (1 eq.), DMF (5 mL), DIPEA (3.0 eq.), HBTU (1.2 eq.), and intermediate 4 (1 eq.) sequentially. The reaction mixture was stirred at room temperature overnight or until TLC showed that s.m. was consumed. The mixture was diluted with brine, and extracted with ethyl acetate. The organic layer was dried with anhydrous Na₂SO₄, filtered, and the filtrate was concentrated. The desired product was purified by silica gel chromatography.

N-(4-(3-hydroxy-3-(2-hydroxyethyl)azetidine-1-carbonyl)phenyl)quinoline-8-sulfonamide (38)

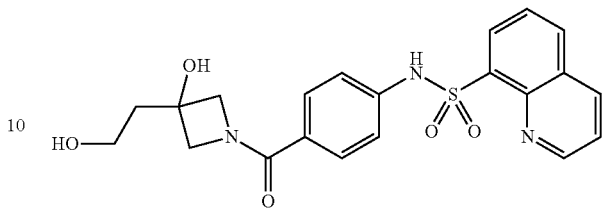

¹H NMR (CHLOROFORM-d) δ: 9.14 (dd, J=4.3, 1.8 Hz, 1H), 8.43 (ddd, J=5.9, 3.9, 1.6 Hz, 2H), 8.19 (dd, J=8.3, 1.3 Hz, 1H), 7.72-7.63 (m, 2H), 7.45-7.37 (m, 2H), 7.23-7.14 (m, 2H), 4.26 (d, J=9.2 Hz, 1H), 4.08 (dd, J=20.2, 10.4 Hz, 2H), 3.92 (d, J=10.9 Hz, 1H), 3.72 (t, J=6.4 Hz, 2H), 1.93 (t, J=6.4 Hz, 2H). LC-MS: m/z 428.6 (M+H)⁺.

N-(4-(3-hydroxy-3-(1-hydroxyethyl)azetidine-1-carbonyl)phenyl)quinoline-8-sulfonamide (39)

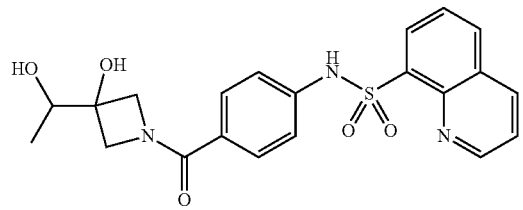 [SMILES: CC(O)C1(O)CN(C(=O)c2ccc(NS(=O)(=O)c3cccc4cccnc34)cc2)C1]

¹H NMR (CHLOROFORM-d) δ: 9.16 (d, J=2.8 Hz, 1H), 8.68 (s, 1H), 8.38 (d, J=7.0 Hz, 1H), 8.31 (d, J=7.2 Hz, 1H), 8.06 (d, J=8.0 Hz, 1H), 7.69-7.54 (m, 2H), 7.35 (d, J=8.5 Hz, 2H), 7.07 (d, J=8.2 Hz, 2H), 4.09 (ddd, J=60.3, 28.4, 22.5 Hz, 4H), 3.88 (dd, J=12.8, 6.4 Hz, 1H), 1.15 (d, J=4.6 Hz, 3H). LC-MS: m/z 428.6 (M+H)⁺.

Example 11

Scheme 6. General Procedure 4

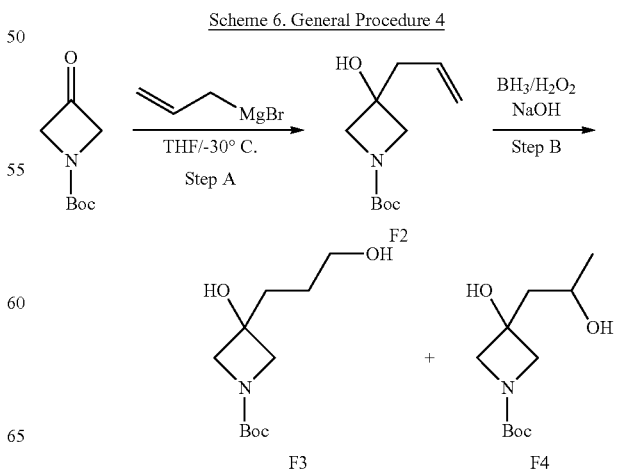

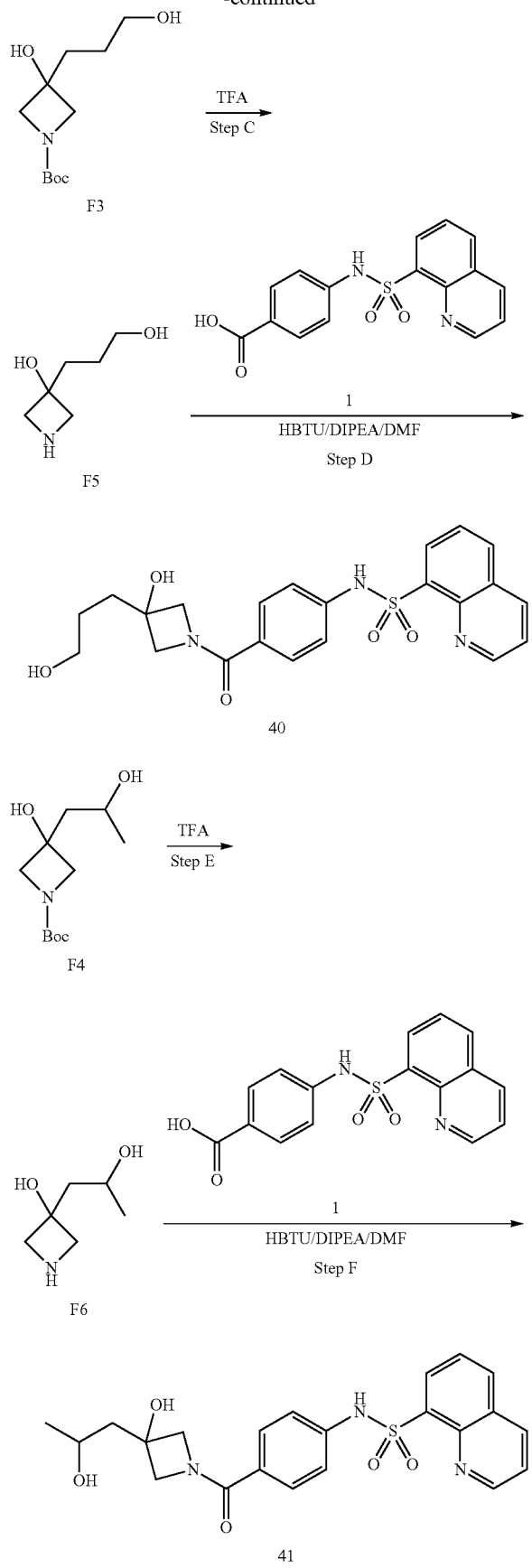

Step A: tert-butyl 3-allyl-3-hydroxyazetidine-1-carboxylate (F2)

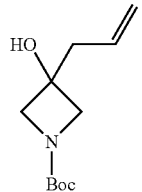

To a solution of Boc-3-azetidine (5.02 mmol), ally bromide (12.4 mmol), THF (1 mL) and saturated ammonium chloride solution (5 mL) was added zinc dust (10 mmol) portion wise at 10° C. After addition, the reaction mixture was stirred overnight, when TLC showed full conversion. The reaction mixture was diluted with water (5 mL) and 10% $H_2SO_4$ (aq) was added to achieve pH ~6. The mixture was extracted with ethyl acetate (3×). The organic layers were combined and washed with saturated solution of $NaHCO_3$ and brine, and finally dried over anhy. $Na_2SO_4$. Volatiles were evaporated to give compound F2 as colorless oil. LC-MS: m/z 214.3 $(M+H)^+$.

Step B

To a solution of compound F2 (1 eq.) in THF, was added a solution of $BH_3$ in THF (10 eq.) at 0° C., the reaction mixture was stirred at room temperature overnight. Aqueous NaOH (20 eq.) was added slowly, followed by $H_2O_2$ (2 eq.). The mixture was stirred for another 3 hrs, when LCMS detected no s.m. The reaction mixture was filtered, and the filtrate was concentrated to afford crude product. The crude product was purified by silica gel chromatography to obtain compounds F3 and F4. tert-butyl 3-hydroxy-3-(3-hydroxypropyl)azetidine-1-carboxylate (F3)

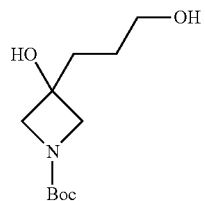 [SMILES: CC(C)(C)OC(=O)N1CC(O)(CCCO)C1]

$^1$H NMR (CHLOROFORM-d) δ: 3.84 (s, 16H), 3.68-3.75 (m, 12H), 3.06 (br. s., 14H), 1.90-1.97 (m, 8H), 1.68-1.78 (m, 12H), 1.45 (s, 38H). LC-MS: m/z 232.3 $(M+H)^+$.

tert-butyl 3-hydroxy-3-(2-hydroxypropyl)azetidine-1-carboxylate (F4)

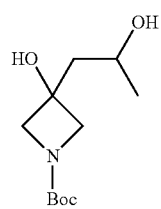

$^1$H NMR (CHLOROFORM-d) δ: 4.15-4.24 (m, 5H), 3.86-3.94 (m, 15H), 3.77-3.83 (m, 5H), 1.89-1.95 (m, 9H), 1.42-1.49 (m, 48H), 1.29-1.33 (m, 17H). LC-MS: m/z 232.3 $(M+H)^+$.

Step C: 3-(3-hydroxypropyl)azetidin-3-ol (F5)

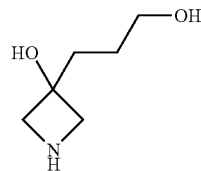

To a solution of compound 3 (1 eq.) in DCM was added TFA (10 eq.), and the reaction mixture was stirred at room temperature for about 2 hours, when LCMS detected no s.m. The reaction mixture was concentrated to afford compound 5 as the TFA salt. The crude product was used for the next step directly without further purification. LC-MS: m/z 132.2 (M+H)$^+$.

Step E: 3-(2-hydroxypropyl)azetidin-3-ol (F6)

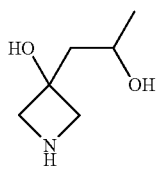

To a solution of compound F4 (1 eq.) in DCM, was added TFA (10 eq.), and the reaction mixture was stirred at room temperature for about 2 hours, when LCMS detected no s.m. The reaction mixture was concentrated to afford compound F6 as the TFA salt. The crude product was used for the next step directly without further purification. LC-MS: m/z 132.2 (M+H)$^+$.

Step D

To a round-bottomed flask was added the mixture of compound F5 (1 eq.), DMF (5 mL), DIPEA (3.0 eq.), HBTU (1.2 eq.), and intermediate 1 (1 eq.) sequentially. The reaction mixture was stirred at room temperature overnight or until TLC showed that s.m. was consumed. The mixture was diluted with brine and extracted with ethyl acetate. The organic layer was dried with anhydrous Na$_2$SO$_4$ and filtered, and the filtrate was concentrated. The desired product was purified by silica gel chromatography.

N-(4-(3-hydroxy-3-(3-hydroxypropyl)azetidine-1-carbonyl)phenyl)quinoline-8-sulfonamide (40)

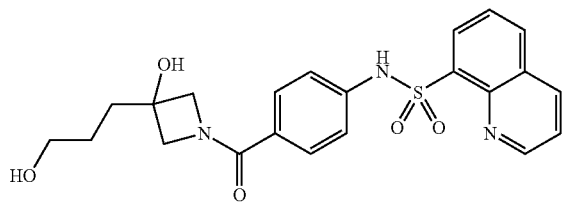 [SMILES: O=C(c1ccc(NS(=O)(=O)c2cccc3cccnc23)cc1)N1CC(O)(CCCO)C1]

$^1$H NMR (CHLOROFORM-d) δ: 9.21 (dd, J=4.4, 1.8 Hz, 1H), 8.82 (br. s., 1H), 8.39 (dd, J=12.0, 1.5 Hz, 1H), 8.32-8.46 (m, 1H), 8.08 (dd, J=8.2, 1.5 Hz, 1H), 7.60-7.74 (m, 2H), 7.38-7.44 (m, J=8.5 Hz, 2H), 7.08-7.16 (m, J=8.8 Hz, 2H), 4.06 (br. s., 4H), 3.75 (t, J=5.4 Hz, 2H), 1.91-1.97 (m, 2H), 1.68-1.75 (m, 2H). LC-MS: m/z 442.5 (M+H)$^+$.

Step F

To a round-bottomed flask was added the mixture of compound F6 (1 eq.), DMF (5 mL), DIPEA (3.0 eq.), HBTU (1.2 eq.), and intermediate 1 (1 eq.) sequentially. The reaction mixture was stirred at room temperature overnight or until TLC showed that s.m. was consumed. The mixture was diluted with brine and extracted with ethyl acetate. The organic layer was dried with anhydrous Na$_2$SO$_4$, filtered, and the filtrate was concentrated. The desired product was purified by silica gel chromatography.

The following compound was also prepared via Example 11.

N-(4-(3-hydroxy-3-(2-hydroxypropyl)azetidine-1-carbonyl)phenyl)quinoline-8-sulfonamide (41)

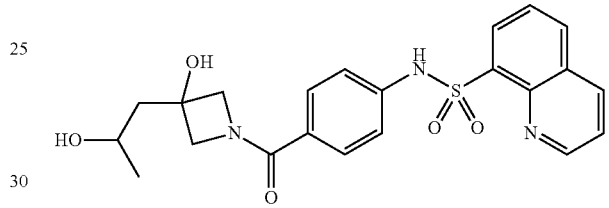

$^1$H NMR (CHLOROFORM-d) δ: 10.56 (s, 1H), 9.12 (dd, J=4.2, 1.7 Hz, 1H), 8.52 (dd, J=8.4, 1.6 Hz, 1H), 8.44 (dd, J=7.3, 1.2 Hz, 1H), 8.29 (dd, J=8.2, 1.1 Hz, 1H), 7.81-7.67 (m, 2H), 7.38 (d, J=7.9 Hz, 2H), 7.13 (d, J=8.6 Hz, 2H), 5.65 (s, 1H), 4.44 (dt, J=18.2, 8.9 Hz, 1H), 4.26-3.93 (m, 2H), 3.81 (dt, J=19.3, 10.2 Hz, 2H), 3.17 (d, J=5.2 Hz, 1H), 1.81-1.55 (m, 2H), 1.05 (dd, J=13.4, 6.6 Hz, 3H). LC-MS: m/z 442.6 (M+H)$^+$.

Example 12

Scheme 7. Preparation of Compound 42.

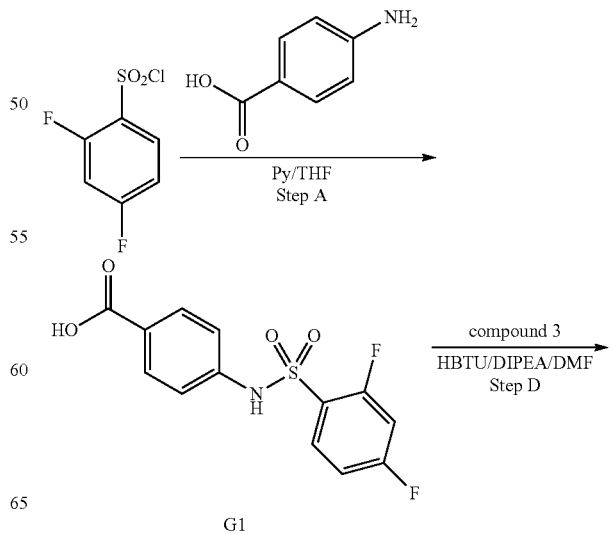

-continued

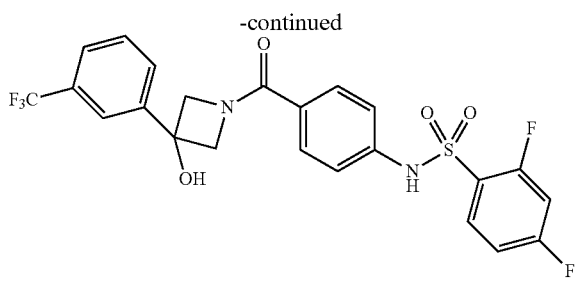

42

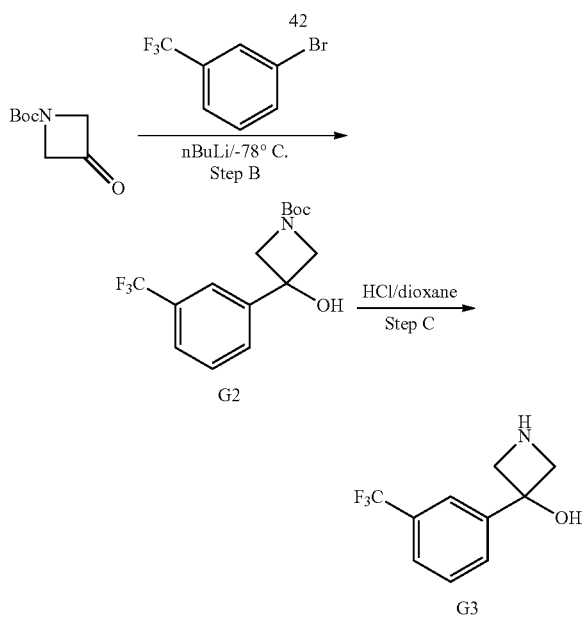

G3

Step A: 4-(2,4-difluorophenylsulfonamido)benzoic acid (G1)

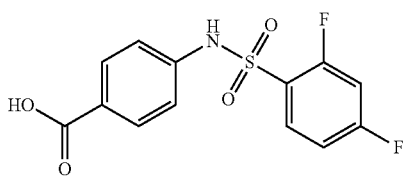 [SMILES: O=C(O)c1ccc(NS(=O)(=O)c2ccc(F)cc2F)cc1]

To a solution of 4-aminobenzoic acid (622 mg, 4.5 mmol) in 10 mL of anhydrous THF was added pyridine (0.9 g, 9 mmol), 2,4-difluorobenzene-1-sulfonyl chloride (1.1 g, 5.0 mmol) at 0° C. The resulting mixture was stirred at 70° C. overnight. After filtration and the residue were washed with EtOH and compound G1 was obtained as white solid. LC-MS: m/z 314.3 (M+H)⁺.

Step B: tert-butyl 3-hydroxy-3-(3-(trifluoromethyl) phenyl)azetidine-1-carboxylate (G2)

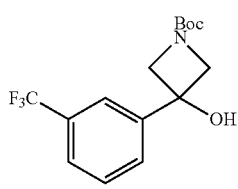 [SMILES: CC(C)(C)OC(=O)N1CC(O)(c2cccc(C(F)(F)F)c2)C1]

To a solution of 1-bromo-3-(trifluoromethyl)benzene (1.0 eq.) in dry THF was added a solution of n-BuLi in THF (1.05 eq.) dropwise at −78° C. After the addition, the mixture was stirred at −78° C. for about 0.5 hour. Then a solution of Boc-3-azetidine in THF was added dropwise via a syringe at −78° C. After the addition, the resulting mixture was stirred at −78° C. under N₂ for 2 h, and then allowed to warm to r.t. The reaction mixture was quenched by sat. NH₄Cl aq., and the mixture was extracted with EtOAc (50 mL, 30 mL). The combined organic phase was washed with brine, dried over anhydrous Na₂SO₄ and concentrated in vacuo. The residue was purified by column chromatography (PE/EtOAc) to afford compound G2. LC-MS: m/z 318.3 (M+H)⁺.

Step C: 3-(3-(trifluoromethyl)phenyl)azetidin-3-ol (G3)

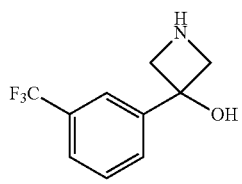 [SMILES: OC1(c2cccc(C(F)(F)F)c2)CNC1]

To a solution of compound G2 (1 eq.) in dioxane, was added a solution of HCl in dioxane (3 eq.), and the reaction mixture was stirred at room temperature for about 2 hours, when LCMS detected no s.m. The reaction mixture was concentrated to afford compound G3. Crude product was used in the next step without further purification. LC-MS: m/z 218.3 (M+H)⁺.

Step D

To a round-bottomed flask was added compound G2 (1 eq.), DMF (5 mL), DIPEA (3.0 eq.), HBTU (1.2 eq.), and intermediate G1 (1 eq.) sequentially. The reaction mixture was stirred at room temperature overnight or until TLC showed that s.m. was consumed. The mixture was diluted with brine and extracted with ethyl acetate. The organic layer was dried with anhydrous Na₂SO₄, filtered, and the filtrate was concentrated. The desired product was purified by silica gel chromatography.

2,4-difluoro-N-(4-(3-hydroxy-3-(3-(trifluoromethyl) phenyl)azetidine-1-carbonyl)phenyl)benzenesulfonamide (42)

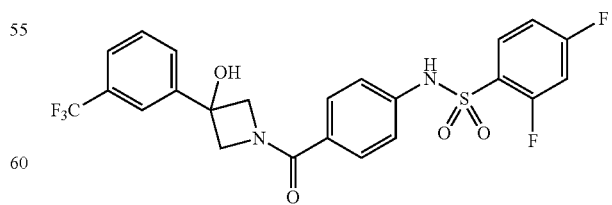

¹H NMR (CHLOROFORM-d) δ: 7.93 (d, J=6.2 Hz, 1H), 7.80 (s, 1H), 7.71 (d, J=7.3 Hz, 1H), 7.53-7.66 (m, 4H), 7.12-7.25 (m, 3H), 6.90-7.03 (m, 2H), 4.44-4.65 (m, 4H). LC-MS: m/z 513.4 (M+H)⁺

Example 13

Scheme 8. General Procedure 5.

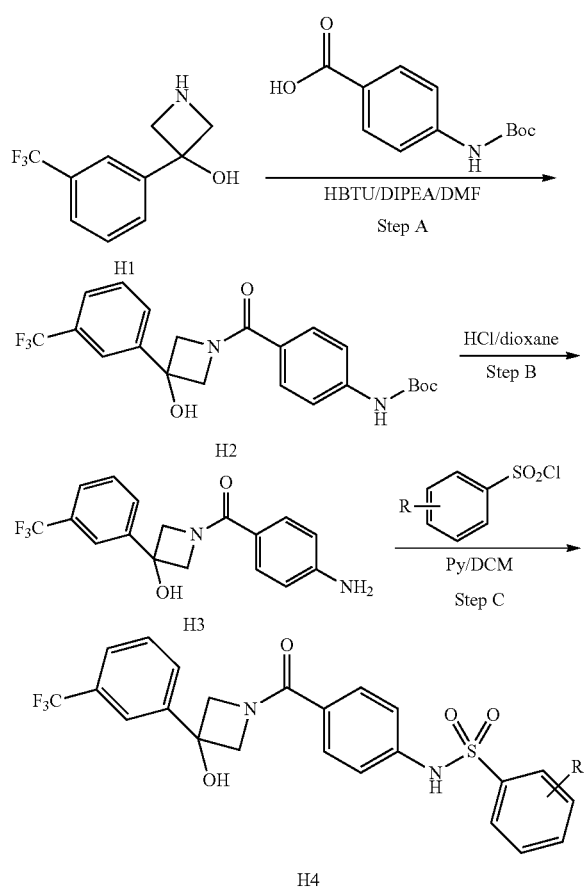

Step A: tert-butyl 4-(3-hydroxy-3-(3-(trifluoromethyl)phenyl)azetidine-1-carbonyl)phenylcarbamate (H2)

To a round-bottomed flask was added compound H1 (1 eq.), DMF (5 mL), DIPEA (3.0 eq.), HBTU (1.2 eq.), and 4-(tert-butoxycarbonylamino)benzoic acid (1 eq.) sequentially. The reaction mixture was stirred at room temperature overnight or until TLC showed that s.m. was consumed. The mixture was diluted with brine and extracted with ethyl acetate. The organic layer was dried with anhydrous $Na_2SO_4$, filtered, and the filtrate was concentrated. The desired product was purified by silica gel chromatography. LC-MS: m/z 437.4 (M+H)$^+$.

Step B: (4-aminophenyl)(3-hydroxy-3-(3-(trifluoromethyl)phenyl)azetidin-1-yl)methanone (H3)

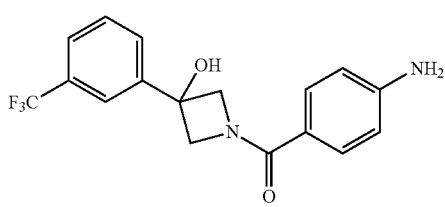 [SMILES: Nc1ccc(C(=O)N2CC(O)(c3cccc(C(F)(F)F)c3)C2)cc1]

To a solution of compound H2 (1 eq.) in dioxane, was added a solution of HCl in dioxane (3 eq.), and the reaction mixture was stirred at room temperature for about 2 hours, when LCMS detected no s. m. The reaction mixture was concentrated to afford the desired product H3. Crude product was used in the next step without further purification. LC-MS: m/z 337.3 (M+H)$^+$.

Step C

To a solution of (4-aminophenyl)(3-hydroxy-3-(3-(trifluoromethyl)phenyl)azetidin-1-yl) methanone (H2, 1 eq.) in DCM, was added pyridine (2 eq.), and the corresponding aryl sulfonyl chloride (1.1 eq.). The resulting mixture was stirred at room temperature overnight. The mixture was washed with brine, the organic layer was concentrated, and the residue was purified by silica gel chromatography to obtain the desired product.

N-(4-(3-hydroxy-3-(3-(trifluoromethyl)phenyl)azetidine-1-carbonyl)phenyl)isoquinoline-5-sulfonamide
(43)

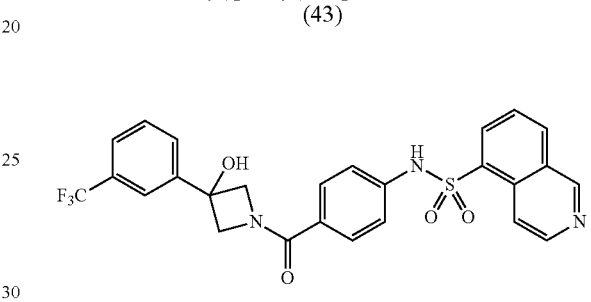

$^1$H NMR (DMSO-d$_6$) δ: 11.21 (s, 1H), 9.47 (s, 1H), 8.73 (d, J=6.2 Hz, 1H), 8.39-8.57 (m, 3H), 7.77-7.96 (m, 3H), 7.47-7.73 (m, 4H), 7.11 (d, J=8.8 Hz, 2H), 6.62 (s, 1H), 4.56 (br. s., 1H), 4.28 (br. s., 1H), 4.21 (br. s., 2H). LC-MS: m/z 528.5 (M+H)$^+$.

N-(4-(3-hydroxy-3-(3-(trifluoromethyl)phenyl)azetidine-1-carbonyl)phenyl)quinoline-5-sulfonamide
(44)

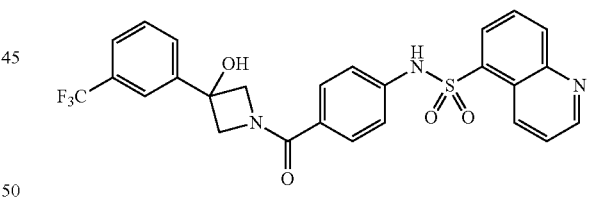

$^1$H NMR (CHLOROFORM-d) δ: 8.99-9.08 (m, 2H), 8.23-8.48 (m, 2H), 7.74-7.86 (m, 2H), 7.70 (d, J=8.2 Hz, 1H), 7.50-7.65 (m, 6H), 7.22 (s, 1H), 7.04 (d, J=8.5 Hz, 2H), 4.47 (br. s., 4H). LC-MS: m/z 528.5 (M+H)$^+$.

Example 14

Scheme 9. General Procedure 6.

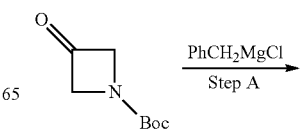

Step A: tert-butyl 3-benzyl-3-hydroxyazetidine-1-carboxylate (J2)

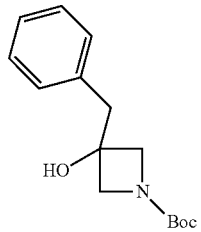 [SMILES: CC(C)(C)OC(=O)N1CC(O)(Cc2ccccc2)C1]

Boc-3-azetidine (10 g, 58.47 mmol) was taken in a dry THF (60 mL). The mixture was cooled to −78° C. and stirred for 15 min. A solution of benzyl magnesium chloride (17.64 g, 116.9 mmol) 2M in THF was added over 15 min at −78° C. under nitrogen atmosphere. The resulting mixture was allowed to warm up to rt and stirred for 4 hrs. The progress of the reaction was monitored by TLC. Upon completion of reaction the reaction mixture was quenched with sat. ammonium chloride solution (500 mL) and extracted with EtOAc. The combined organic layers were washed with water, dried over $Na_2SO_4$ and concentrated under reduced pressure. The crude product was purified by column chromatography using silica gel (100-200 mesh) and 10% EtOAc in Hexane to afford the desired compound J2 as colorless oil. Yield: −7 g (45.31%). $^1$H NMR (CHLOROFORM-d) δ: 7.36-7.29 (m, 3H), 7.26-7.21 (m, 2H), 3.98 (d, 2H, J=9.2 Hz), 3.80 (d, 2H, J=9.2 Hz), 3.04 (s, 2H), 1.37 (s, 9H).

Step B: 3-benzylazetidin-3-ol (J3)

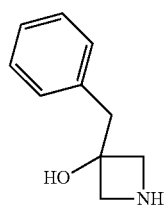 [SMILES: OC1(Cc2ccccc2)CNC1]

Compound J2 (1 eq.) was dissolved in DCM and cooled to 0° C. TFA (10 eq.) was added at 0° C., and the reaction mixture was stirred for 3-4 hrs at room temperature until LCMS and TLC confirmed completion of the reaction. The reaction mixture was concentrated to dryness, triturated 3 to 4 times with DCM and washed with n-pentane to afford the desired TFA salt of compound J3 as an off-white solid. Yield 70%. $^1$H NMR (DMSO-$d_6$) δ: 9.40 (bs, 1H), 8.81 (bs, 1H), 730-7.21 (m, 5H), 4.53-4.48 (m, 2H), 4.07-4.06 (m, 2H), 2.24 (s, 2H).

Step C

To a solution of compound J4 (1 eq.) in a mixture (1:1) DCM and Pyridine, sulfonyl chloride (1.2 eq.) was added slowly at room temperature under nitrogen atmosphere. The resulting mixture was allowed to stir at room temperature for

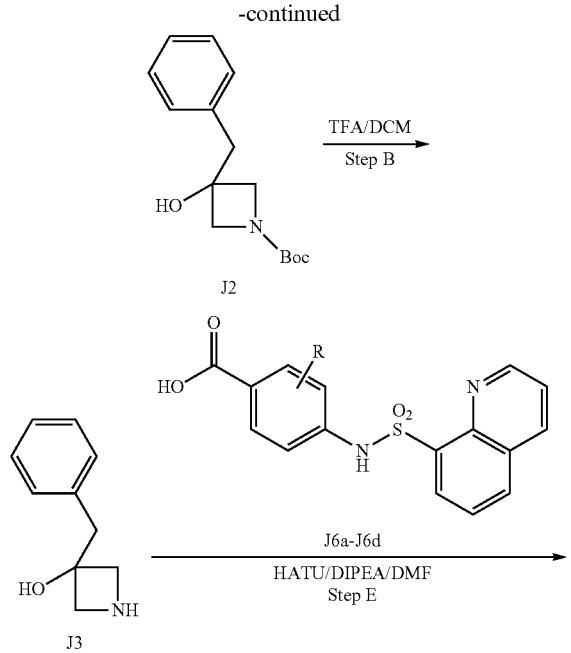

J5a-J5d
a: R = 2-F
b: R = 3-F
c: R= 3-Me
d: R = 2-OMe

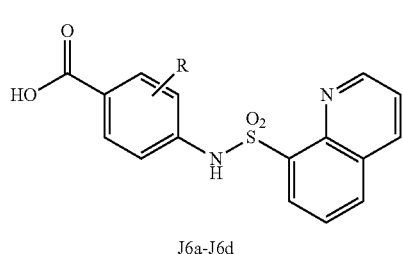

J6a-J6d 16 hrs. The progress of the reaction was monitored by TLC. After completion of reaction, the crude mixture was diluted with DCM and washed with water followed 1N HCl. The resulting organic layer was then dried over Na₂SO₄ and concentrated under reduced pressure. The resulting solid was triturated with diethyl-ether to afford the desired compound J5.

J5a: methyl 2-fluoro-4-(quinoline-8-sulfonamido)benzoate

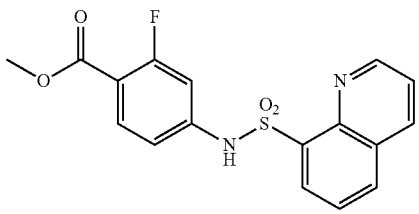 [SMILES: COC(=O)c1ccc(NS(=O)(=O)c2cccc3cccnc23)cc1F]

¹H NMR (DMSO-d₆) δ: 11.03 (s, 1H), 9.10-9.09 (m, 1H), 8.52-8.50 (m, 2H), 8.31 (d, 1H, J=8 Hz), 7.79-7.61 (m, 3H), 7.02-6.95 (m, 2H), 4.16 (q, 2H, J=7.2 Hz), 1.20 (t, 3H, J=6.8 Hz). LC-MS: m/z 375.0

J5b: methyl 3-fluoro-4-(quinoline-8-sulfonamido)benzoate

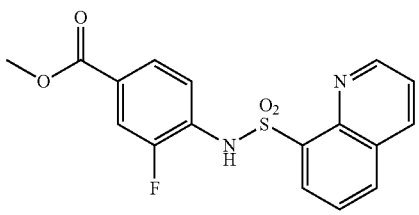 [SMILES: COC(=O)c1ccc(NS(=O)(=O)c2cccc3cccnc23)c(F)c1]

¹H NMR (DMSO-d₆) δ: 10.23 (bs, 1H), 9.04 (dd, 1H, J=1.6 Hz), 8.54 (dd, 1H, J=1.6 Hz & 1.2 Hz), 8.35-8.30 (m, 2H), 7.74-7.70 (m, 2H), 7.64 (m, 1H), 7.53-7.48 (m, 2H), 4.22 (q, 2H, J=6.8 Hz), 1.24 (t, 3H, J=6.8 Hz). LC-MS: m/z 375.0

J5c: methyl 3-methyl-4-(quinoline-8-sulfonamido)benzoate

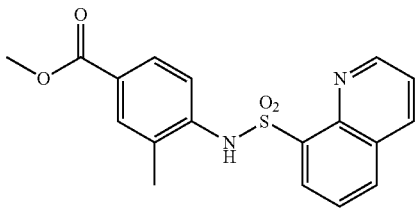 [SMILES: COC(=O)c1ccc(NS(=O)(=O)c2cccc3cccnc23)c(C)c1]

¹H NMR (DMSO-d₆) δ: 9.50 (bs, 1H), 9.12-9.11 (m, 1H), 8.55 (d, 1H, J=8.4 Hz), 8.30 (d, 2H, J=6.8 Hz), 7.75-7.69 (m, 2H), 7.26 (d, 2H, J=8.8 Hz), 4.20 (q, 2H, J=7.2 Hz), 2.09 (s, 3H), 1.22 (t, 3H, J=7.2 Hz). LC-MS: m/z 370.9

J5d: methyl 2-methoxy-4-(quinoline-8-sulfonamido)benzoate

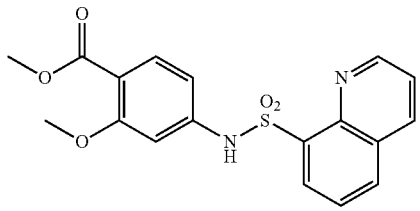 [SMILES: COC(=O)c1ccc(NS(=O)(=O)c2cccc3cccnc23)cc1OC]

¹H NMR (DMSO-d6) δ: 10.6 (bs, 1H), 9.12-9.11 (m, 1H), 8.50 (t, 2H, J=7.6 Hz), 8.29 (d, 1H, J=8 Hz), 7.77-7.68 (m, 2H), 7.42 (d, 1H, J=8.4 Hz), 6.86 (s, 1H), 6.69 (d, 1H, J=8.4 Hz), 3.63 (s, 3H), 3.61 (s, 3H). LC-MS: m/z 372.9

Step D

To a solution of compound J5 (1 eq.) in a THF and water (1:1) was added LiOH.H₂O (5 eq.). The resulting mixture was allowed to stir at 80° C. for 15 hrs. The progress of the reaction was monitored by TLC. After completion of reaction, the crude mixture was washed with EtOAc. The aqueous layer was acidified with citric acid and filtered. The resulting solid was then washed with water and azeotroped with toluene under reduced pressure to afford acid compound J6 as white solid.

J6a: 2-fluoro-4-(quinoline-8-sulfonamido)benzoic acid

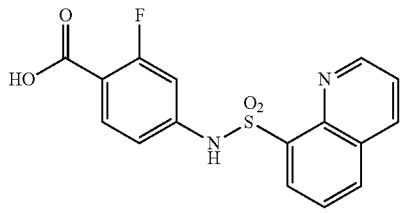 [SMILES: O=C(O)c1ccc(NS(=O)(=O)c2cccc3cccnc23)cc1F]

¹H NMR (DMSO-d₆) δ: 12.69 (bs, 1H), 10.98 (bs, 1H), 9.109-9.100 (m, 1H), 8.53-8.49 (m, 2H), 8.32-8.27 (m, 1H), 7.79-7.69 (m, 2H), 7.61 (t, 1H, J=8.4 Hz), 6.99-6.93 (m, 2H). LC-MS: m/z 347.1

J6b: 3-fluoro-4-(quinoline-8-sulfonamido)benzoic acid

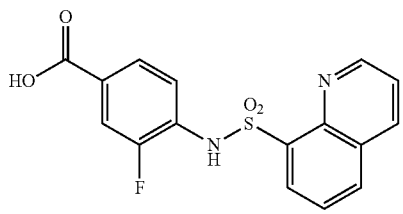 [SMILES: O=C(O)c1ccc(NS(=O)(=O)c2cccc3cccnc23)c(F)c1]

¹H NMR (DMSO-d₆) δ: 12.94 (bs, 1H), 10.14 (bs, 1H), 9.059-9.052 (m, 1H), 8.54 (d, 1H, J=8.4 Hz), 8.32 (t, 2H, J=8.4 Hz), 7.72 (t, 2H, J=6.8 Hz), 7.62 (d, 1H, 8.4 Hz), 7.51-7.45 (m, 2H). LC-MS: m/z 347.1

J6c: 3-methyl-4-(quinoline-8-sulfonamido)benzoic acid

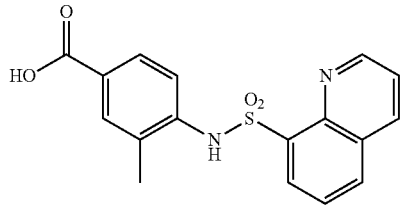 [SMILES: Cc1cc(C(=O)O)ccc1NS(=O)(=O)c1cccc2cccnc12]

¹H NMR (DMSO-d$_6$) δ: 9.65 (bs, 1H), 9.12-9.11 (m, 1H), 8.55 (d, 1H, J=8 Hz), 8.30 (d, 2H, J=7.6 Hz), 7.75-7.69 (m, 2H), 7.60-7.54 (m, 2H), 7.19 (d, 1H, J=8 Hz), 2.08 (s, 3H). LC-MS: m/z 342.9

J6d: 2-methoxy-4-(quinoline-8-sulfonamido)benzoic acid

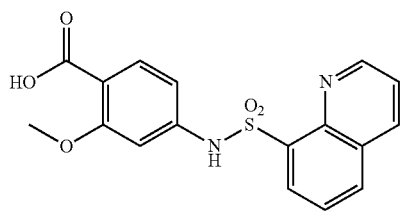 [SMILES: COc1cc(NS(=O)(=O)c2cccc3cccnc23)ccc1C(=O)O]

¹H NMR (DMSO-d$_6$) δ: 11.39 (bs, 2H), 9.12-9.11 (m, 1H), 8.51-8.46 (m, 2H), 8.28 (d, 1H, J=8 Hz), 7.75-7.68 (m, 2H), 7.39 (d, 1H, J=8.4 Hz), 6.81 (s, 1H), 6.65 (d, 1H, J=8.4 Hz), 3.59 (s, 3H). LC-MS: m/z 358.9

Step E

To a solution of respective compounds J6 (1 eq.) in DMF, compound J3 (3 eq.) was added followed by addition of DIPEA (10 eq.) and HATU (1.5 eq.) at room temperature under nitrogen atmosphere. The resulting mixture was allowed to stir at room temperature for 16 hrs. The progress of the reaction was monitored by TLC. Upon completion of the reaction, the crude mixture was diluted with EtOAc and washed with water, followed saturated sodium bicarbonate. The resulting organic layer was then separated and dried over Na$_2$SO$_4$, and concentrated under reduced pressure. The resulting crude product was purified by column chromatography using silica gel (100-200 mesh) and 0.5% MeOH in DCM to afford the desired product.

N-(4-(3-benzyl-3-hydroxyazetidine-1-carbonyl)-3-fluorophenyl)quinoline-8-sulfonamide (45)

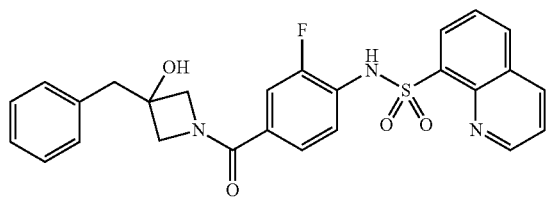 [SMILES: O=C(c1ccc(NS(=O)(=O)c2cccc3cccnc23)c(F)c1)N1CC(O)(Cc2ccccc2)C1]

¹H NMR (DMSO-d$_6$) δ: 9.10 (bs, 1H), 8.47-8.39 (m, 2H), 8.18 (d, 1H, J=8.4 Hz), 7.70-7.62 (m, 2H), 7.27-7.18 (m, 5H), 7.03-6.96 (m, 2H), 4.60-4.58 (m, 2H), 4.27-4.11 (m, 2H), 2.26 (s, 2H). LC-MS: m/z 492.1.

N-(4-(3-benzyl-3-hydroxyazetidine-1-carbonyl)-2-fluorophenyl)quinoline-8-sulfonamide (46)

¹H NMR (DMSO-d$_6$) δ: 9.08-9.07 (m, 1H), 8.44-8.39 (m, 2H), 8.20 (d, 1H, J=8 Hz), 7.69-7.63 (m, 3H), 7.36 (d, 1H, J=8.4 Hz), 7.27-7.15 (m, 6H), 4.63 (d, 1H, J=10.8 Hz), 4.40 (d, 1H, J=9.6 Hz), 4.28 (d, 1H, J=10.4 Hz), 2.81 (s, 2H), 2.30 (s, 3H). LC-MS: m/z 492.1.

Example 15

Scheme 10. General Procedure 7.

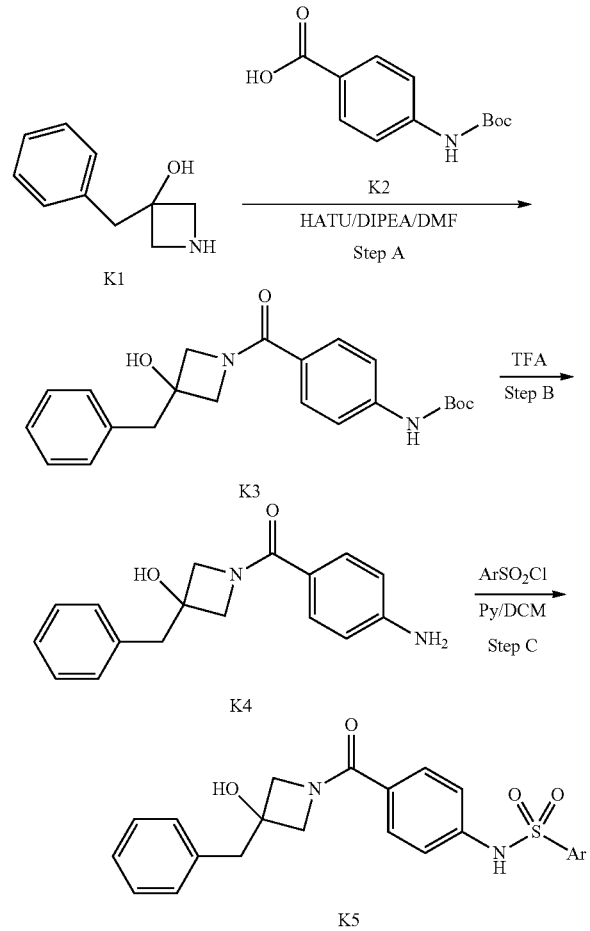

Step A: tert-butyl 4-(3-benzyl-3-hydroxyazetidine-1-carbonyl)phenylcarbamate (K3)

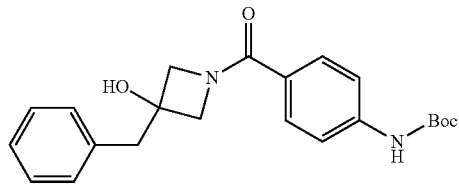 [SMILES: CC(C)(C)OC(=O)Nc1ccc(C(=O)N2CC(O)(Cc3ccccc3)C2)cc1]

To a solution of compound K1 (1 eq.) in DMF, compound K2 (3 eq.) was added followed by addition of DIPEA (10 eq.) and HATU (1.5 eq.) at room temperature under nitrogen atmosphere. The resulting mixture was allowed to stir at room temperature for 16 hrs. The progress of the reaction was monitored by TLC. Upon completion of the reaction, the crude mixture was diluted with EtOAc and washed with water followed saturated sodium bicarbonate. The resulting organic layer was then separated, dried over $Na_2SO_4$, and concentrated under reduced pressure to obtain crude product. The crude product was purified by column chromatography using silica gel (100-200 mesh) and 0.5% MeOH in DCM to afford the desired compound K3. LC-MS: m/z 383.1

Step B: (4-aminophenyl)(3-benzyl-3-hydroxyazetidin-1-yl)methanone (K4)

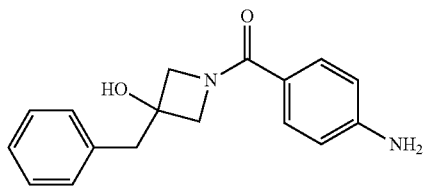 [SMILES: Nc1ccc(C(=O)N2CC(O)(Cc3ccccc3)C2)cc1]

Compound K3 (1 eq.) was dissolved in DCM and cooled to 0° C. TFA (10 eq.) was then added at 0° C., and the reaction mixture was stirred for 3-4 hrs at room temperature until LCMS and TLC confirmed completion of the reaction. The reaction mixture was concentrated to dryness, triturated 3 to 4 times with DCM and washed with n-pentane to afford the desired TFA salt of compound K4 as light brown solid. $^1$H NMR (DMSO-$d_6$) δ: 7.44 (d, 2H, J=8 Hz), 7.32-7.16 (m, 5H), 6.66 (d, 2H, J=8.4 Hz), 4.80 (m, 2H), 4.37 (m, 2H), 2.29 (s, 2H). LC-MS: m/z 283.1.

Step C

Compound K4 (1 eq.) was taken in pyridine (10 eq.) and stirred for 30 minutes at r.t. The reaction mixture was then cooled to 0° C., and sulfonyl chloride ($ArSO_2Cl$) (2 eq.) was added. The resulting reaction mixture was allowed to warm up to room temperature and stirred for 15 hrs. The progress of the reaction was monitored by TLC. Upon completion of reaction, the mixture was quenched with water and extracted with DCM. The combined organic layers were washed with water, dried over $Na_2SO_4$ and concentrated under reduced pressure. The crude product was purified by prep HPLC to afford the desired product as TFA salt. The TFA salt of final sulfonamide target was dissolved in EtOAc, and washed with sat. solution of $NaHCO_3$. The combined organic layers was again washed with $NaHCO_3$, dried over $Na_2SO_4$ and concentrated under reduced pressure afford the desired target as off white solid.

The following compounds were prepared via Example 15.

N-(4-(3-benzyl-3-hydroxyazetidine-1-carbonyl)phenyl)isoquinoline-5-sulfonamide (48)

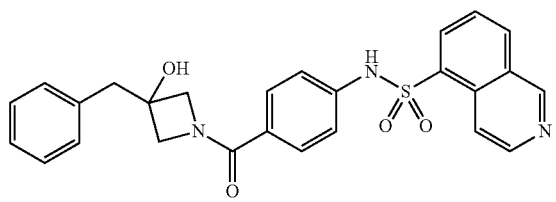 [SMILES: O=C(c1ccc(NS(=O)(=O)c2cccc3cnccc23)cc1)N1CC(O)(Cc2ccccc2)C1]

$^1$H NMR (DMSO-$d_6$) δ: 11.17 (bs, 1H), 9.45 (s, 1H), 8.71 (d, 1H, J=6 Hz), 8.49 (d, 1H, J=6.4 Hz), 8.43 (d, 1H, J=8 Hz), 7.82 (t, 1H, J=7.6 Hz), 7.49(d, 2H, J=8.4 Hz), 7.26 (d, 1H, J=7.6 Hz), 7.20-7.13 (m, 5H), 7.08 (d, 1H, J=8 Hz), 6.10 (s, 1H), 4.73 (d, 1H, J=8.8 Hz), 4.48 (d, 1H, J=9.6 Hz), 4.28 (d, 1H, J=8.8 Hz), 4.13 (d, 1H, J=10 Hz), 2.24 (s, 2H). LC-MS: m/z 474.1

N-(4-(3-benzyl-3-hydroxyazetidine-1-carbonyl)phenyl)-2-chlorobenzenesulfonamide (49)

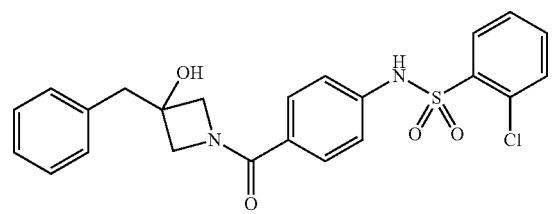 [SMILES: O=C(c1ccc(NS(=O)(=O)c2ccccc2Cl)cc1)N1CC(O)(Cc2ccccc2)C1]

$^1$H NMR (DMSO-$d_6$) δ: 11.03 (bs, 1H), 8.10 (d, 1H, J=7.6 Hz), 7.64-7.63 (m, 1H), 7.54 (d, 4H, J=8.4 Hz), 7.30-7.11 (m, 6H), 6.12 (s, 1H), 4.79 (d, 1H, J=8.8 Hz), 4.50 (d, 1H, J=10 Hz), 4.16 (d, 1H, J=10.8 Hz), 2.26 (s, 2H). LC-MS: m/z 457.1

N-(4-(3-benzyl-3-hydroxyazetidine-1-carbonyl)phenyl)-4-(trifluoromethyl)benzenesulfonamide (50)

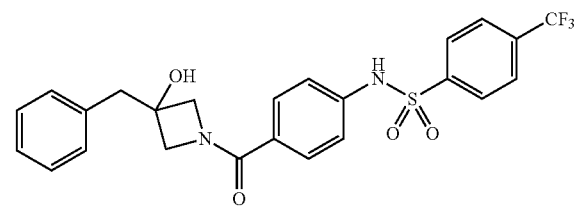 [SMILES: O=C(c1ccc(NS(=O)(=O)c2ccc(C(F)(F)F)cc2)cc1)N1CC(O)(Cc2ccccc2)C1]

$^1$H NMR (DMSO-$d_6$) δ: 10.91 (s, 1H), 8.15-7.90 (m, 4H), 7.58 (d, 2H, J=8.4 Hz), 7.28 (d, 1H, J=6.8 Hz), 7.24-7.05 (m, 5H), 6.13 (s, 1H), 4.79 (d, 1H, J=8.8 Hz), 4.52 (d, 1H, J=10.8 Hz), 4.34 (d, 1H, J=8.8 Hz), 4.17 (d, 1H, J=10.4 Hz), 2.26 (s, 2H). LC-MS: m/z 491.1

N-(4-(3-benzyl-3-hydroxyazetidine-1-carbonyl)phenyl)-2-(trifluoromethyl)benzenesulfonamide (51)

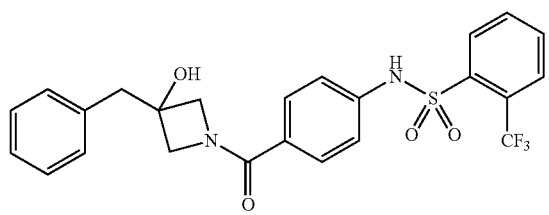

¹H NMR (DMSO-d₆) δ: 11.00 (bs, 1H), 8.12 (d, 1H, J=7.2 Hz), 8.02 (d, 1H, J=7.2 Hz), 7.91-7.80 (m, 2H), 7.59 (d, 2H, J=8.4 Hz), 7.29 (d, 1H, J=7.2 Hz), 7.22-7.10 (m, 5H), 6.14 (s, 1H), 4.79 (d, 1H, J=8.8 Hz), 4.52 (d, 1H, J=10.8 Hz), 4.34 (d, 1H, J=8.8 Hz), 4.17 (d, 1H, J=10.4 Hz), 2.27 (s, 2H). LC-MS: m/z 491.1

N-(4-(3-benzyl-3-hydroxyazetidine-1-carbonyl)phenyl)-2,3-dichlorobenzenesulfonamide (52)

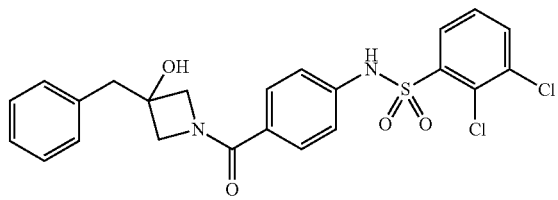 [SMILES: O=C(c1ccc(NS(=O)(=O)c2cccc(Cl)c2Cl)cc1)N1CC(O)(Cc2ccccc2)C1]

¹H NMR (DMSO-d₆) δ: 11.18 (bs, 1H), 8.09 (d, 1H, J=6.8 Hz), 7.49 (d, 1H, J=8 Hz), 7.59-7.55 (m, 3H), 7.30-7.12 (m, 6H), 4.79 (d, 1H, J=8.8 Hz), 4.51 (d, 1H, J=10.8 Hz), 4.34 (d, 1H, J=8.4 Hz), 4.16 (d, 1H, J=10.4 Hz), 2.26 (s, 2H). LC-MS: m/z 491.1

N-(4-(3-benzyl-3-hydroxyazetidine-1-carbonyl)phenyl)-2,3-dihydrobenzo[b][1,4]dioxine-5-sulfonamide (53)

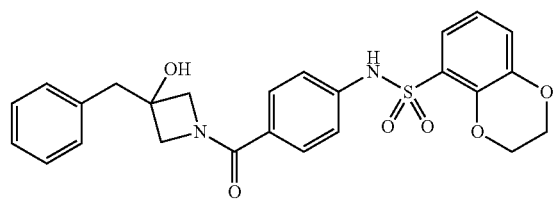 [SMILES: O=C(c1ccc(NS(=O)(=O)c2cccc3c2OCCO3)cc1)N1CC(O)(Cc2ccccc2)C1]

¹H NMR (DMSO-d₆) δ: 10.46 (s, 1H), 7.55 (d, 2H, J=8.4 Hz), 7.37-7.26(m, 2H), 7.22-7.08(m, 6H), 6.25-6.05 (m, 1H), 4.80(d, 1H, J=8.4 Hz), 4.50 (d, 1H, J=10.4 Hz), 4.34(d, 1H, J=9.2 Hz), 4.29-4.26 (m, 4H), 4.16 (d, 1H, J=10.8 Hz). LC-MS: m/z 481.1.

Example 16

Scheme 10. Preparation of Compound 54.

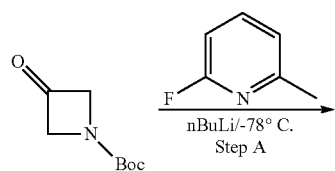

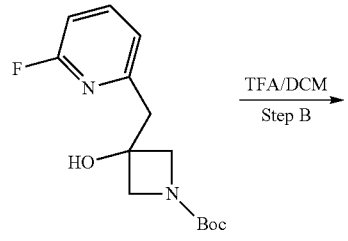

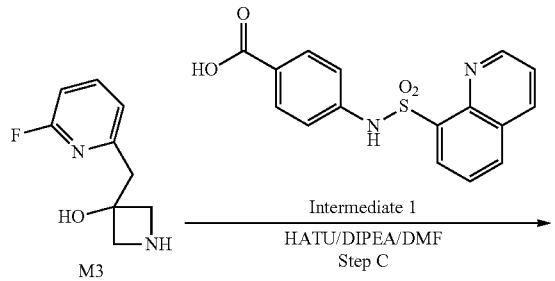

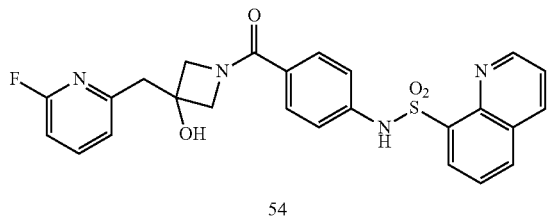

Step A: tert-butyl 3-((6-fluoropyridin-2-yl)methyl)-3-hydroxyazetidine-1-carboxylate (M2)

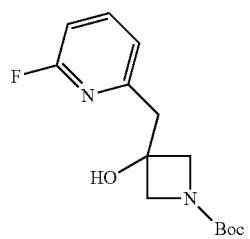 [SMILES: CC(C)(C)OC(=O)N1CC(O)(Cc2cccc(F)n2)C1]

2-fluoro-6-methylpyridine (1 eq.) was taken in dry THF and cooled to −78° C. A solution of n-Butyl lithium (1.2 eq) 2.5M in hexane was added to the above reaction mixture over 15 min at −78° C. under nitrogen atmosphere and stirred for 30 min at the same temperature. The reaction mixture was then stirred at −5° C. for 30 min and cooled to −78° C. A solution of tert-butyl 3-oxoazetidine-1-carboxylate (0.9 eq.) in THF was added over a period of 15 min. The resulting reaction mixture was then allowed to stir at room temperature for 16 hrs. The progress of the reaction was monitored by TLC. Upon completion of the reaction, the mixture was quenched with sat. ammonium chloride solution (500 mL) and extracted with EtOAc. The combined organic layers were washed with water, dried over Na₂SO₄ and concentrated under reduced pressure. The crude product was purified by column chromatography using silica gel (100-200 mesh) and 10% EtOAc in Hexane to afford the desired product M2 as light yellow oil.

$^1$H NMR (CHLOROFORM-d) δ: 7.80-7.74 (m, 1H), 7.11 (d, 1H, J=8 Hz), 6.85 (d, 1H, J=8 Hz), 5.27 (bs, 1H), 3.90 (d, 2H, J=9.6 Hz), 3.79 (d, 2H, J=9.6 Hz), 3.20 (s, 2H), 1.43 (s, 9H). LC-MS: m/z 283.1.

Step B: 3-((6-fluoropyridin-2-yl)methyl)azetidin-3-ol (M3)

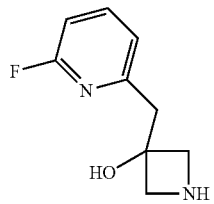 [SMILES: OC1(Cc2cccc(F)n2)CNC1]

Compound M2 (1 eq.) was dissolved in DCM and cooled to 0° C., followed by addition of TFA (10 eq.) at 0° C. The reaction mixture was then stirred for 3-4 hrs at room temperature until LCMS and TLC confirmed completion of the reaction. The reaction mixture was concentrated to dryness, triturated 3 to 4 times with DCM and washed with n-pentane to afford the TFA salt of compound M3 as colorless oil. The crude product was used directly for the next step without purification. LC-MS: m/z 183.1

Step C

To a solution of compound M3 (1 eq.) in DMF, intermediate 1 (3 eq.) was added followed by addition of DIPEA (10 eq.) and HATU (1.5 eq.) at room temperature under nitrogen atmosphere. The resulting mixture was allowed to stir at room temperature for 16 hrs. The progress of the reaction was monitored by TLC. Upon completion of the reaction, the crude mixture was diluted with EtOAc and washed successively with water and satd. sodium bicarbonate solution. The resulting organic layer was then separated, dried over Na$_2$SO$_4$ and concentrated under reduced pressure to obtain the crude product which was purified by column chromatography using silica gel (100-200 mesh) and 0.5% MeOH in DCM to afford the desired product.

N-(4-(3-((6-fluoropyridin-2-yl)methyl)-3-hydroxyazetidine-1-carbonyl)phenyl)quinoline-8-sulfonamide (54)

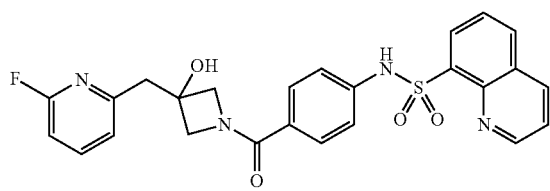 [SMILES: O=C(c1ccc(NS(=O)(=O)c2cccc3cccnc23)cc1)N1CC(O)(Cc2cccc(F)n2)C1]

$^1$H NMR (DMSO-d$_6$) δ: 9.12-9.11 (s, 1H), 8.47 (dd, 2H, J=8.4 Hz & J=7.2), 8.28 (d, 1H, J=7.2 Hz), 7.87-7.69 (m, 3H), 7.33 (d, 2H, J=8.4 Hz), 7.20 (d, 1H, J=7.2 Hz), 7.12 (d, 2H, J=7.2 Hz), 4.29 (d, 1H, J=8 Hz), 4.11 (d, 1H, J=9.2 Hz), 3.99 (d, 1H, J=8.4 Hz), 3.74 (d, 1H, J=9.6 Hz), 2.99 (s, 2H). LC-MS: m/z 493.2

The following compounds were also prepared via Example 16.

Compound 55 (Using 2-Methylpyridine as Starting Material)

N-(4-(3-hydroxy-3-(pyridin-2-ylmethyl)azetidine-1-carbonyl)phenyl)quinoline-8-sulfonamide (55)

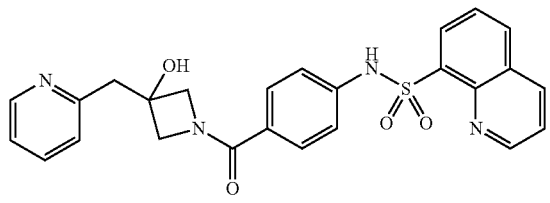 [SMILES: O=C(c1ccc(NS(=O)(=O)c2cccc3cccnc23)cc1)N1CC(O)(Cc2ccccn2)C1]

$^1$H NMR (DMSO-d$_6$): δ 10.53 (bs, 1H), 9.12-911 (m, 1H), 8.47 (dd, 2H, J=8 Hz & J=7.2 Hz), 8.39-8.38 (m, 1H), 8.28 (d, 1H, J=8 Hz), 7.75-7.63 (m, 3H), 7.32-7.10 (m,6H), 5.87 (s, 1H), 4.28 (d, 1H, J=7.2 Hz), 4.10 (d, 1H, J=8.8 Hz), 3.98 (d, 1H, J=7.6 Hz), 3.74-3.72 (d, 1H, J=8.8 Hz), 3.02 (s, 2H). LC-MS: m/z 475.2

Compound 56 (Using 2,6-Dimethylpyridine as Starting Material)

N-(4-(3-hydroxy-3-((6-methylpyridin-2-yl)methyl)azetidine-1-carbonyl)phenyl)quinoline-8-sulfonamide (56)

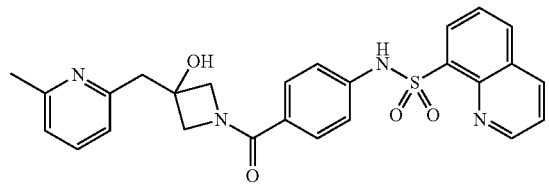 [SMILES: Cc1cccc(CC2(O)CN(C(=O)c3ccc(NS(=O)(=O)c4cccc5cccnc45)cc3)C2)n1]

$^1$H NMR (CDCl$_3$): δ 9.14-9.13 (m, 1H), 8.52 (s, 1H), 8.35-8.27 (m, 2H), 8.02 (d, 1H, J=8 Hz), 7.62-7.51 (m, 3H), 8.4 (d, 2H, J=8.4 Hz), 7.05-6.94 (m, 5H), 4.18-4.16 (m, 1H), 4.02-3.95 (m, 3H), 2.80 (s, 2H), 2.49 (s, 3H). LC-MS: m/z 489.2.

Having thus described several aspects of several embodiments, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A compound of Formula (I):

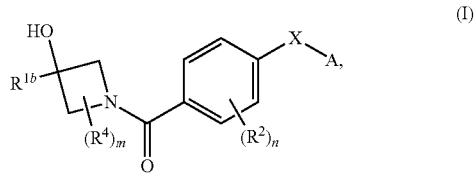

or a pharmaceutically acceptable salt thereof, wherein:

A is aryl or heteroaryl, wherein the aryl or heteroaryl is optionally substituted, and the aryl or heteroaryl is optionally fused to an optionally substituted carbocyclyl or an optionally substituted heterocyclyl;

X is selected from —NH—S(O)₂—, —N(alkyl)-S(O)₂—, —S(O)₂—NH— and —S(O)₂—N(alkyl)-;

R$^{1b}$ is C$_{2-8}$ alkyl, cycloalkyl, aryl, heteroaryl, cycloalkylalkyl, aralkyl or heteroaralkyl, wherein each aryl is substituted and each C$_{2-8}$ alkyl, cycloalkyl, cycloalkylalkyl, aralkyl, heteroaryl or heteroaralkyl is optionally substituted;

each R² is independently selected from halo and haloalkyl;

each R⁴ is independently selected from alkyl, alkoxy, haloalkyl and hydroxyl;

n is 0, 1 or 2; and m is 0, 1 or 2;

wherein when R$^{1b}$ is unsubstituted benzyl, X is —NH—S(O)₂— and A is quinolin-8-yl; then n is 1.

2. The compound of claim 1, wherein A is an optionally substituted bicyclic heteroaryl.

3. The compound of claim 2, wherein A is an optionally substituted quinolin-8-yl.

4. The compound of claim 2, wherein A is an optionally substituted substituted isoquinolin-5-yl.

5. The compound of claim 1, wherein A is an optionally substituted monocyclic aryl (e.g., optionally substituted phenyl).

6. The compound of claim 1, wherein A is phenyl substituted with two substituents on adjacent carbons which form an optionally substituted heterocyclyl or carbocyclyl ring.

7. The compound of claim 1, wherein X is —NH—S(O)₂—or —N(alkyl)-S(O)₂—.

8. The compound of claim 1, wherein the compound has the structure set forth in formula (II) or a pharmaceutically acceptable salt thereof:

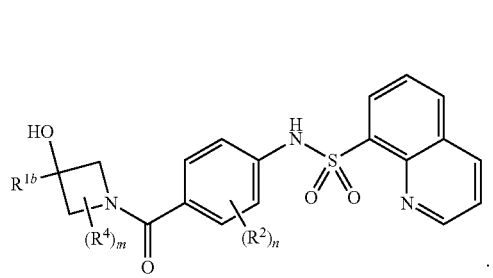

(II)

9. The compound of claim 1, wherein R$^{1b}$ is optionally substituted aralkyl.

10. The compound of claim 1, wherein R$^{1b}$ is optionally substituted heteroaralkyl.

11. The compound of claim 1, wherein R$^{1b}$ is optionally substituted C$_{2-8}$ alkyl.

12. The compound of claim 1, wherein R$^{1b}$ is cycloalkyl or cycloalkylalkyl.

13. The compound of claim 1, selected from any one of the compounds below:

| Structure |
| --- |
| 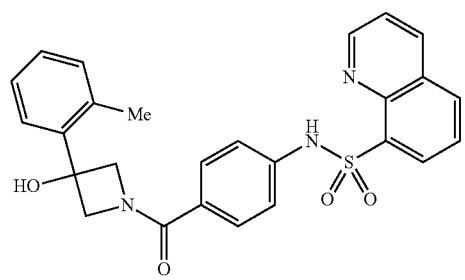 [SMILES: Cc1ccccc1C1(O)CN(C(=O)c2ccc(NS(=O)(=O)c3cccc4cccnc34)cc2)C1] |
| 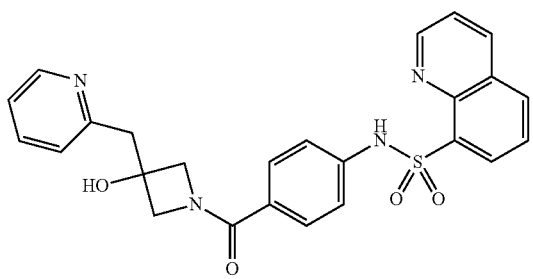 [SMILES: O=C(c1ccc(NS(=O)(=O)c2cccc3cccnc23)cc1)N1CC(O)(Cc2ccccn2)C1] |
| 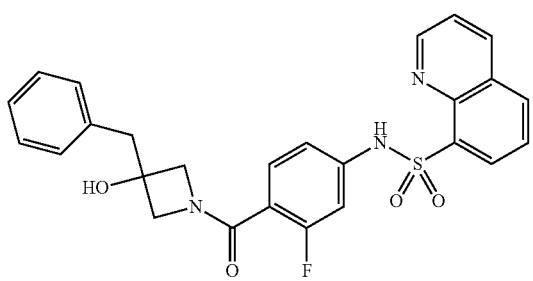 [SMILES: O=C(c1ccc(NS(=O)(=O)c2cccc3cccnc23)cc1F)N1CC(O)(Cc2ccccc2)C1] |
| 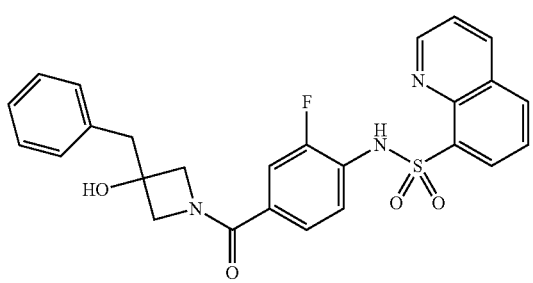 [SMILES: O=C(c1ccc(NS(=O)(=O)c2cccc3cccnc23)c(F)c1)N1CC(O)(Cc2ccccc2)C1] |
| 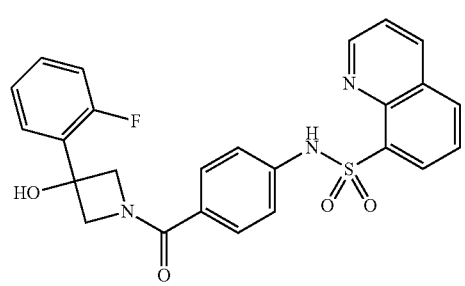 [SMILES: O=C(c1ccc(NS(=O)(=O)c2cccc3cccnc23)cc1)N1CC(O)(c2ccccc2F)C1] |

| Structure | | Structure |
|---|---|---|
| 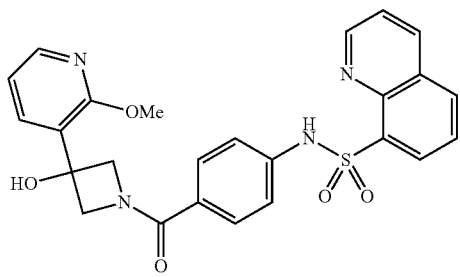 [SMILES: COc1ncccc1C1(O)CN(C(=O)c2ccc(NS(=O)(=O)c3cccc4cccnc34)cc2)C1] | | 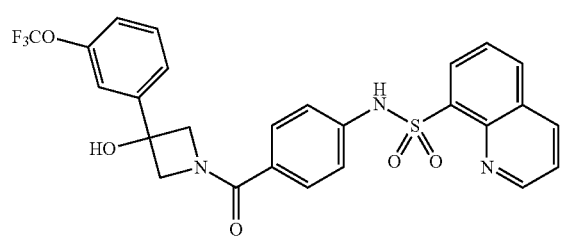 |
| 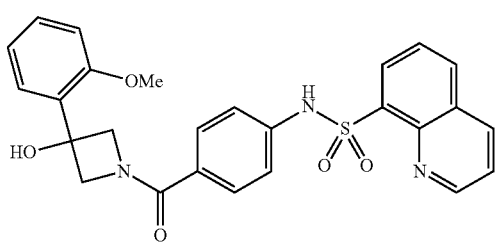 [SMILES: COc1ccccc1C1(O)CN(C(=O)c2ccc(NS(=O)(=O)c3cccc4cccnc34)cc2)C1] | | 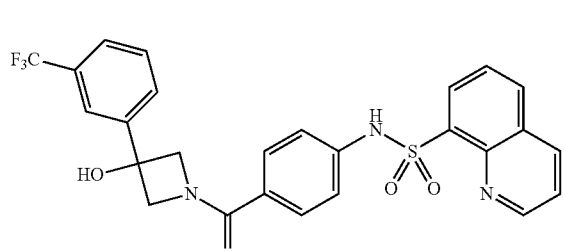 |
| 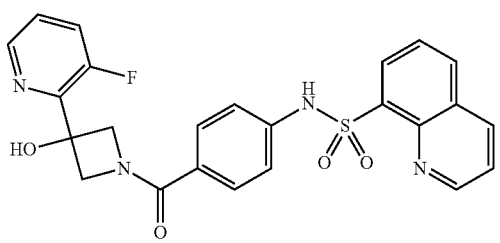 [SMILES: O=C(c1ccc(NS(=O)(=O)c2cccc3cccnc23)cc1)N1CC(O)(c2ncccc2F)C1] | | 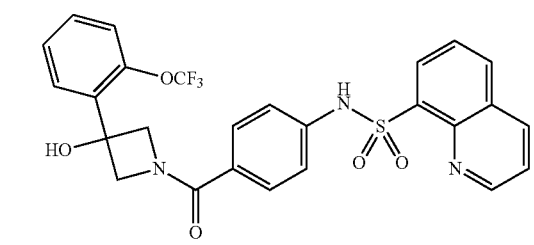 |
| 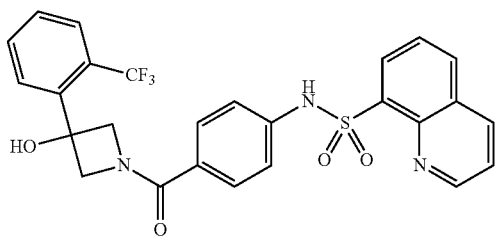 [SMILES: O=C(c1ccc(NS(=O)(=O)c2cccc3cccnc23)cc1)N1CC(O)(c2ccccc2C(F)(F)F)C1] | | 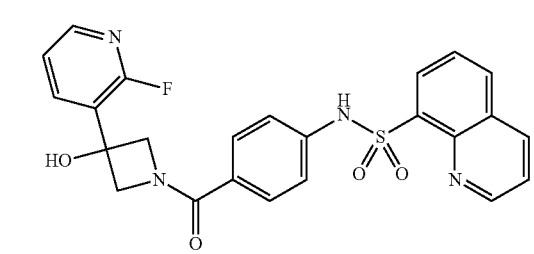 |
| 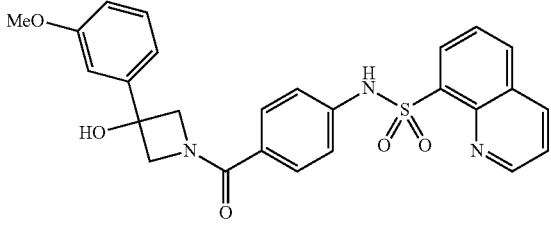 [SMILES: COc1cccc(C2(O)CN(C(=O)c3ccc(NS(=O)(=O)c4cccc5cccnc45)cc3)C2)c1] | | 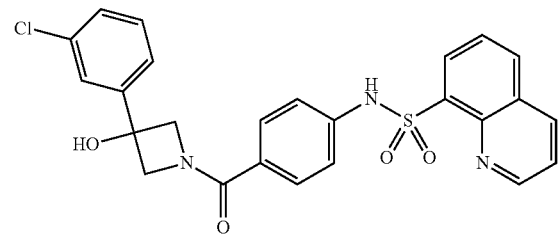 |
| 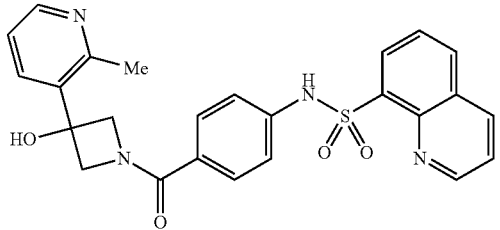 [SMILES: Cc1ncccc1C1(O)CN(C(=O)c2ccc(NS(=O)(=O)c3cccc4cccnc34)cc2)C1] | | 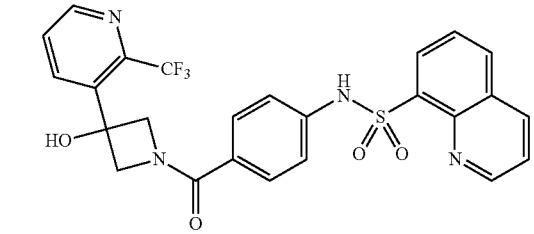 |

| Structure | | Structure |
|---|---|---|
| 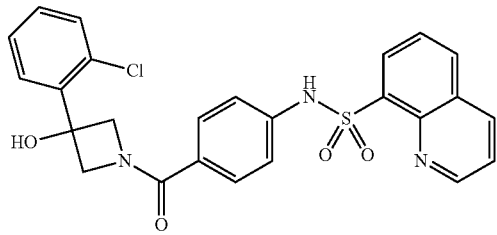 [SMILES: O=C(c1ccc(NS(=O)(=O)c2cccc3cccnc23)cc1)N1CC(O)(c2ccccc2Cl)C1] | | 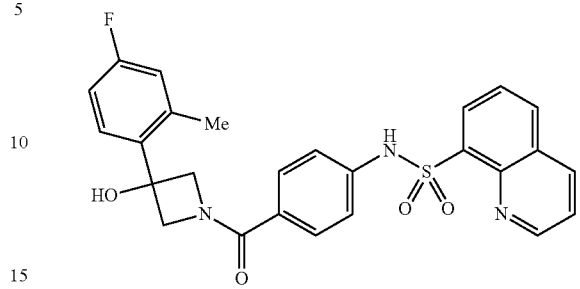 |
| 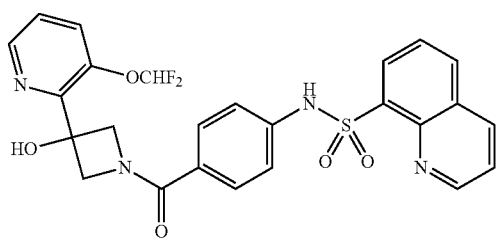 [SMILES: O=C(c1ccc(NS(=O)(=O)c2cccc3cccnc23)cc1)N1CC(O)(c2ncccc2OC(F)F)C1] | | 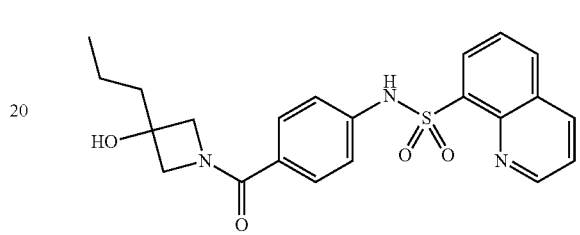 |
| 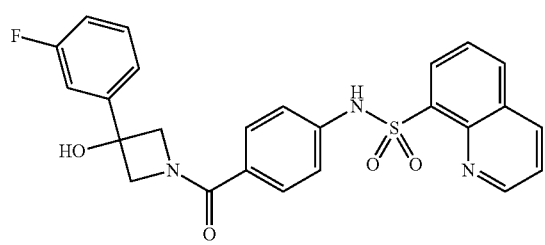 [SMILES: O=C(c1ccc(NS(=O)(=O)c2cccc3cccnc23)cc1)N1CC(O)(c2cccc(F)c2)C1] | | 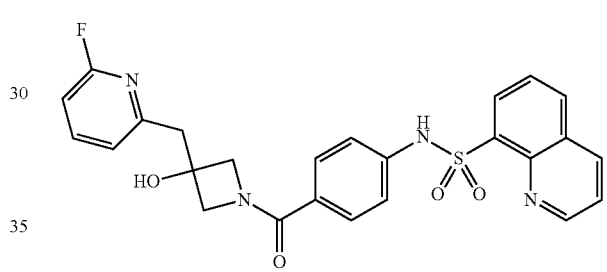 |
| 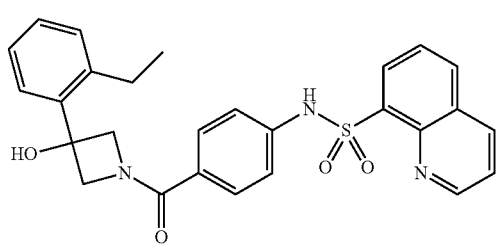 [SMILES: CCc1ccccc1C1(O)CN(C(=O)c2ccc(NS(=O)(=O)c3cccc4cccnc34)cc2)C1] | | 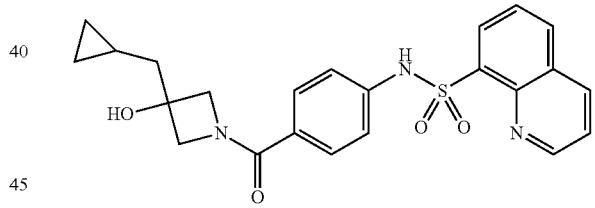 |
| 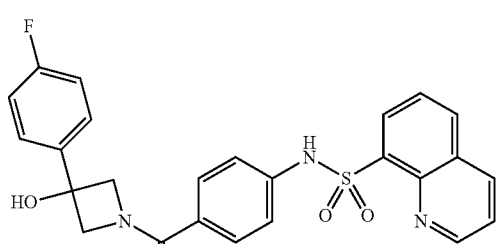 | | 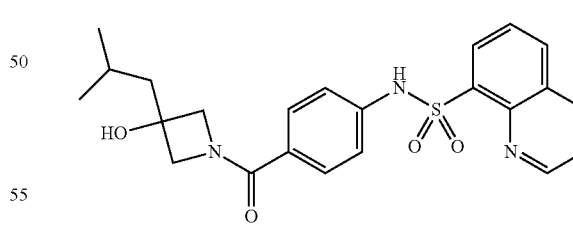 |
| 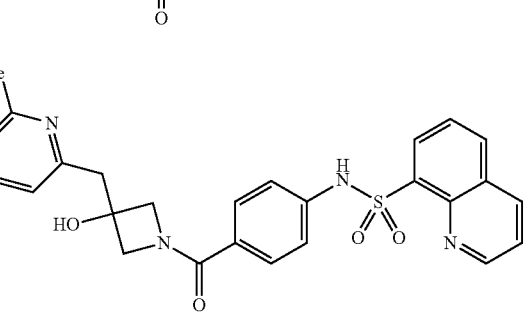 | | 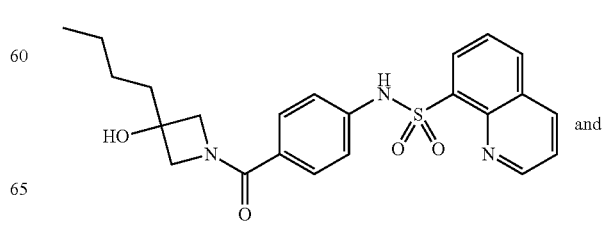 and |

-continued

Structure

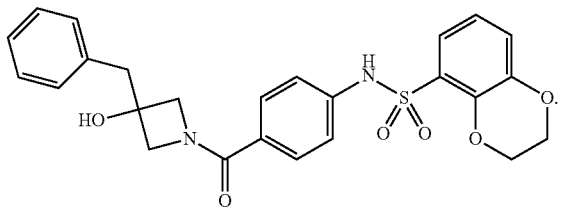 [SMILES: O=C(c1ccc(NS(=O)(=O)c2cccc3c2OCCO3)cc1)N1CC(O)(Cc2ccccc2)C1]

14. A pharmaceutical composition comprising a compound of claim 1 or a pharmaceutical acceptable salt thereof and a pharmaceutically acceptable carrier.

15. A method of modulating PKM2 activity in a subject in need thereof, the method comprising administering to said subject a pharmaceutical composition of claim 14.

16. A method for increasing the lifetime of red blood cells (RBCs) in need thereof comprising contacting blood with an effective amount of a compound of claim 1, or a pharmaceutically acceptable salt thereof.

17. The method of claim 16, wherein the compound is added directly to whole blood or packed cells extracorporeally.

18. The method of claim 16, wherein the pharmaceutical composition is administered to a subject in need thereof.

19. A method for regulating 2,3-diphosphoglycerate levels in blood in need thereof comprising contacting blood with an effective amount of a compound of claim 1.

20. A method for treating hereditary non-spherocytic haemolytic anemia comprising administering to a subject in need thereof a therapeutically effective amount of a compound of claim 1.

21. A method for treating sickle cell anemia comprising administering to a subject in need thereof a therapeutically effective amount of a compound of claim 1.

22. A method for increasing the lifetime of red blood cells (RBCs) in need thereof comprising contacting blood with an effective amount of a composition of claim 14.

23. A method for regulating 2,3-diphosphoglycerate levels in blood in need thereof comprising contacting blood with an effective amount of a composition of claim 14.

24. A method for treating hereditary non-spherocytic haemolytic anemia comprising administering to a subject in need thereof a therapeutically effective amount of a pharmaceutically acceptable composition of claim 14.

25. A method for treating sickle cell anemia comprising administering to a subject in need thereof a therapeutically effective amount of a pharmaceutically acceptable composition of claim 14.

* * * * *